United States Patent
Jepson et al.

(10) Patent No.: US 6,683,230 B1
(45) Date of Patent: Jan. 27, 2004

(54) HYBRID SEED PRODUCTION

(75) Inventors: Ian Jepson, Bracknell (GB); Allan Daly, Bracknell (GB); Mary Elizabeth Knight, Eaton (GB); Michael William Bayliss, Haslemere (GB)

(73) Assignee: Syngenta Limited (GB)

(*) Notice: Subject to any disclaimer, the term of this patent is extended or adjusted under 35 U.S.C. 154(b) by 0 days.

(21) Appl. No.: 09/601,812

(22) PCT Filed: Jan. 22, 1999

(86) PCT No.: PCT/GB99/00238

§ 371 (c)(1),
(2), (4) Date: Sep. 18, 2000

(87) PCT Pub. No.: WO99/42598

PCT Pub. Date: Aug. 26, 1999

(30) Foreign Application Priority Data

Feb. 20, 1998 (GB) .............................................. 9803659
Mar. 17, 1998 (GB) .............................................. 9805669

(51) Int. Cl.$^7$ .............................. A01H 1/00; A01H 1/02; A01H 5/10; C12N 15/82; C12N 15/29

(52) U.S. Cl. ........................ 800/271; 800/274; 800/278; 800/287; 800/303; 800/306; 800/312; 800/314; 800/317.4; 800/320; 800/320.1; 800/320.2; 800/320.3; 800/322; 435/468

(58) Field of Search ................................ 800/278, 287, 800/271, 274, 303, 320.3, 320, 320.2, 320.1, 317.4, 322, 306, 314, 312; 435/468

(56) References Cited

U.S. PATENT DOCUMENTS 5,432,068 A * 7/1995 Albertsen et al. ......... 435/172.3
5,633,441 A * 5/1997 De Greef et al. ............ 800/205
5,723,763 A * 3/1998 Mariani et al. ............. 800/205

FOREIGN PATENT DOCUMENTS

| EP | 0 198 288 A2 | 10/1986 |
|---|---|---|
| EP | 0 344 029 | 11/1989 |
| EP | 0 412 006 A1 | 2/1991 |
| EP | 0 412 911 A1 | 2/1991 |
| EP | 0 465 024 A1 | 1/1992 |
| WO | WO 90/08830 | 8/1990 |
| WO | WO 94/03619 * | 2/1994 |
| WO | WO 94/25593 | 11/1994 |
| WO | WO 95/20668 | 8/1995 |
| WO | WO 96/13588 | 5/1996 |
| WO | WO 96/17945 | 6/1996 |
| WO | WO 96/26283 | 8/1996 |
| WO | WO 96/27673 | 9/1996 |
| WO | WO 97/13401 | 4/1997 |
| WO | WO 97/30162 | 8/1997 |
| WO | WO98/39462 | 9/1998 |

OTHER PUBLICATIONS

Turgut et al. Plant Mol. Biol. 24(1): 97–104, 1994.*
Sessa et al. Plant Mol. Biol. 29(5):968–982, 1995.*
Napoli et al. Plant Cell 2: 279–289, Apr. 1990.*
Maruyama, K. et al., JARQ, vol. 24, pps.243–252, 1991.
Brown, D., Crop Science, vol. 24, pps. 1207–1208, Nov.–Dec. 1984.
Bingham, E., et al., The Journal of Heredity, vol. 75, pps. 231–233, 1984.
Daskalov et al. Theor. Appl. Genet. 76: 530–532.
Wright, Susan, et al., The Plant Journal, vol. 3, No. 1, pps. 41–49, 1993.
Albani, Diego, et al., Plant Molecular Biology, vol. 15, pps. 605–622, 1990.
Caddick, Mark, et al., Nature Biotechnology, vol. 16, pps. 177–180, Feb. 1998.
Hanson, Doris, et al., The Plant Cell, vol 1, pps. 173–179, Feb. 1989.
Hiei, Yukoh, et al., Plant Molecular Biology, vol. 35, pps. 205–218, 1997.
Christou, Paul, Plant Molecular Biology, vol. 35, pps. 197–203, 1997.
Ficker, M., et al., Plant Molecular Biology, vol. 35, pps. 425–431, 1997.
De Block, M., et al., Theor Appl Genet, vol. 95, pps. 125–131, 1997.
Nacken, W., et al., Mol Gen Genet, vol. 229, pps. 129–136, 1991.
Spena, A., et al., Theor Appl Genet, vol. 84, pps. 520–527, 1992.
Mariani, C., et al., Nature, vol. 357, pps. 384–387, Jun. 4, 1992. +Peacock, J. Nature 357: 358 (1992).
Mariani, C., et al., Nature, vol. 347, pps. 737–741, Oct. 25, 1990.+Peacock, J. Nature 347: 714–715.
Goldman, M., et al., The EMBO Journal, vol. 13, No. 13, pps. 2976–2984, 1994.
Salter, M. et al., The Plant Journal, vol. 16, No. 1, pps. 127–132, 1998.

* cited by examiner

Primary Examiner—David T. Fox
(74) Attorney, Agent, or Firm—Bruce Vrana

(57) ABSTRACT

Methods of preparing hybrid seed are described. One such method comprises interplanting a male parent plant which is male fertile and homozygous recessive female sterile and a female parent plant which is homozygous recessive male sterile and female fertile, allowing cross-pollination and obtaining the seed produced therefrom. The genomic material of each parent plant may also have integrated therein a gene construct comprising a promoter sequence-responsive to the presence or absence of an exogenous chemical inducer, optionally operably linked to one or more enhancer or intron sequences, operably linked to a gene which fully restores the fertility of each parent plant, the gene being expressed by the application to the plant of an external chemical inducer thereby allowing each parent to self-pollinate.

8 Claims, 42 Drawing Sheets

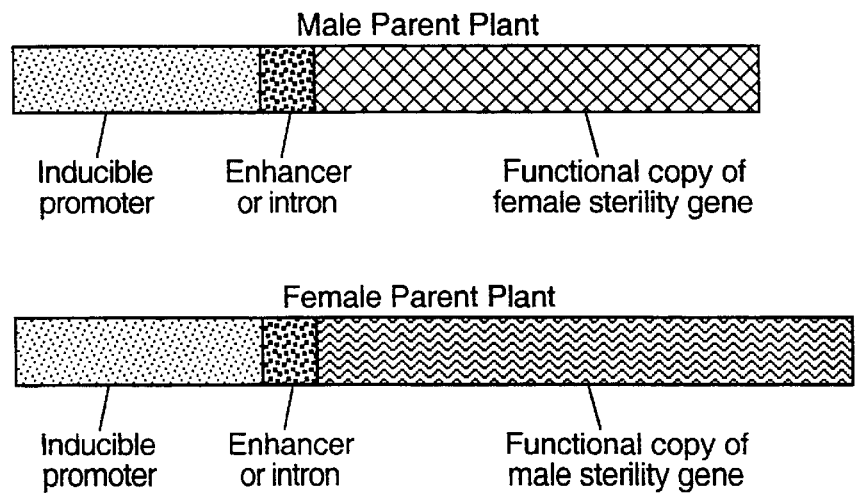
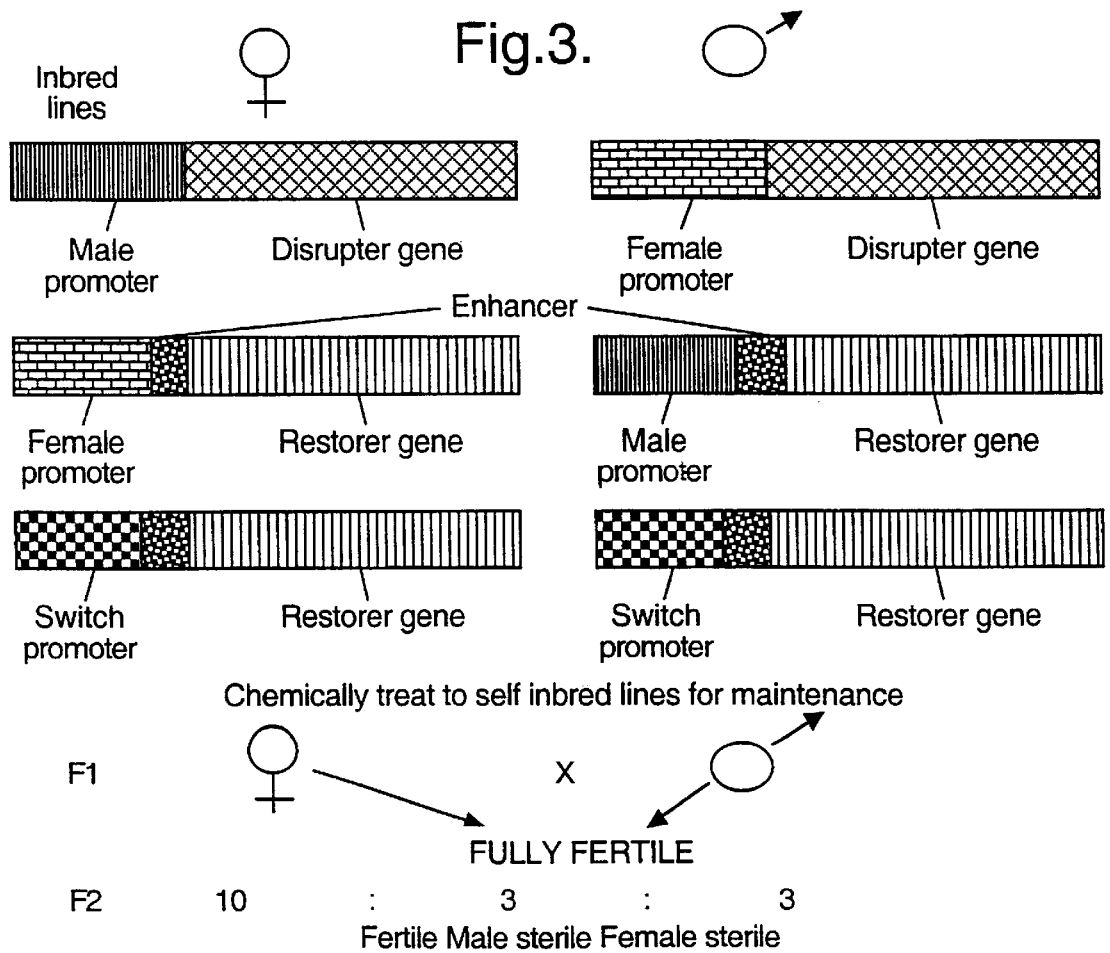

Fig.2A.

Male parent                  Female parent $$\frac{fsR^{FCS}}{fsR^{FCS}} \quad \frac{--------}{--------} \quad \times \quad \frac{msR^{MCS}}{msR^{MCS}} \quad \frac{====}{====}$$

Gametes:    $fsR^{FCS}$    --------    $msR^{MCS}$    ====

F1: $\frac{fsR^{FCS}}{====} \quad \frac{msR^{MCS}}{--------}$ note: $R^{FCS}$ and $R^{MCS}$ are dominant restorable fertility. ms and -------- are allelic, fs and === are allelic.

ALL F1 PLANTS ARE FULLY FERTILE

Fig.2B.

| Pollen → <br> Egg cell ↓ | $fsR^{FCS}$ <br> -------- | $fsR^{FCS}$ <br> $msR^{MCS}$ | $msR^{MCS}$ <br> === | === <br> -------- |
|---|---|---|---|---|
| $fsR^{FCS}$ <br> -------- | FS | FS | FF | FF |
| $fsR^{FCS}$ <br> $msR^{MCS}$ | FS | FS,MS | MS | FF |
| $msR^{MCS}$ <br> === | FF | MS | MS | FF |
| === <br> -------- | FF | FF | FF | FF |

Where MS=male sterile, FS=female sterile, FF=fully fertile
Segregation is 3 MS, 3FS, 9FF, 1 MS and FS

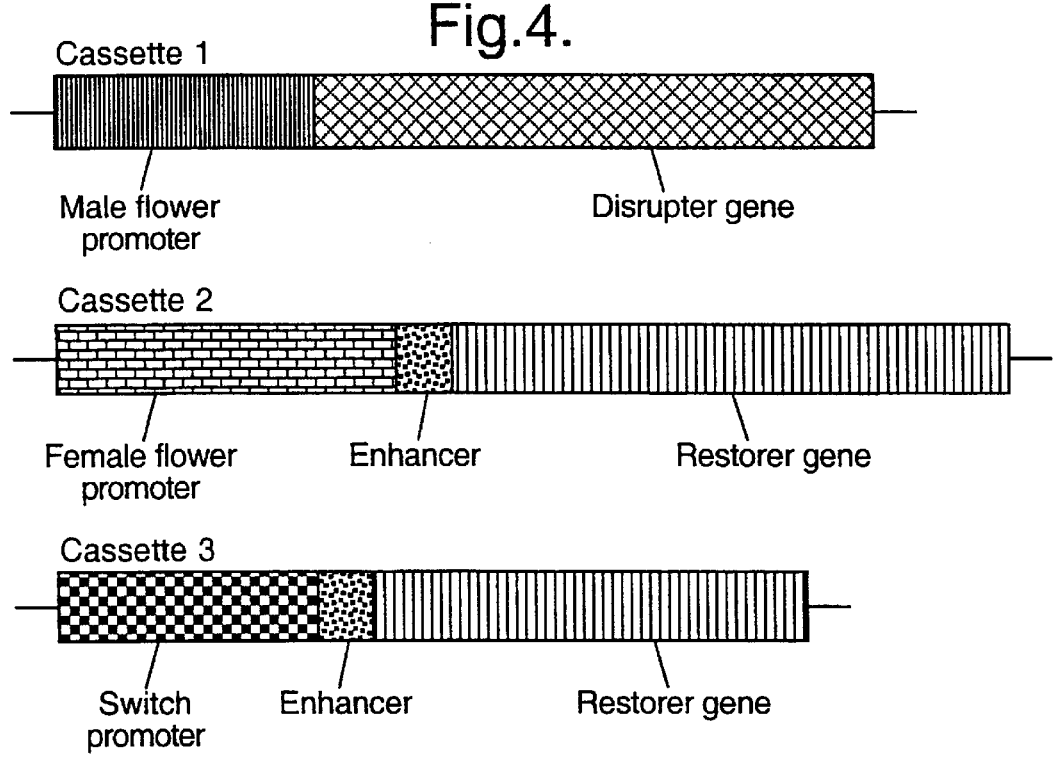
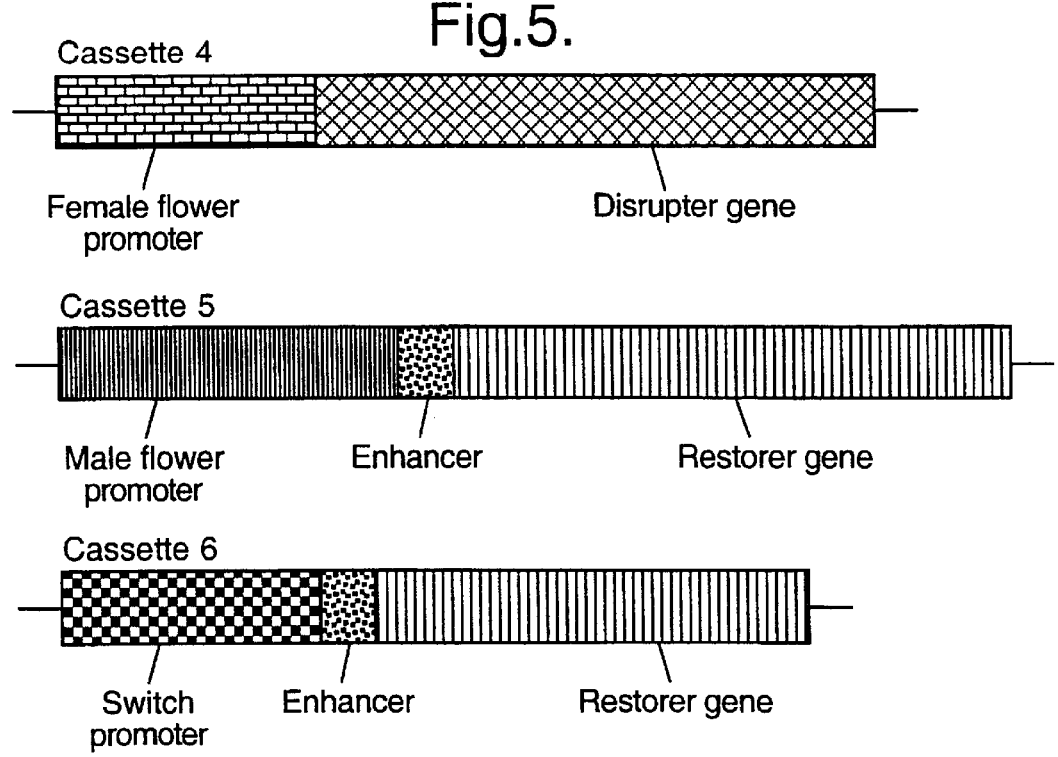

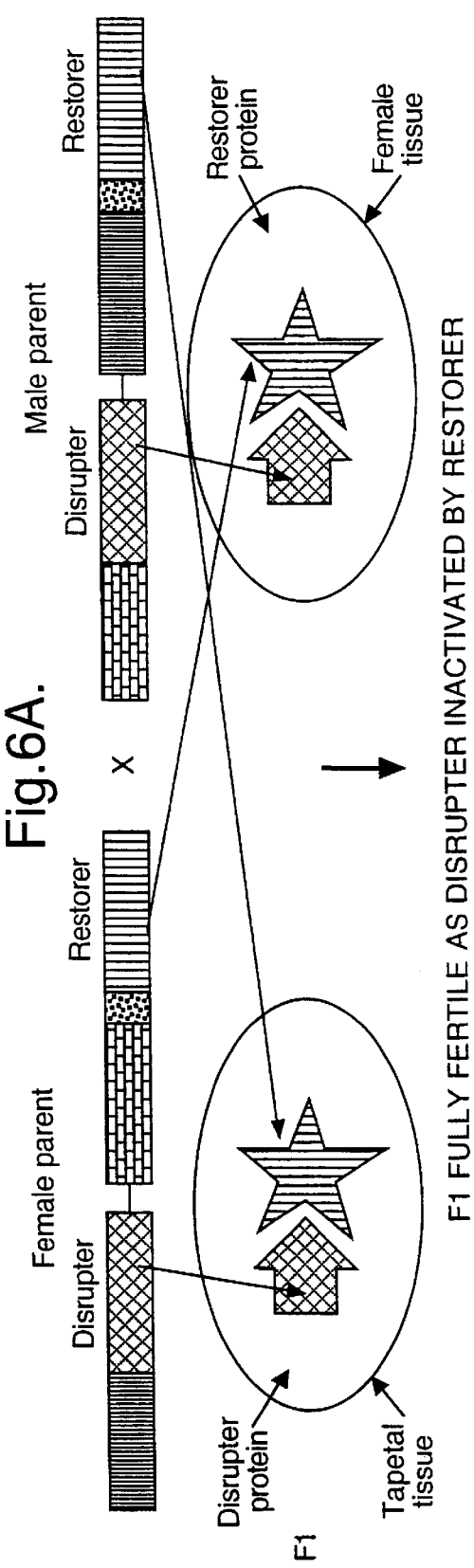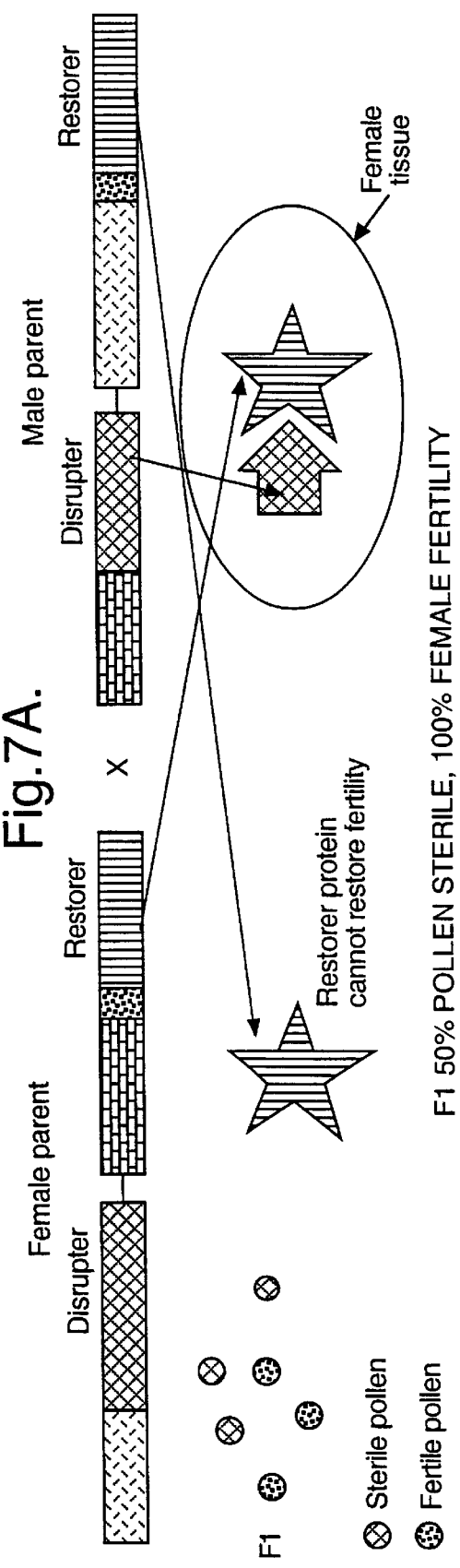

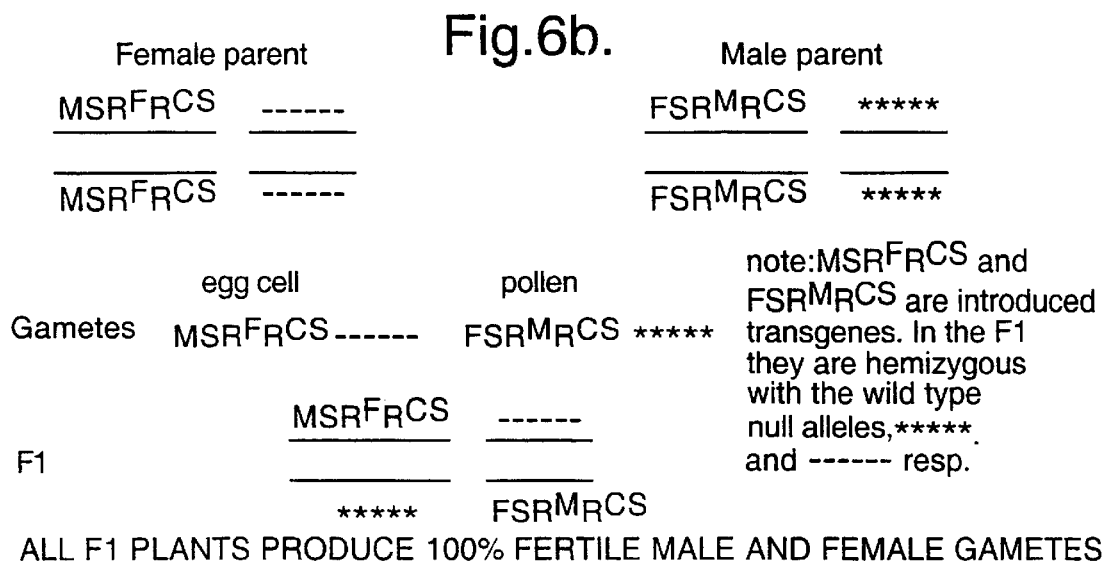

Fig. 6b.

Female parent          Male parent $\dfrac{\text{MSR}^F\text{R}^{CS} \quad \text{------}}{\text{MSR}^F\text{R}^{CS} \quad \text{------}}$      $\dfrac{\text{FSR}^M\text{R}^{CS} \quad \text{***}}{\text{FSR}^M\text{R}^{CS} \quad \text{***}}$ Gametes egg cell      pollen

MSR$^F$R$^{CS}$ ------    FSR$^M$R$^{CS}$ ***** note: MSR$^F$R$^{CS}$ and FSR$^M$R$^{CS}$ are introduced transgenes. In the F1 they are hemizygous with the wild type null alleles, *****, and ------ resp.

F1

$\dfrac{\text{MSR}^F\text{R}^{CS} \quad \text{------}}{\text{***** } \quad \text{FSR}^M\text{R}^{CS}}$

ALL F1 PLANTS PRODUCE 100% FERTILE MALE AND FEMALE GAMETES

Fig. 6c.

| Pollen → <br> Egg cell ↓ | MSR$^F$R$^{CS}$ <br> ------ | MSR$^F$R$^{CS}$ <br> FSR$^M$R$^{CS}$ | FSR$^M$R$^{CS}$ <br> ***** | ------ <br> ***** |
|---|---|---|---|---|
| MSR$^F$R$^{CS}$ <br> ------ | MS | FF | FF | MS |
| MSR$^F$R$^{CS}$ <br> FSR$^M$R$^{CS}$ | FF | FF | FF | FF |
| ***** <br> FSR$^F$R$^{CS}$ | FF | FF | FS | FS |
| ***** <br> ------ | MS | FF | FS | FF |

Where MS=male sterile,    FS=female sterile,    FF=fully fertile

Segregation is    3M,    3 FS,    10FF

Fig. 7b.

Female parent

MSR$^F$R$^{CS}$ ------
——————————
MSR$^F$R$^{CS}$ ------

Male parent

FSR$^M$R$^{CS}$ *****
——————————
FSR$^M$R$^{CS}$ *****

Gametes  egg cell       pollen
         MSR$^F$R$^{CS}$ ------   FSR$^M$R$^{CS}$ ***** note: MSR$^F$R$^{CS}$ and FSR$^M$R$^{CS}$ are introduced transgenes. In the F1 they are hemizygous with the wild type null alleles, *****. and ------ resp.

F1   MSR$^F$R$^{CS}$   ------
     ——————————
     *****             FSR$^M$R$^{CS}$

ALL F1 PLANTS PRODUCE 50% FERTILE POLLEN

Fig. 7c.

| Pollen →<br>Egg cell ↓ | MSR$^F$R$^{CS}$<br>------ | MSR$^F$R$^{CS}$<br>FSR$^M$R$^{CS}$ | *****<br>FSR$^M$R$^{CS}$ | *****<br>------ |
|---|---|---|---|---|
| MSR$^F$R$^{CS}$<br>------ | | | | |
| MSR$^F$R$^{CS}$<br>FSR$^M$R$^{CS}$ | | Fully Sterile | | |
| *****<br>FSR$^M$R$^{CS}$ | | | | |
| *****<br>------ | | | | |

ALL OTHERS SEGREGATING FOR STERILITY
AS A RESULT OF 50% POLLEN STERILE

FF

Fig. 11.
NORTHERN ANALYSIS
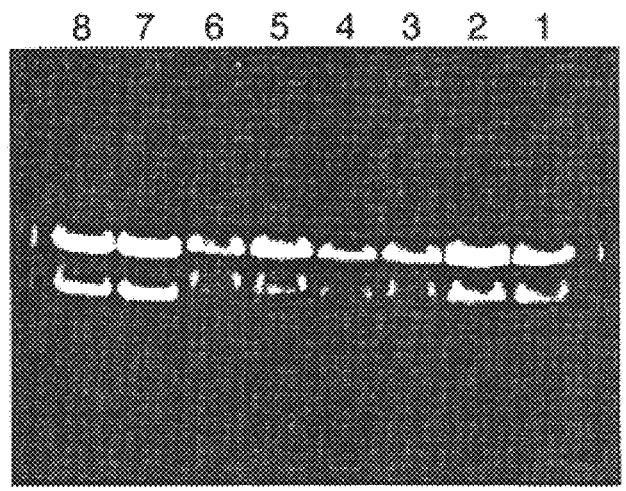
Ethidium bromide stained gel
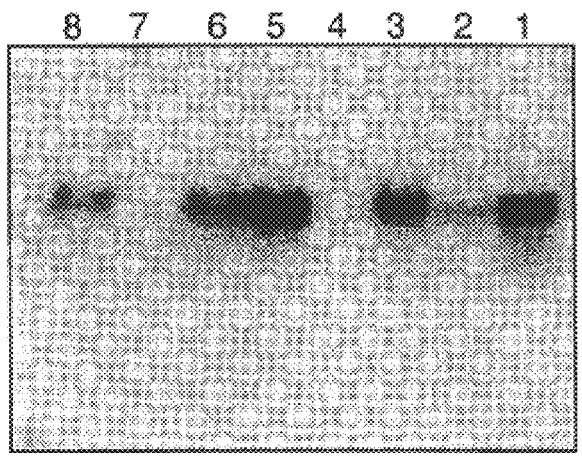
Northern hybridisation with GST II-27
1 = Induced Tassel
2 = Uninduced Edosperm ⎫
3 = Induced Endosperm ⎬ 14 d.a.p.
4 = Induced Embryo ⎭
5 = Uninduced Embryo ⎫
6 = Induced Embryo ⎪
7 = Uninduced Emdosperm ⎬ 24 d.a.p.
8 = Induced Endosperm ⎭

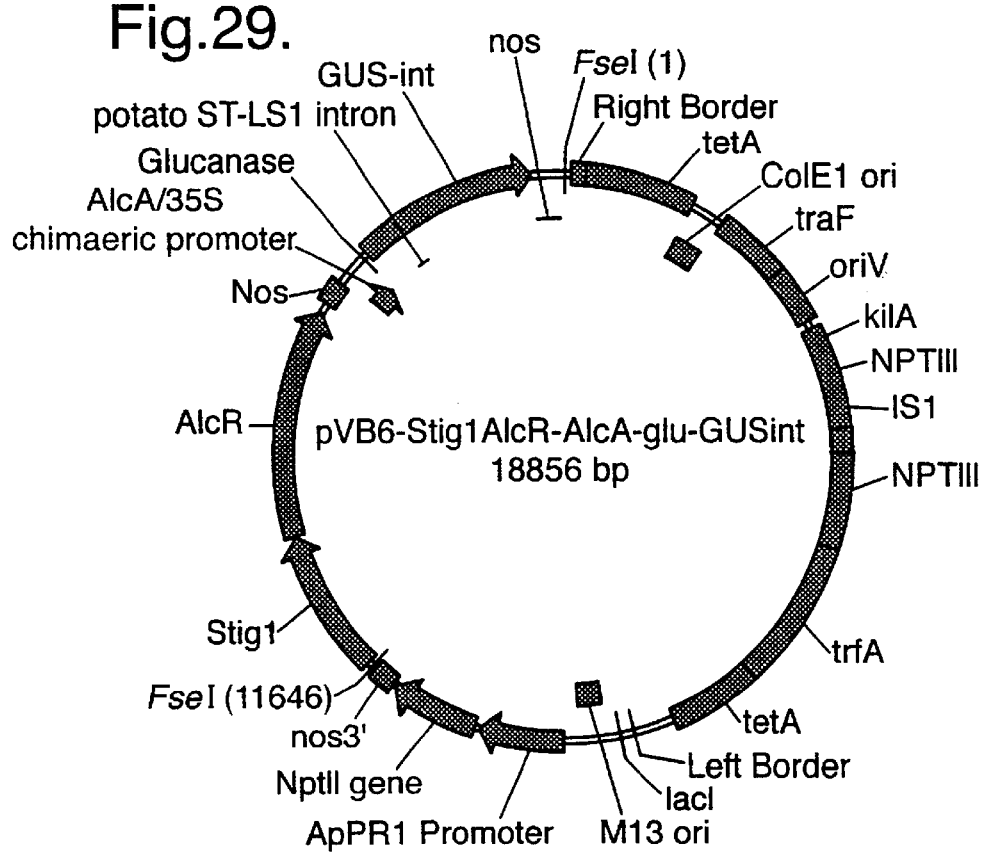
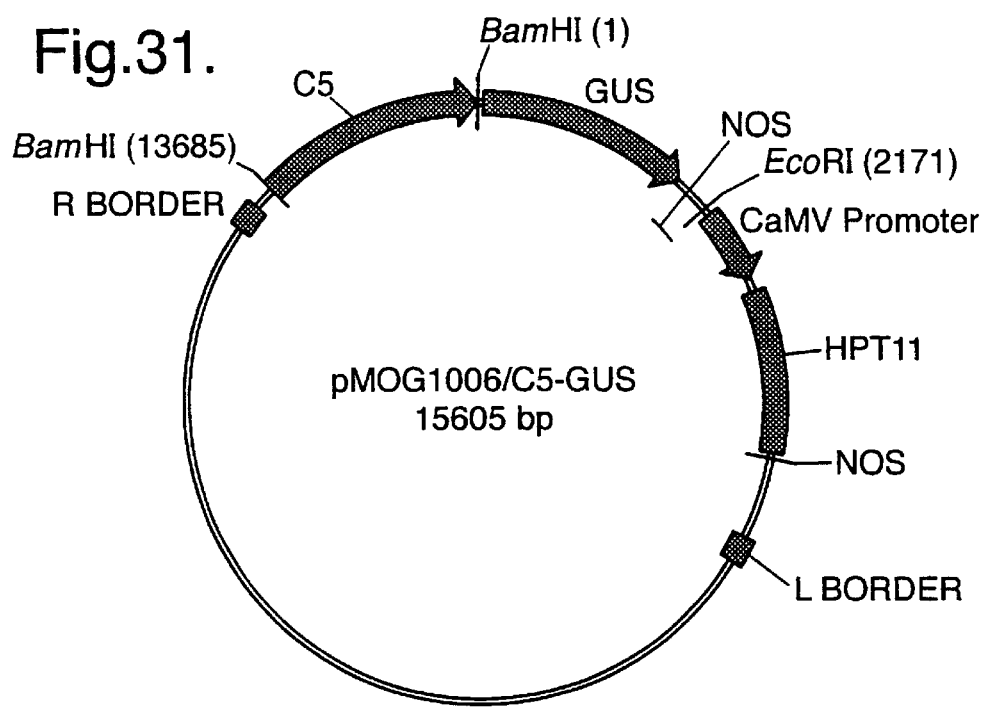

KEY TO GENES
1 = MFS14 promoter (5.8 kb fragment
2 = barnase
3 = nos poly A
4 = CaMV 35S promoter
5 = barstar
6 = Adh 1 intron
7 = bar
8 = ampicillin res.stance
9 = GST II-27 prom. 0.9kb Experiment to test the leakiness and inducibility of the AlcA promoter in transgenic tobacco callus GUS analysis of anthers from uninduced and induced tobacco plants H₂O Treated     5% Ethanol Treated
17-22mm Tobacco Buds H₂O Treated     5% Ethanol Treated
33-35mm Tobacco Buds Oil seed rape flower Alc-GUS before induction Oil seed rape flower Alc-GUS two days after 5% Ethanol root drench H₂O Treated      5% Ethanol Treated
Immature oil seed rape bud (petals removed)

Image of oil seed rape flower after 5% ethanol root drench

Image of oil seed rape flower after 5% ethanol root drench

Image of oil seed rape flower after 5% ethanol root drench

Wild type oil seed rape | Water induced Alc-GUS oil seed rape

Alc-GUS oil seed rape 2 days
after 2% ethanol root drench

H2O Treated　　　5% Ethanol
Alc-GUS plant　Treated Alc-GUS plants

Oil seed rape flower induced by standing flower stem in 5% ethanol, stained after two days GUS Staining in tomato anthers-expression from AlcA promoter GUS Staining in tomato pollen-expression from AlcA promoter

Fig.61.

```
GGATCCTGAAACATATCAGTTGTGTTTGTTTTTGTAAAT
CTTTTATACTACTAGGGGAGAAAATTAGCTTAGTTCAA
TCGCATCTCATATGTCTAATTACCAGGGGAGAAAATTA
GCTTAGTTCATTTGTTGCTGCCATATGGGTGAAAAAA
TAATGAGACATCTAAATCAGTAAATTGGAAATATAGC
ATCTTAAACCTGCAGGTAGTTTCTTAAACCTGATTCTA
GCTACAACTTAGTACAACTACTGGTAGTTTTTAAACC
TGATTCTAGCTACATGTTTATATTGTGGCACAAGAAC
TTTTAAGAACATATGCTGATGCCCACTGTATTTAGTTA
CTACTTCAAGACCAACTGTATTTAGTTACAAATGTGT
TTTCAAGATTGTAGAAATTTGTAGCTGAAATTATCCAC
ACCATATTTGTGAACTGACATCATTTCTAAGAATATTA
CTGATTAGAATCTTTCACTTTTATAATGCTTTGCAGGAG
TGGCCCCTCTGGAGTTGAATATGCAGTTATAACCAAAT
TTTACCCCTTTTATCCTAGAAGAGTTGCCAAGACACGG
TATAAGACCATGATAATAGACTAAGAGAGGATTTGGC
TCTAATTACTATATGTTTTATTTATGCAGTCCCATGAGA
ACTTTGAGTATTTGCAGATTGCTTTATTAATTTATTAAA
GTTAAAGATTGTATGTGTTGAGTATGTATCCACTCTTGT
TGGAAGTGTCTTGCAATTCCAATCCAAGGATGTATAAA
ATACTGCATGGGCTAAGTATGTGTTTTTCATGTATTTG
GAGTATATACTTTTGTTGCTTGAGAACATGTATGT
ACACTAGAAGCTTGTCAATTGTGTGAACTTGAGTTGAT
CCCTGTCTAACCTGAGTATATATATATATATTTTGTT
GCTTGAGAACAAGTATGTACAATAGAGGCTTGACAAT
TGTGTGAACTTGAGTTGAACATGAATTTTGATAATCAC
AACTCACCATCCCTTTCAATATGCTTAGAATATAGCTT
TTTATAATTTTTCACCCTACAATACAAAATTGTTCTATG
AAGGCCATGGTACATCATCATATCCTGTATTATCAACC
TAGGATTTGTCTATTTCGATTAATAATGGCATTGAGTC
AAATTTTGGTTGTTTCAAATGATAGACTTCGATATTTGT
TATGATTTATGAGTTGATTCTTGATAGCATTACTAAAA
AATGACCTATGTATACAAGTGTCTTCCGTTGCAACG
CACGGGCATATACCTAGTCAATCACTAAGACCCTAATT
TTGAAGTTGGGACTTAGACGTGTTCCACGTTTGTAAAG
GCGAGTATATAGGTGTATGTATATAAGAGCCGGTGTAT
```

Fig.61 (Cont).

ACAACAATTTTTTATAAGAAAACTTGAACAAGTAGCCA
GGTGTTGAAATCTTCATATATGTGCCGACGCCATTCAA
CATCATATTTGGCTTCTGGCGAGGATCGTAGTATCAAG
CAACATAAAAGCAATGACAAACAGCGAAGCACAAAG
ATCTCCAGGCTCGTCATAAACTAATCACAATGTTGTT
TGTCCTCCACAATTAGCACAACCCATTTTAGAAAAGA
TGCCACGATCGATCGAGACGTTGGCCAGCTATCAAAC
AGATAAGAACTACCCAAATATTTCCTAAATCCAGAAC
GGAAGACCCATTGACTAGGTCCTTACCTCTCAAATAGA
CAGACTATTCTTCTCCACATCAAAATATAGGGACTCCC
GATGCAACAAACACGGGCCACCACACAACAATGGTGA
AATGACCATGCATGCATCCACGTCCGTACGCAGCCATT
TCGTCTATAAATTTGCTTCCCATCCGATTCAACTAC<u>A A</u>
GCTTGCGGGCAAAA<u>ATG</u>GCAAGGCTC

The underlined A is the putative transcriptional start point, the bold and underlined ATG is the translational start point.

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: oligonucletoide

<400> SEQUENCE: 1
aattgatcgg ccggccctag            20

<210> SEQ ID NO 2
<211> LENGTH: 20
<212> TYPE: DNA
<213> ORGANISM: Artificial Sequence
<220> FEATURE:
<223> OTHER INFORMATION: oligonucletoide

<400> SEQUENCE: 2
aattctaggg ccggccgatc            20

<210> SEQ ID NO 3
<211> LENGTH: 55
<212> TYPE: DNA
<213> ORGANISM: Artificial Sequence
<220> FEATURE:
<223> OTHER INFORMATION: oligonucletoide

<400> SEQUENCE: 3
ccgtttaaac atttaaatgg cgcgccaagc ttgcggccgc cgggaattcg gccgg            55

<210> SEQ ID NO 4
<211> LENGTH: 55
<212> TYPE: DNA
<213> ORGANISM: Artificial Sequence
<220> FEATURE:
<223> OTHER INFORMATION: oligonucletoide

<400> SEQUENCE: 4
ccgaattccc ggcggccgca agcttggcgc gccatttaaa tgtttaaacg gccgg            55

<210> SEQ ID NO 5
<211> LENGTH: 28
<212> TYPE: DNA
<213> ORGANISM: Artificial Sequence
<220> FEATURE:
<223> OTHER INFORMATION: oligonucletoide

<400> SEQUENCE: 5
attcgacctc gcccccgagc tgtatatg            28

<210> SEQ ID NO 6
<211> LENGTH: 28
<212> TYPE: DNA
<213> ORGANISM: Artificial Sequence
<220> FEATURE:
<223> OTHER INFORMATION: oligonucletoide

<400> SEQUENCE: 6
gatgagaatg agaaggttga taaaagcc                                    28

<210> SEQ ID NO 7
<211> LENGTH: 18
<212> TYPE: DNA
<213> ORGANISM: Artificial Sequence
<220> FEATURE:
<223> OTHER INFORMATION: oligonucletoide

<400> SEQUENCE: 7
agcttctgga attcgtct                                               18

<210> SEQ ID NO 8
<211> LENGTH: 18
<212> TYPE: DNA
<213> ORGANISM: Artificial Sequence
<220> FEATURE:
<223> OTHER INFORMATION: oligonucletoide

<400> SEQUENCE: 8
agctagacga attccaga                                               18

<210> SEQ ID NO 9
<211> LENGTH: 20
<212> TYPE: DNA
<213> ORGANISM: Artificial Sequence
<220> FEATURE:
<223> OTHER INFORMATION: oligonucletoide

<400> SEQUENCE: 9
tcgattcggc ggccgccgaa                                             20

<210> SEQ ID NO 10
<211> LENGTH: 32
<212> TYPE: DNA
<213> ORGANISM: Artificial Sequence
<220> FEATURE:
<223> OTHER INFORMATION: oligonucletoide

<400> SEQUENCE: 10
ggtcgactct agaggaaccc cgggtaccaa gc                               32

<210> SEQ ID NO 11
<211> LENGTH: 32
<212> TYPE: DNA
<213> ORGANISM: Artificial Sequence
<220> FEATURE:
<223> OTHER INFORMATION: oligonucletoide

<400> SEQUENCE: 11
gcttggtacc cggggttcct ctagagtcga cc                               32

<210> SEQ ID NO 12
<211> LENGTH: 31
<212> TYPE: DNA
<213> ORGANISM: Artificial Sequence
<220> FEATURE:
<223> OTHER INFORMATION: oligonucletoide

```
<400> SEQUENCE: 12
agctattagc ggccgctatg tttaaacgcg t                                    31

<210> SEQ ID NO 13
<211> LENGTH: 31
<212> TYPE: DNA
<213> ORGANISM: Artificial Sequence
<220> FEATURE:
<223> OTHER INFORMATION: oligonucletoide

<400> SEQUENCE: 13
agctacgcgt ttaaacatag cggccgctaa t                                    31

<210> SEQ ID NO 14
<211> LENGTH: 51
<212> TYPE: DNA
<213> ORGANISM: Artificial Sequence
<220> FEATURE:
<223> OTHER INFORMATION: oligonucletoide

<400> SEQUENCE: 14
tcgagacaat ttcagctcaa gtgtttctta ctctctcatt tccattttag c              51

<210> SEQ ID NO 15
<211> LENGTH: 51
<212> TYPE: DNA
<213> ORGANISM: Artificial Sequence
<220> FEATURE:
<223> OTHER INFORMATION: oligonucletoide

<400> SEQUENCE: 15
catggctaaa atggttttga gagagtaaga aacacttgag ctgaaattgt c              51

<210> SEQ ID NO 16
<211> LENGTH: 31
<212> TYPE: DNA
<213> ORGANISM: Artificial Sequence
<220> FEATURE:
<223> OTHER INFORMATION: oligonucletoide

<400> SEQUENCE: 16
cggtatcgat aagctagata tcgaattcct g                                    31

<210> SEQ ID NO 17
<211> LENGTH: 31
<212> TYPE: DNA
<213> ORGANISM: Artificial Sequence
<220> FEATURE:
<223> OTHER INFORMATION: oligonucletoide

<400> SEQUENCE: 17
caggaattcg atatctagct tatcgatacc g                                    31

<210> SEQ ID NO 18
<211> LENGTH: 18
<212> TYPE: DNA
<213> ORGANISM: Artificial Sequence
<220> FEATURE:
<223> OTHER INFORMATION: oligonucletoide

<400> SEQUENCE: 18
cataaagctt atacagct                                                   18

<210> SEQ ID NO 19
<211> LENGTH: 18
```

```
<212> TYPE: DNA
<213> ORGANISM: Artificial Sequence
<220> FEATURE:
<223> OTHER INFORMATION: oligonucletoide

<400> SEQUENCE: 19
gtataagctt tatgagct                                                  18

<210> SEQ ID NO 20
<211> LENGTH: 18
<212> TYPE: DNA
<213> ORGANISM: Artificial Sequence
<220> FEATURE:
<223> OTHER INFORMATION: oligonucletoide

<400> SEQUENCE: 20
gatcgtatct cgagatac                                                  18

<210> SEQ ID NO 21
<211> LENGTH: 35
<212> TYPE: DNA
<213> ORGANISM: Artificial Sequence
<220> FEATURE:
<223> OTHER INFORMATION: oligonucletoide

<400> SEQUENCE: 21 gataaagcc ataattggat cctggtggtt tctgc                                35

<210> SEQ ID NO 22
<211> LENGTH: 35
<212> TYPE: DNA
<213> ORGANISM: Artificial Sequence
<220> FEATURE:
<223> OTHER INFORMATION: oligonucletoide

<400> SEQUENCE: 22
gcagaaacca ccaggatcca attatggctt ttatc                               35

<210> SEQ ID NO 23
<211> LENGTH: 34
<212> TYPE: DNA
<213> ORGANISM: Artificial Sequence
<220> FEATURE:
<223> OTHER INFORMATION: oligonucletoide

<400> SEQUENCE: 23
cggaactatc ccgaattctg caccgtttaa acgc                                34

<210> SEQ ID NO 24
<211> LENGTH: 34
<212> TYPE: DNA
<213> ORGANISM: Artificial Sequence
<220> FEATURE:
<223> OTHER INFORMATION: oligonucletoide

<400> SEQUENCE: 24
gcgtttaaac ggtgcagaat tcgggatagt tccg                                34

<210> SEQ ID NO 25
<211> LENGTH: 39
<212> TYPE: DNA
<213> ORGANISM: Artificial Sequence
<220> FEATURE:
<223> OTHER INFORMATION: oligonucletoide

<400> SEQUENCE: 25
```

```
gataaaagcc ataattggct cgaggtggtt tctgctgag                                  39

<210> SEQ ID NO 26
<211> LENGTH: 39
<212> TYPE: DNA
<213> ORGANISM: Artificial Sequence
<220> FEATURE:
<223> OTHER INFORMATION: oligonucletoide

<400> SEQUENCE: 26
ctcagcagaa accacctcga gccaattatg gcttttatc                                   39

<210> SEQ ID NO 27
<211> LENGTH: 29
<212> TYPE: DNA
<213> ORGANISM: Artificial Sequence
<220> FEATURE:
<223> OTHER INFORMATION: oligonucletoide

<400> SEQUENCE: 27
cgatgctttc ggaaccggta ccgaattcg                                              29

<210> SEQ ID NO 28
<211> LENGTH: 29
<212> TYPE: DNA
<213> ORGANISM: Artificial Sequence
<220> FEATURE:
<223> OTHER INFORMATION: oligonucletoide

<400> SEQUENCE: 28
cgaattcggt accggttccg aaagcatcg                                              29

<210> SEQ ID NO 29
<211> LENGTH: 1891
<212> TYPE: DNA
<213> ORGANISM: Artificial Sequence
<220> FEATURE:
<223> OTHER INFORMATION: ZmC5 promoter sequence in maize

<400> SEQUENCE: 29
ggatcctgaa acatatcagt tgtgtttgtt tttgtaaatc ttttatacta ctaggggaga           60
aaattagctt agttcaatcg catctcatat gtctaattac caggggagaa aattagctta          120
gttcattttg ttgctgccat atggggtgaa aaaataatga gacatctaaa tcagtaaatt          180
ggaaatatag catcttaaac ctgcaggtag tttcttaaac ctgattctag ctacaactta          240
gtacaactac tggtagtttt taaaacctga ttctagctac atgttttata ttgtggcaca          300 agaacttttta agaacatatg ctgatgccca ctgtatttag ttactacttc aagaccaact         360
gtattttagt tacaaatgtg ttttcaagat tgtagaaatt tgtagctgaa attatccaca          420
ccatatttgt gaactgacat catttctaag aatattactg attagaatct ttcactttta          480
taatgctttg caggagtggc ccctctggag ttgaatatgc agttataacc aaattttacc          540
ccttttatcc tagaagagtt gccaagacac ggtataagac catgataata gactaagaga          600
ggatttggct ctaattacta tatgttttat ttatgcagtc ccatgagaac tttgagtatt          660
tgcagattgc tttattaatt tattaaagtt aaagattgta tgtgttgagt atgtatccac          720
tcttgttgga agtgtcttgc aattccaatc caaggatgta taaaatactg catgggctaa          780
gtatgtgttt tttcatgtat ttggagtata tactttttt gttgcttgag aacatgtatg           840
tacactagaa gcttgtcaat tgtgtgaact tgagttgatc cctgtctaac ctgagtatat          900
atatatatat attttgttgc ttgagaacaa gtatgtacaa tagaggcttg acaattgtgt          960
```

```
                                         -continued gaacttgagt tgaacatgaa ttttgataat cacaactcac catcccttc aatatgctta     1020 gaatatagct ttttataatt tttcaccta caatacaaaa ttgttctatg aaggccatgg      1080
tacatcatca tatcctgtat tatcaaccta ggatttgtct atttcgatta ataatggcat    1140
tgagtcaaat tttggttgtt tcaaatgata gacttcgata tttgttatga tttatgagtt    1200
gattcttgat agcattacta aaaatgacc tatgtatata caagtgtctt ccgttgcaac     1260
gcacgggcat atacctagtc aatcactaag accctaattt tgaagttggg acttagacgt    1320
gttccacgtt tgtaaaggcg agtatatagg tgtatgtata taagagccgg tgtatacaac   1380
aattttttat aagaaaactt gaacaagtag ccaggtgttg aaatcttcat atatgtccg    1440 acgccattca acatcatatt tggcttctgg cgaggatcgt agtatcaagc aacataaaag    1500
caatgacaaa cagcgaagca caaagatctc ccaggctcgt cataaactaa tcacaatgtt   1560
gtttgtcctc cacaattagc acaacccatt ttagaaaaag atgccacgat cgatcgagac   1620
gttggccagc tatcaaacag ataagaacta cccaaatatt tcctaaatcc agaacggaag   1680
acccattgac taggtcctta cctctcaaat agacagacta ttcttctcca catcaaaata   1740
tagggactcc cgatgcaaca aacacgggcc accacacaac aatggtgaaa tgaccatgca    1800
tgcatccacg tccgtacgca gccatttcgt ctataaattt gcttccatc cgattcaact    1860 acaagcttgc gggcaaaaat ggcaaaggct c                                  1891
```

HYBRID SEED PRODUCTION

This application is a 371 of PCT/GB99/00238 filed Jan. 22, 1998.

FIELD OF THE INVENTION

The present invention relates to methods of preparing hybrid seed.

In particular, the present invention relates to the molecular control of sterility in crop plants. Such male and female sterility in plants can be used in the preparation of hybrid seed from crops which are naturally self-pollinators.

The present invention also provides for a method of restoring fertility in the parent plants to allow self-pollination, thereby allowing the maintenance of the parental lines.

The present invention further relates to expression cassettes for incorporation into plants and to the use of such expression cassettes in a male/female sterility restorer system.

Hybrid plants grown from hybrid seed benefit from the heterotic effects of crossing two distinct genetic backgrounds. The production of hybrid seed depends on the ability to control self-pollination and ensure cross-pollination of male and female parent plants.

A number of methods are available to control pollen fertility. For example, in the case of maize, which has separate male and female flowers, control of pollen fertility is achieved by physically removing the male inflorescence or tassel, prior to pollen shed, thus preventing self-pollination.

Most major crops, however, have both functional male and female reproductive organs within the same flower. In this instance, removal of the pollen producing organs is very labour intensive and expensive. The use of chemicals (gametocides), particularly in wheat, maize (corn) and rice, to kill or block pollen production produces transitory male sterility but the use of such chemicals is expensive. The reliability of the chemicals and their length of action are also issues.

There is considerable interest in developing systems of pollen control based on genetic mechanisms producing male sterility. There are two general types: a) nuclear male sterility caused by the failure of pollen production due to one or more nuclear genes and b) cytoplasmic male sterility (CMS) in which pollen production is blocked because of a defect in a gene in the mitochondria.

Currently available nuclear systems are based on the introduction of a male sterility trait to one parent plant followed by the introduction of a fertility restoration gene as a result of cross-pollination with another plant to produce fertile hybrid plants. The Paladin system, which is described in WO96/01799, is different and is based on the separation during hybrid seed production of genes which, when expressed together in one plant, have a cytotoxic effect leading to male sterility.

Rice and wheat are self-pollinating plants and have small hermaphrodite flowers and so the detasseling approach taken for hybrid seed production in maize is not applicable. Manual removal of anthers is difficult and time consuming. Moreover, wheat pollen is relatively heavy and is viable only for a short time, rarely remaining viable for longer than 30 minutes. The technique of planting used in hybrid corn production i.e. planting the male parent in a block physically separated from the female parent (the male sterile) and allowing wind pollination does not, therefore, work well in wheat or rice. The male and female parents for these crops have to be interplanted to ensure cross pollination. As hybrid seed needs to comprise more than 95% hybrids, it is necessary to remove seed arising from self-pollination of the male parent or to make the male parent incapable of self-fertilisation and therefore incapable of producing non-hybrid seed. Clearly, the interplanting of the parent plants means that the first option is difficult unless the male plants are susceptible to some chemical treatment to which the female parent is tolerant e.g. herbicide treatment.

Our International Patent Application No. PCT/GB90/00110 describes a cascade of gene sequences which expresses a protein which disrupts the biosynthesis of viable pollen in a female parent plant. In this case, however, only one of the parent plants i.e. the female parent is sterile to minimise self-pollination of the female plant and this female plant is crossed with a fertile male parent plant to yield fertile hybrid seed. There is no description in the literature, however, of a method of producing hybrid seed wherein both parent plants are unable to self-pollinate.

SUMMARY OF THE INVENTION

The present invention relates to two methods by which hybrid seed may be produced which seeks to overcome the problems presently associated with the production of hybrid seed, particularly with the production of hybrid wheat and rice seed.

According to a first aspect of the present invention, there is provided a method of preparing hybrid seed comprising interplanting a male parent plant which is male fertile and homozygous recessive female sterile and a female parent plant which is homozygous recessive male sterile and female fertile, allowing cross-pollination and obtaining seed produced therefrom.

According to a second aspect of the present invention, there is provided the use of the above method to produce hybrid seed.

According to a third aspect of the present invention, there is provided fertile plants produced by the aforementioned method.

According to a fourth aspect of the present invention there is provided the progeny of the aforementioned plants, the seeds of such plants and such progeny.

According to a fifth aspect of the present invention there is provided an expression cassette comprising:

(a) a first gene promoter sequence which is a male flower specific promoter sequence;

(b) a disrupter gene encoding a product capable of disrupting male fertility operably linked to the first gene promoter sequence;

(c) a second gene promoter sequence which is a female flower specific promoter sequence optionally operably linked to one or more translational enhancer or intron sequences;

(d) a restorer gene encoding a product capable of restoring female fertility operably linked to the second gene promoter sequence;

(e) a third gene promoter sequence responsive to the presence of an exogenous chemical inducer optionally operably linked to one or more translational enhancer or intron sequences; and (f) a restorer gene encoding a product capable of restoring male fertility operably linked to the third gene promoter sequence;

whereby the presence of the exogenous chemical inducer controls male fertility.

According to a sixth aspect of the present invention there is provided an expression cassette comprising:
 (a) a first gene promoter sequence which is a female flower specific promoter sequence;
 (b) a disrupter gene encoding a product capable of disrupting female fertility;
 (c) a second gene promoter sequence which is a male flower specific promoter sequence optionally operably linked to one or more translational enhancer or intron sequences;
 (d) a restorer gene encoding a product capable of restoring male fertility operably linked to the second gene promoter sequence;
 (e) a third gene promoter sequence responsive to the presence or absence of an exogenous chemical inducer optionally operably linked to one or more translational enhancer or intron sequences; and
 (f) a restorer gene encoding a product capable of restoring female sterility operably linked to the third gene promoter sequence;
whereby the presence of the exogenous chemical inducer controls female fertility.

According to a seventh aspect of the present invention there is provided a further method of producing hybrid seed comprising incorporating a first expression system according to the fifth aspect of the present invention into a first plant to generate a hemizygous female parent plant and incorporating a second expression system according to the sixth aspect of the present invention into a second plant to generate a hemizygous male parent plant;
 applying an exogenous chemical inducer to the transformants thereby allowing the plants to self-pollinate;
 growing up plants from the resulting seed;
 selecting for male and female homozygous plants;
 crossing the selected male and female plants; and
 obtaining the resulting hybrid seed.

According to an eighth aspect of the present invention there is provided plant tissue transformed with either one of the expression cassettes as defined above and material derived from the said transformed plant tissue.

According to a ninth aspect of the present invention there is provided fertile whole plants comprising the tissue or material as defined above.

According to a tenth aspect of the present invention there is provided the progeny of the selected plants produced according to the seventh aspect of the present invention, the progeny comprising expression cassettes as defined above incorporated, preferably stably incorporated, into their genome and the seeds of such plants and such progeny.

According to an eleventh aspect of the present invention, there is provided a plant, the genome of which comprises the first expression cassette according to the fifth aspect of the present invention.

According to a twelfth aspect of the present invention, there is provided a plant, the genome of which comprises the second expression cassette according to the sixth aspect of the present invention.

According to a thirteenth aspect of the present invention, there is provided hybrid seed produced by crossing these two plants and obtaining the resulting hybrid seed produced therefrom.

According to an fourteenth aspect of the present invention there is provided the use of the second method according to the present invention to produce hybrid seed.

According to a fifteenth aspect of the present invention there is provided a method of transforming a plant comprising incorporating into the genome of the plant an expression cassette as defined above wherein the restorer gene, which is operably linked to a third gene promoter sequence, is inducibly expressed in the target tissue but may be constitutively expressed in one or more other tissues so that the disrupter gene is only effective in the target tissue. The third promoter sequence may be constitutively expressed at a particular stage e.g. in callus tissue.

Preferably, the first method of the present invention wherein the genomic DNA of each parent plant has integrated therein a gene construct comprising a promoter sequence responsive to the presence or absence of an exogenous chemical inducer, optionally operably linked to one or more translational enhancer or intron sequences, operably linked to a gene which fully restores the fertility of each parent plant, the gene being expressed by the application to the plant of an external chemical inducer thereby allowing each parent to self-pollinate.

Preferably, the female parent plant is homozygous for a recessive gene which disrupts the biogenesis of viable pollen or which significantly reduces the viability of the pollen.

Preferably, the male parent plant is homozygous for a recessive gene which disrupts female floral structures such as ovule, style, stigma in such a way that fertilisation is prevented, or adhesion, hydration or germination of pollen inhibited or which inhibits pollen tube growth or guidance.

Preferably, the inducible promoter sequence is the AlcA promoter sequence or the GST-27 promoter sequence.

Preferably, the parent plants are wheat, barley, rice, maize, sugarbeet, tomato, sunflower, canola, cotton, soybean and other vegetables such as lettuce.

Preferably, the F1 hybrid seed produced by the first method of the present invention gives rise to plants, all of which are fully fertile.

Preferably, the F2 hybrid seed produced by the first method of the present invention gives rise to plants which segregate for sterility, about 25% being female sterile.

Preferably, the sterility of the parents is caused by a natural or genetically manipulated mutation.

Preferably, the first expression cassette defined above and used in the second method of the present invention comprises a disrupter gene encoding a product which is capable of disrupting pollen production.

Preferably, the first expression cassette defined above comprises a disrupter gene encoding a product which is capable of being expressed in the tapetal cells of the plant.

Preferably, the third gene promoter sequence in the first expression cassette is the AlcA promoter sequence or the GST-27 promoter sequence.

Preferably, the second expression cassette defined above and used in the second method of the present invention comprises a restorer gene encoding a product which is capable of restoring pollen production.

Preferably, the second expression cassette defined above comprises a restorer gene which is capable of overcoming disruption of the tapetal cells.

Preferably, the third gene promoter sequence in the second expression cassette is the AlcA promoter sequence or the GST-27 promoter sequence.

Preferably, the male plants in the second method according to the present invention comprise a homozygous dominant gene restoring male fertility.

Preferably, the female plants in the second method according to the present invention comprise a homozygous dominant gene restoring female fertility.

Preferably, the F1 hybrid seed produced gives rise to plants, the anthers of which produce approximately 50% of viable pollen, where the first gene promoter sequence of the first expression cassette is a gametophytic promoter sequence.

Preferably, the F1 hybrid seed produced gives rise to plants, all of which are fully fertile where the first promoter sequence of the first expression cassette is a sporophytic promoter sequence.

Preferably, the F2 hybrid seed gives rise to plants which segregate for sterility, of which a significant number are female sterile.

Preferably, the male and female homozygous plants produced by the second method according to the present invention are multiplied and maintained by the application of an exogenous chemical inducer to the plants, thereby allowing the plants to self-pollinate. In this regard, further generations of self-pollination of the selected male and female homozygous plants can be produced and when hybrid seed is required, the plants may be crossed to obtain hybrid seed.

Preferably, the plants used in the second method of the present invention are wheat, barley, rice, maize, sugarbeet, tomato, sunflower, canola, cotton, soybean and other vegetables.

Preferably, the restorer gene used in the method of transforming a plant according to the present invention is constitutively expressed in callus tissue from which transformed plants are regenerated.

Preferably, the restorer gene is inducibly expressed in the male or female flower structures.

Preferably, the third gene promoter sequence of the expression cassettes used in the transformation process is the GST-27 or the AlcA promoter sequence.

A preferred embodiment of the present invention is a method of preparing hybrid seed comprising interplanting a male parent plant which is male fertile and homozygous recessive female sterile and a female parent plant which is homozygous recessive male sterile and female fertile, allowing cross-pollination and obtaining seed produced therefrom wherein the genomic DNA of each parent plant has integrated therein a gene construct comprising a promoter sequence responsive to the presence or absence of an exogenous chemical inducer operably linked to a gene which fully restores the fertility of each parent plant, the gene being expressed by the application to the plant of an external chemical inducer thereby allowing each parent to self-pollinate when required for multiplication of the seed stocks of each parent plant.

A further preferred embodiment of the present invention is an expression system comprising:

(a) a first gene promoter sequence which is a male flower specific promoter sequence;

(b) a disrupter gene encoding a product capable of disrupting male fertility operably linked to the first gene promoter sequence;

(c) a second gene promoter sequence which is a female tissue specific promoter sequence optionally operably linked to one or more translational enhancer or intron sequences;

(d) a restorer gene encoding a product capable of restoring female fertility operably linked to the second gene promoter sequence;

(e) a third gene promoter sequence responsive to the presence or absence of an exogenous chemical inducer optionally operably linked to one or more translational enhancer or intron sequences;

(f) a restorer gene encoding a product capable of restoring male fertility operably linked to the third gene promoter sequence;

whereby the presence of the exogenous chemical inducer controls male fertility, wherein the gene capable of disrupting male sterility is a disrupter gene encoding a product which is expressed in the tapetal cells of the plant.

Another preferred embodiment of the present invention is an expression system comprising:

(a) a first gene promoter sequence which is a female tissue specific promoter sequence;

(b) a disrupter gene encoding a product capable of disrupting female fertility;

(c) a second gene promoter sequence which is a male tissue specific promoter sequence optionally operably linked to one or more translational enhancer or intron sequences;

(d) a restorer gene encoding a product capable of restoring male fertility operably linked to the second gene promoter sequence;

(e) a third gene promoter sequence responsive to the presence or absence of an exogenous chemical inducer optionally linked to one or more translational enhancer or intron sequences; and (f) a restorer gene encoding a product capable of restoring female fertility operably linked to the third gene promoter sequence;

whereby the presence of the exogenous chemical inducer controls female fertility and wherein the gene capable of restoring male fertility is a gene which encodes a product which restores pollen production in the tapetal cells.

The preferred male flower specific promoter sequences are the maize MSF14 and C5 (derived from pectin methyl esterase) promoter sequences.

The term "plant material" includes a developing caryopsis, a germinating caryopsis or grain, or a seedling, a plantlet or plant, or tissues or cells thereof, such as the cells of a developing caryopsis or the tissues of a germinating seedling or developing grain or plant (eg in the roots, leaves and stem).

The term "cassette" which is synonymous with terms such as "construct", "hybrid" and "conjugate" includes a gene of interest directly or indirectly attached to a gene promoter sequence. An example of an indirect attachment is the provision of a suitable spacer group such as an intron or enhancer sequence intermediate the promoter and the gene of interest. Such constructs also include plasmids and phage which are suitable for transforming a cell of interest.

The term "disrupter gene" is a gene which acts in a dominant fashion, and when expressed at a suitable stage of plant development, will lead to the failure of a plant to form normally functioning female flower structures or normally functioning male flower structures so that the plant is female or male sterile. Such a gene may exert its effect by disrupting tissues such as the tapetum and endothelium. The gene may be expressed specifically in male flowers during pollen formation causing cell death of the anthers and associated tissues, pollen mother cells, pollen and associated tissues. It may also be expressed in the stigma or in the transmitting tract of the style, thus interfering with the process of pollen adhesion, hydration, pollen germination and pollen tube growth and guidance. The origin of the disrupter genes can be from a variety of naturally occurring sources e.g. human cells, bacterial cells, yeast cells, plant cells, fungal cells, or they can be totally synthetic genes which may be composed of DNA sequences, some of which may be found in nature, some of which are not normally found in nature or a mixture of both. These genes will preferably have an effect on mitochondrial metabolism, as it is known that a good energy supply is an absolute requirement for the production of fertile pollen. The disrupter genes may, however, be effectively targeted to other essential biochemical functions such as DNA and RNA metabolism, protein synthesis, and other metabolic pathways. The preferred dominant disrupter gene is barnase.

The term "restorer gene" is a gene which acts in a dominant fashion, and when expressed, will reverse the effects of the disrupter gene. The preferred dominant restorer gene is barstar.

The term "female flower" is intended to include all parts of the female reproductive organs including but not limited to, ovary, ova, pistil, style, stigma, transmitting tract, placenta.

The term "male flower" is intended to include all parts of the male flower, including but not limited to, the tapetum, anthers, stamens, pollen.

The methods of hybrid seed production according to the present invention are different from and have a number of advantages over existing methods in a number of ways. The utilisation of both male and female sterility has not previously been described. This feature prevents self pollination of either parent thus allowing the production of hybrid seed without the need for separate planting blocks for male and female parents. This interplanting of male and female parent plants maximises the opportunity for cross pollination in crops, such as wheat and rice, which are essentially self pollinators. In the examples of wheat and rice, where block planting is not carried out, this method allows production of hybrid seed without the need to apply herbicide to rogue out male parent plants after fertilisation of the female parent. A chemically inducible restorer system is needed only for the maintenance of homozygous parental lines rather than for the hybrid seed production process. This means that chemicals are applied to limited acreages and then only infrequently. A number of disrupter-restorer systems, or operator-repressor systems may be used in the present invention.

Plants containing the expression cassettes of the present invention which control male and female fertility may also be used separately to make F1 hybrids with other parent lines, which do not contain the expression cassettes, if suitable alternative control of male or female fertility (such as mechanical removal of anthers or ovules, or use of chemical gametocides) is used in the other line. If the progeny from these F1 hybrids are then backcrossed for an appropriate number of generations to the other hybrid parents, whilst selecting for the presence of the expression cassette with molecular, biochemical or progeny-testing techniques, the system for controlling male or female fertility can be transferred or introgressed into new parent backgrounds. Alternatively, F1 hybrids with other parent lines can be self-pollinated, through application of an exogenous chemical inducer to restore male or female fertility as appropriate, so as to select new hybrid parents containing the expression cassettes, through the normal process of plant breeding. Use of such introgression and plant breeding will permit the methods of hybrid seed production of the present invention to be used with a wide variety of new and existing F1 hybrid parental combinations.

Promoters which are inducible by application of exogenous chemicals are known in the art. Suitable inducible promoters are those which are activated by application of a chemical, such as a herbicide safener. Examples of inducible promoters include AlcA/R switch system described in our International Publication No. WO. 93/21334, the GST switch system described in described in International Publication Nos WO 90/08826 and WO 93/031294 or the ecdysone switch described in International Publication No. WO 96/37609. Such promoter systems are herein referred to as "switch promoters". The switch chemicals used in conjunction with the switch promoters are agriculturally acceptable chemicals making these promoters particularly useful in the methods of the present invention.

One of the advantages of using the AlcA promoter, which is a component of the Alc A/R switch system, in the present invention is that the chemical inducer used is ethanol. This chemical is advantageous in that it can be applied as a root drench, as an aqueous spray, or as a gas. It is effective at concentrations of 1% and is non-toxic to operators and to the environment.

The present invention can be used for any mono- or di-cotyledonous plant which the breeder or grower wants to produce as F1 hybrid seed and for which suitable transformation techniques are or become available, particularly wheat and rice crops. The present invention has the advantage of reducing crop management costs associated with the F1 hybrid seed production, ease of purity control of hybrid seed and maintenance of parental lines.

In a particular application, the present invention relates to the production of male and female parental plants, which are rendered sterile using molecular engineering techniques. The sterility of these plants can be reversed by using a chemical application which leads to the restoration of fertility.

The anther is the site of male reproductive processes in flowering plants. It is composed of several tissues and cell types and is responsible for producing pollen grains that contain the sperm cells. The tapetum is a specialised tissue which plays a critical role in pollen formation. It surrounds the pollen sac early in pollen development, degenerates during the latter stages of development and is not present in an organised form in the mature anther. The tapetum produces a number of compounds which aid pollen development or are incorporated into the pollen outer wall and it has been demonstrated that many of the natural male sterility mutations have impaired tapetum differentiation or function. Tapetal tissue is therefore critical to the formation of functional pollen grains.

A number of genes have been identified and cloned that are specifically expressed in tapetal tissue. They include Osg6B, Osg4B (Tsuchiya et al. 1994, Yokoi, S et al. 1997), pE1, p T72 (WO9213957), p CA55 corn (WO92/13956), TA29, TA13, (Seurinck et al 1990), RST2 corn (W09713401), MS14,18,10 and A6, A9 from *Brassica napus* (Hird et al. 1993).

A tapetum specific promoter isolated from rice has been shown to give rise to male sterile plants when used to drive expression of β 1,3 glucanase in tobacco, (Tsuchiya et al. 1995). The tapetum specific promoter TA29 has been used to produce male sterile tobacco (Mariani et al 1990) and pCA55, pE1 and pT72 to produce male sterile wheat (De Block et al. 1997) when driving the expression of barnase.

Pollen specific clones have been obtained from a number of species, including corn (Hanson et al. 1989, Hamilton et al. 1989,) and tomato (Twell et al. 1990, 1991).

Anther specific clones have been isolated from a number of species Bp4A and C from *Brassica napus* (Albani et al. 1990), chs from petunia (Koes et al. 1989), rice (Xu et al. 1993, Zou et al. 1994), amongst others.

Wheat homologues of these clones and others may be obtained by such methods as degenerate PCR, utilising sequences found in the literature, and subsequent screening of wheat and other genomic libraries, and analysis of tissue specificity using the expression of reporter genes. These methods are well documented in the literature.

In higher plants the female reproductive organ is represented by the pistil, composed of the ovary, style and stigma. The gynoecium has been shown to contain up to 10,000 different mRNAs not present in other organs (Kamalay and Goldberg 1980). These include regulatory genes responsible for controlling pistil development as well as "downstream" ones encoding proteins associated with differentiated cell types in the pistil. Genes governing self-incompatibility and their homologues are one class of gene with pistil predominant expression patterns (Nasrallah et al. 1993). Other cloned genes include β glucanase (Ori et al. 1990), pectate lyase (Budelier et al. 1990) and chitinase (Lotan et al. 1989) which are expressed in the transmitting tissue and a proteinase inhibitor (Atkinson et al. 1993) which are expressed in the style. Others are pathogenesis related or are homologues of genes involved in the cleavage of glycosidic bonds. These enzymes may facilitate pollen tube growth by digesting proteins in the tissue through which the pollen tube grows.

A number of female sterile mutants have been identified in Arabidopsis. For example, sin1 (short integument) (Robinson-Beers et al. 1992) and bel1 (bell) (Robinson-Beers et al. 1992) affect ovule development. The Aintegumenta mutation blocks megasporogenesis at the tetrad stage (Elliot, R. C, et al. 1996, Klucher, K. M, 1996). A lethal ovule 2 mutation has been observed but not cloned in maize (Nelson et al. 1952). Pistil specific basic endochitinases have been cloned from a number of species (Ficker et al. 1997, Dzelzkalns et al. 1993, Harikrishna et al. 1996, Wemmer et al. 1994) and extensin-like genes have been shown to be expressed in the styles of *Nicotiana alata* (Chen C-G, et al. 1992).

The following are ovule specific clones ZmOV23,13, (Greco R., et al. unpublished), OsOsMAB3A (Kang H. G., et al. 1995), ZmZmM2 (Theissen G., et al. 1995) and stigma specific stig1 (Goldman, M. H et al. 1994), STG08, STG4B12 (EP-412006-A). Goldman et al. used the promoter from the STIG1 gene to drive expression of barnase in the stigmatic secretory zone. This led to flowers having no secretory zone in the pistils and thus were female sterile. Pollen grains were able to germinate but were unable to penetrate the surface.

Seven ovule specific cDNAs have been isolated from orchid (Nadeau et al. 1996). Again, wheat homologues of these and any others may be obtained by standard molecular biology techniques.

Another aspect to the methods of the present invention is the identification of genes impacting on male and female sterility. Such genes can be used in a variety of systems to control fertility.

The procedure for tagging maize genes with transposable elements has been reviewed (Doring, 1989). One of the methods which can be used is to cross a maize line carrying active transposable elements and a dominant allele of the target gene with a normal maize strain that does not carry transposable elements. Progeny from the cross can be selfed and screened for the most desirable mutations, i.e. those that lead to sterility. The sterile plants represent potential instances in which a transposable element has transposed to a locus bearing a gene essential for fertility. The genes may then be recovered in a variety of ways. U.S. Pat. No. 5,478,369 describes the isolation by this method of a gene described as MS45.

A male fertility gene has been identified in *Arabidopsis thaliana* using the En/Spm-I/dSpm transposon tagging system to obtain a male sterility 2 (ms2) mutant and the MS2 gene (Aarts et al. 1993). This MS2 gene has been shown to be involved in male gametogenesis, cell wall synthesis does not proceed after microspore mother cell meiosis and the microspores are eventually degraded. Homologues of MS2 have been identified in *Brassica napus, Zea Mays* and to an open reading frame found in wheat mitochondrial DNA. The isolation of genes critical to fertility in Arabidopsis may therefore lead to the cloning of homologues in other species. This approach can clearly be taken to isolate other genes critical to fertility.

There is now evidence for the existence of extensive regions of conserved colinearity among grass species at the genetic level. Ahn and Tanksley (1993) showed the relationship between rice and maize and Kurata et al (1994) showed that the wheat genome could be aligned with rice and Moore et al (1995) showed that all three maps could be aligned. This opens the way to the use of comparative genome mapping as a means of gene isolation.

The microsynteny approach to gene cloning is based on the emerging similarity in molecular marker and gene order among evolutionary related species. This approach is particularly attractive for large genome cereal species of agricultural importance like wheat, maize and barley that may take advantage of their small genome relative, rice. Kilian et al. (1997) report on progress on map-based cloning of the barley RpgI and rpg4 genes using rice as an intergenomic mapping vehicle.

As the above approach is limited to target genes which have been genetically mapped, an alternative method of gene isolation, which is an effective transposon tagging system, is being developed in rice using the maize Ac/Ds system, Izawa et al (1997).

A number of methods have been suggested as being useful to inactivate genes necessary for fertility or to produce cytotoxic compounds in the tissues to prevent normal development of gametophytes.

Our International patent application no. PCT/GB96/01675 describes a method of inhibiting gene expression in a target plant tissue using a disrupter gene selected from zANT, tubulins, T-urf, ATP-ase subunits, cdc25, ROA, MOT.

There are several other known inactivating systems. For example, barnase (Mariani et al. 1990), diphtheria toxin A-chain, pectate lyase. Two examples of expressing cytotoxic compounds previously described are avidin expression and IamH/IamS, The expression of β-1,3-glucanase in tapetal cells has been shown to generate male sterile plants (Worrall et al. 1992). Anti-sense has been proposed as a mechanism by which the expression of genes critical to pollen development can be down regulated and it has been shown (Van der Meer 1992) that antisense inhibition of flavonoid biosynthesis does indeed lead to male sterility. Reduction of flavanol expression has been claimed in maize to result in male sterility (WO 93 18171 Pioneer Hi-Bred International). Other mechanisms have also been described (Spena et al. 1992).

Baulcombe (1997) describes a method of gene silencing in transgenic plants via the use of replicable viral RNA vectors (Amplicons™) which may also be useful as a means of knocking out expression of endogenous genes. This method has the advantage that it produces a dominant mutation i.e. is scorable in the heterozygous state and knocks out all copies of a targeted gene and may also knock out isoforms. This is a clear advantage in wheat which is hexaploid. Fertility could then be restored by using an inducible promoter to drive the expression of a functional copy of the knocked out gene.

Kempin et al. (1997) report the targeted disruption of a functional gene using homologous recombination. This method normally, however, produces a recessive mutation i.e. is scorable only in the homozygote. To be detectable in the heterozygous state it would either have to be lethal directly or, for example, cause a block in a pathway such that there was a build up of a cytotoxic compound leading to lethality. In order to detect a sterility mutation it would be necessary to generate a recessive homozygote by self-pollination, where one in four of the progeny would be sterile. The switch construct allowing expression of the knocked out gene would have to be introduced into a heterozygote obtained by back crossing the homozygote. This is a potentially useful method for generating the recessive mutants needed for the method later described in Example 1.

Ribozymes are RNA molecules capable of catalysing endonucleoolytic cleavage reactions. They can catalyse reactions in trans and can be targeted to different sequences and therefore are potential alternatives to antisense as a means of modulating gene expression. (Hasselhof and Gerlach). Wegener et al (1994) have demonstrated the generation of a trans-dominant mutation by expression of a ribozyme gene in plants.

Several methods are known for altering plant self incompatibilty systems by modifying S-gene expression as a means of introducing male sterility in which a plant is transformed with a construct utilising a gametophytic S-gene encoding a ribonuclease in such a way that a self-incompatible plant is converted to self compatible or that a self-compatible plant is converted to self-incompatibility, thus preventing self pollination.

Examples of combinations of disrupter/restorer genes include barnase and barstar, and TPP and TPS. The use of the barnase/barstar system to firstly generate sterility and then restore fertility has been described (Mariani et al. (1992). Trehalose phosphate phosphatase (TPP) when expressed in tapetal cells of tobacco using the tapetum specific promoter Tap1 (Nacken et al 1991) from Antirrhinum results in male sterility. It is thought to be as a result of changing the carbohydrate metabolic and photosynthetic capacity of the tissues in which it is expressed. Anthers show signs of necrosis and any pollen produced is dead. Back crossing with wild type tobacco results in normal seed development. Analysis of the progeny shows that sterility segregates with the transgene. TreC, trehalose-6-phosphate hydrolase is a second gene whose expression perturbs of levels of trehalose-6-phosphate and it has been shown that when it is expressed using the constitutive plastocyanin promoter the result is bud excision before flowering. Thus, if expression is limited to the tapetum, male sterility may result in the same way as when TPP is expressed in the tapetum. It has also been shown that after GA application flower buds remain on the plant and some pollen is produced leading in some cases to seed production.

It has also been shown that simultaneous equimolar expression of trehalose phosphate synthase (TPS) and TPP gives no effect on plant physiology i.e. TPS counteracts the effect of TPP on carbohydrate metabolic and photosynthetic capacity of tissues in which they are expressed. It has also been shown that it is possible to restore fertility by retransforming sterile tobacco lines with a construct expressing TPS in the tapetun. Clearly, expression of TPS could also be put under control of an inducible promoter to allow fertility to be restored when desired, or optimising GA application could be an alternative means of restoring fertility. The promoter from a gene expressed specifically in the tissues surrounding or in, the ovule, such as the MADS box gene FBP7 could be used to drive expression of TPP or TreC to obtain female sterility. It is likely that some optimisation of codon usage may be required to obtain the same effect in a monocot crop plant such as wheat or corn, (Merlo and Folkerts), (Seed and Haas).

The use of a number of operator/repressor systems has been described as a means of controlling gene expression in plants. Wilde et al. demonstrated the use of the $E.$ $coli$ lac system to repress expression of GUS under the control of the maize cab promoter (lac I expression driven by 35S CaMV promoter). Operator sequences were inserted at various positions within the CAB promoter and the extent of repression assessed. Depending upon the position of the operator sequences, a range of repression was observed. When the operator sequence was incorporated by replacement between the TATA box and the transcription start, repression of ~90% was obtained. This repression can be relieved by the addition of IPTG. This was shown both in tobacco protoplasts and stable transformants.

Lehming et al. report that dramatic changes in binding affinity may be achieved by the modification of amino acids in the recognition helix of the lac repressor thus giving a tighter control of expression. Other such systems have been described and include the tetracycline inducible promoter system developed by Gatz et al (1991, 1992) in which a modified 35S CaMV promoter is repressed in plants expressing high levels of the tetracycline repressor protein but restored when tetracycline is added.

Steroid induction of protein activity can provide a chemically inducible expression system which does not suffer from chemical toxicity problems. Ligand binding domains of mammalian and insect steroid receptors such as glucocorticoid receptor (GR), oestrogen receptor can be used to regulate the activity of proteins in mammalian cells (Picard et al. 1993). A ligand binding domain fused to a protein maintains the protein in an inactive state until the ligand is introduced. Lloyd et al. (1994) describes a fusion of a maize transcriptional regulator with GR. Simon et al. (1996) describe a fusion of GR with an Arabidopsis flowering time gene product responsible for induction of transcription and Aoyama et al. (1995) describe a fusion of Ga14 or VP16 with a plant transactivating protein, Athb-1, placed under steroid control by means of the GR ligand-binding domain. It is known that the ability of transcriptional activators to bind to DNA and to simultaneously activate transcription is localised in defined domains of such transcription factors. It has been demonstrated (Ptashne 1988) and Mitchell and Tijan (1989) that transcriptional activator factors are made up of independently fìnctioning modules. Ptashne and Gann (1980) and others have shown that it is possible to combine a portion responsible for transcription activation of one factor with a DNA binding portion of another factor and the resulting hybrid protein be active in yeast cells. A system incorporating these components may be used to relieve repression and thus induce expression of genes in a controlled manner.

The use of juvenile hormone or one of its agonists as a chemical ligand to control gene expression in plants by receptor mediated transactivation has also been described.

Preferably, the switch system used to inducibly express the restorer gene is the AlcA/R switch system. We have demonstrated inducible expression of GUS in tomato anthers and pollen and have introduced similar constructs into wheat to demonstrate male and female tissue GUS expression using the AlcA/R switch system. We have also demonstrated inducible GUS expression in maize tassels, silks, embryo and endospermn using the safener inducible GST switch system (Jepson et al. 1994). Other switch systems may of course also be useful in the present invention.

The expression of cytotoxic or disrupter genes during plant transformation as a result of "leaky" expression from the male and female flower specific promoters at a very low level in tissues other than the target tissue may cause cell death and no recovery of transformants.

The inducible promoters used in the present invention to drive expression of the restorer genes may offer some protection against this possibility for the following reasons.

In the case of the GST-27 promoter, constitutive expression has been observed in callus. In the case of the AlcA promoter which is induced with ethanol, induction of GUS expression has been observed at concentrations of 7 ng/100 ml air. This concentration of ethanol can be added to the tissue culture medium to ensure expression of the restorer gene.

Examples of combinations of disrupter/restorer genes include barnase and barstar, and TPP and TPS.

The use of translational enhancer sequences, in particular the TMV Ω sequence (Gallie et al.) is preferred in the present invention to give an increase in expression levels from the constitutive tissue specific and inducible promoters such that the expression of the restorer gene e.g. barstar, is far in excess of that needed to inhibit the disrupter gene e.g. barnase being produced. Gallie et al. showed that the translation of prokaryotic and eucaryotic mRNA's is greatly enhanced by a contiguous derivative of the 68 nucleotide, 5' leader sequence of tobacco mosaic virus U1 strain called Ω. Several other viral leader sequences have also been shown to enhance expression, such as alfalfa mosaic virus (A1MV) and broom mosaic virus (BMV). In tobacco mesophyll protoplasts an enhancement of ~20 fold was observed. Other enhancer sequences e.g. tobacco etch virus may also be used in the present invention.

In addition, the use of intron sequences to enhance expression levels is well documented. Among those studied are the maize adh 1 intron 1 sequence which has been shown to increase levels of expression 12–20 fold when inserted in 5' translated sequences in chimeric constructs introduced into maize protoplasts (Mascarenhas et al. 1990) and the Sh 1 intron also from maize. The inclusion of this intron into constructs in which the CaMV35S promoter was driving CAT expression resulted in increases of between 11 and 90 fold. (Vasil et al 1989).

Expression levels of the restorer and disrupter genes can also be balanced or modulated in the following ways. A promoter giving high levels of expression could be used to drive expression of the restorer gene while a promoter giving lower levels of expression could be used to drive expression of the disrupter gene. This would ensure that the disrupter gene product is swamped by restorer gene product thereby inactivating all cytotoxic or disrupter molecules allowing full restoration of fertility. A further way of modulating expression levels could be carried out by using mutagenesis to change the sequence around the AUG initiation codon in such a way that expression of the disrupter gene is non-optimal (Kozak (1989)) and is therefore down-regulated.

The expression systems of the present invention can be introduced into a plant or plant cell via any of the available methods such as Agrobacterium transformation, electroporation, microinjection of plant cells and protoplasts, microprojectile bombardment, bacterial bombardment, particularly the "fibre" or "whisker" method, depending upon the particular plant species being transformed. The transformned cells may then in suitable cases be regenerated into whole plants in which the new nuclear material is stably incorporated into the genome. Both transformed monocot and dicot plants may be obtained in this way. Reference may be made to the literature for full details of the known methods.

Christou and Heie (1997) describe the transformation of rice using bombardment methodology and progress on rice transformation mediated by *Agrobacterium tumefaciens*.

Other published methods for transforming wheat include Becker et al (1994) which describes the use of microprojectile bombardment of scutellar tissue and Vasil et al (1993) which describes the rapid generation of transgenic wheat following direct bombardment of immature embryos. FIG. 22 describes timelines for wheat transformation by bombardment.

The use of a selectable marker is required in the transformation process to select transformants carrying the sterility constructs. This could be an antibiotic selectable marker or a herbicide resistance gene. The use of a herbicide resistance gene or other marker is not essential (but may be considered to be convenient) to the process of hybrid seed production.

The hemizygous plants used in the second method of the present invention can be treated with chemical to induce the expression of the restorer genes which allows self pollination to occur. The progeny of this self pollination will be segregating and can be grown up, treated with chemical and self pollinated. The progeny from homozygous lines will not segregate for sterility. A repeat of the process may then be performed to bulk up homozygous sterile seed.

The individual components of the expression cassette of the present invention may be provided on one or more individual vectors. These can be used to transform or co-transform plant cells so as to allow the appropriate interaction between the elements to take place.

The present invention will now be described only by way of examples in which reference shall be made to the accompanying Figures:

BRIEF DESCRIPTION OF THE DRAWINGS

FIG. 1 shows a schematic representation of expression cassettes used in a first method of hybrid seed production using a homozygous recessive male sterile female parent.

FIGS. 2a and 2b show the generation of F1 hybrid seed from a homozygous recessive male sterile female parent and a female sterile male parent according to the first method of the present invention and the segregation in the F2 generation.

FIG. 3 shows a schematic representation of expression cassettes used in a second hybrid seed production process.

FIG. 4 shows a schematic representation of an expression cassette used in the production of a male sterile female fertile parent plant using a male flower specific promoter and a female tissue specific promoter.

FIG. 5 shows a schematic representation of an expression cassette used in the production of a female sterile male parent plant using a male flower specific promoter and a female flower specific promoter.

FIGS. 6a, 6b and 6c show the generation of F1 hybrid plants using a male sterile female parent plant and a female sterile male parent plant, both under the control of sporophytic promoters, according to the second method of the present invention, the generation of the F1 hybrid seed and the segregation of the F2 progeny.

FIGS. 7a, 7b and 7c show the generation of F1 hybrid plants using a male sterile female parent plant and a female sterile male parent plant, male sterility being under the control of a gametophytic promoter and female sterility being under the control of a sporophytic promoter, according to the second method of the present invention, the generation of F1 hybrid seed and the segregation of the F2 progeny.

FIG. 11 shows GST expression in various maize tissues by northern analysis.

FIG. 29 shows Stig1AlcR-AlcAGluGUSIntnos.

FIG. 31 shows pMOG1006-C5-GUS, a rice transformation vector.

FIG. 61 shows the DNA sequence (SEQ ID NO: 29) encoding the ZmC5 promoter sequence in maize.

Figure 8:
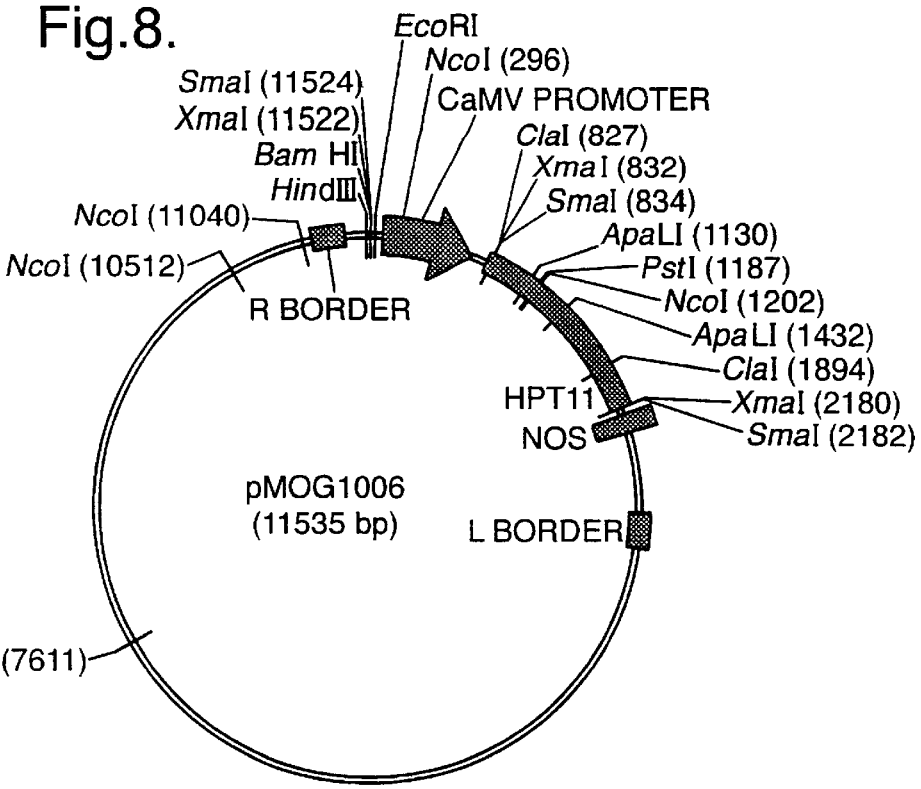
FIG. 8 shows the binary plant transformation vector pMOG1006.

The underlined A is the putative transcriptional start point and the bold and underlined ATG is the translational start point.

DETAILED DESCRIPTION OF THE INVENTION

EXAMPLE 1

In this example, the male parent plant is male fertile and homozygous female sterile as a result of a natural or engineered mutation. The female parent plant is homozygous recessive male sterile and female fertile. The male sterility can be genetically manipulated or introduced by crossing or be due to a natural mutation. For example, it could be due to a mutation in a gene such as MS45 which has been shown to act in a recessive manner, leading only to sterility when homozygous.

The parental lines also contain a DNA sequence encoding an inducible promoter operably linked to a functional copy of the sterility gene thus restoring fertility for the purpose of maintenance of the female and male parental lines, respectively (see FIG. 1).

Crossing these two parent plants generates F1 hybrids which are heterozygous for the recessive male sterility and female sterility alleles and are therefore fully fertile. If, however, the farmer harvests and grows the F1 seed, the F2 generation segregates for sterility leading to a loss of heterosis and yield as approximately 25% female plants are sterile (see FIGS. 2a, 2b and 2c).

Although female recessive mutations are known in corn, the genes have not yet been cloned.

EXAMPLE 2

A second method of producing hybrid seed has been formulated based on sterility brought about entirely by genetic manipulation (see FIG. 3).

FEMALE PARENT

The female parent is a male sterile line i.e. an inactivating gene is expressed by a male sporophytic promoter thereby preventing the production of viable fuictional pollen. In addition, a restorer gene is expressed in the female tissues. Self fertility may be restored by means of an inducible promoter linked to a restorer gene. Transformation with such an expression cassette (see FIG. 4) leads to hemizygous plants MS $R^F$ $R^{CS}$----------.

$R^{cs}$=chemically restorable male and female fertility
MS=dominant male sterility
$R^M$=dominant male fertility restorer
FS=dominant female sterility
$R^F$=dominant female fertility restorer To obtain homozygous plants for use in hybrid seed production, the hemizygous plants must be induced with an exogenous chemical inducer, such as ethanol in the case of the AlcA/R gene switch, and allowed to self-pollinate.

| Gametes | MS $R^F$ $R^{CS}$ | ---------- |
|---|---|---|
| MS $R^F$ $R^{CS}$ | MS $R^F$ $R^{CS}$ | ---------- |
|  | MS $R^F$ $R^{CS}$ | MS $R^F$ $R^{CS}$ |
| ---------- | ---------- |  |
|  | MS $R^F$ $R^{CS}$ |  |

Three quarters of the plants produce 100% sterile pollen as the sterility gene has a dominant effect, only the null line is male fertile. The homozygous plant can be distinguished from the heterozygous plants by growing up the seed resulting from self-pollination to repeat the induction and self-pollination procedure. The progeny of these will segregate for sterility and can be easily scored, depending on the genotype, as described earlier. Herbicide resistance or other selectable marker gene could also be used to score. In the case of the homozygous plant all progeny will be male sterile (and herbicide resistant,) in the case of the heterozygous, the progeny will continue to segregate for sterility.

Thus, the homozygous male sterile, homozygous female fertile line can be selected in this way.

MALE PARENT

The male parent plant is fully male fertile but is female sterile i.e. homozygous female sterile, male fertile. In this case, the female sterility is brought about by expressing, in the female floral organs, an inhibitory gene which is deleterious to female floral organ development as defined earlier. Alternatively, the pollen tube may be destroyed or the plant may otherwise be prevented from developing the seed. A restorer gene is also expressed in the male floral tissues.

The male parent plant is obtained in the same way as the female parent plant but using the construct shown in FIG. 5. In this case, the hemizygous plants havethe genotype:

FS $R^M$ $R^{CS}$---------- and the homozygous plants will have the genotype

FS FS $R^M$ $R^M$ $R^{CS}$ $R^{CS}$

EXAMPLE 3

In this example, the expression cassette comprises a gametophytic (e.g. pollen specific) promoter (see FIG. 5).

The male parent plant is as described in Example 2 above. Examples of pollen specific promoters include Zm13 (Hanson et a.) and C5, deposited at The National Collection of Industrial and Marine Bacteria as NCIMB 40915 on Jan. 26, 1998. The C5 promoter sequence is shown in FIG. 61. Once again the homozygous male sterile line must be obtained and the hemizygous plants are chemically treated and self-pollinated.

| Gametes | MS $R^F$ $R^{CS}$ | ---------- |
|---|---|---|
| MS $R^F$ $R^{CS}$ | MS $R^F$ $R^{CS}$ | MS $R^F$ $R^{CS}$ |
|  | MS $R^F$ $R^{CS}$ | ---------- |
| ---------- | MS $R^F$ $R^{CS}$ | ---------- |
|  | ---------- | ---------- |

In this case, the homozygous line i.e. MS MS $R^F$ $R^F$ $R^{CS}$ $R^{CS}$ produces 100% sterile pollen which can be identified by DAPI staining. This can be distinguished from pollen from a heterozygous plant which produces 50% sterile and 50% fertile pollen which is also identifiable by DAPI staining.

Thus, the MS MS $R^F$ $R^F$ $R^{CS}$ $R^{CS}$ line can be selected.

It can therefore be seen that neither male or female homozygous parent can self-pollinate.

The female parent plant in Examples 2 and 3 carries an expression cassette comprising a female specific promoter driving the expression of a restorer gene, and the male parent plant carries an expression cassette comprising a male specific promoter driving the expression of a restorer gene. In the parent plants, these expression cassettes have no effect on fertility due to the specificity of the promoters.

When these two parent lines are crossed, however, the result depends on whether a gametophytic (e.g. pollen specific) or a sporophytic (e.g. tapetum specific) promoter has been used to produce male sterility in the female parent. When a sporophytic promoter is used full restoration of fertility is achieved and the F1 seed is fully fertile i.e. produces approximately 100% fertile pollen (see FIGS. 6a, 6b). If, however, F1 seed is retained and grown by the farmer, the sterility segregates as above (see FIG. 6c). If a gametophytic promoter is used to obtain male sterility, full restoration of fertility is not achieved as pollen is haploid and only about 50% of pollen will inherit the functional allele producing pollen fertility (see FIGS. 7a, 7b). The F2 progeny segregate as described previously (FIG. 7c).

Maintenance of the homozygous sterile lines is achieved, when required, by the third component of the system. Each parental line comprises, therefore, an inducible promoter, optionally linked to an enhancer sequence or one or more intron sequences, driving the expression of the restorer in all tissues on application of the inducing chemical, thus allowing pollen production in the female parent and normal ovule and tissue development in the, male parent. Self-pollination can then occur allowing bulking up of parental seed.

In all Examples, the application of chemicals in the field is necessary only to produce seed of the parental lines which needs to be done infrequently and on a relatively small acreage.

In the described Examples, it is possible to use a tapetum specific (FIGS. 6a, 6b or 6c) or a pollen specific promoter (FIGS. 7a, 7b) to drive the expression of the inactivating gene. The use of a tapetum specific promoter is preferred as fertility can be fully restored. However, as pollen is haploid, full restoration of fertility is not possible where a pollen specific promoter is used. There may, however, be advantages to using a pollen specific promoter. For instance, pollen specific promoters may have greater tissue specificity. Chemical treatment of the plants is only necessary to restore fertility to allow self-pollination.

EXAMPLE 4

PREPARATION OF GENERAL CLONING VECTORS

All molecular biology techniques were performed either as described by Maniatis et al., Molecular Cloning: A Laboratory Manual second edition (1989) Cold Spring Harbour Laboratory Press: Vols I and II (D. N. Glover ed 1985) or as recommended by the named manufacturers.

Preparation of pMOG1006-Fse pMOG1006 (FIG. 8) is a binary vector which carries a hygromycin resistance gene as selectable marker and is used for Agrobacterium mediated transformation of rice. The modified vector was prepared by digesting pMOG1006 with EcoRI and inserting an annealed pair of complementary oligonucleotide having the sequences (SEQ ID NOS: 1–2):

Link1A AAT TGA TCG GCC GGC CCT AG

Figure 9:
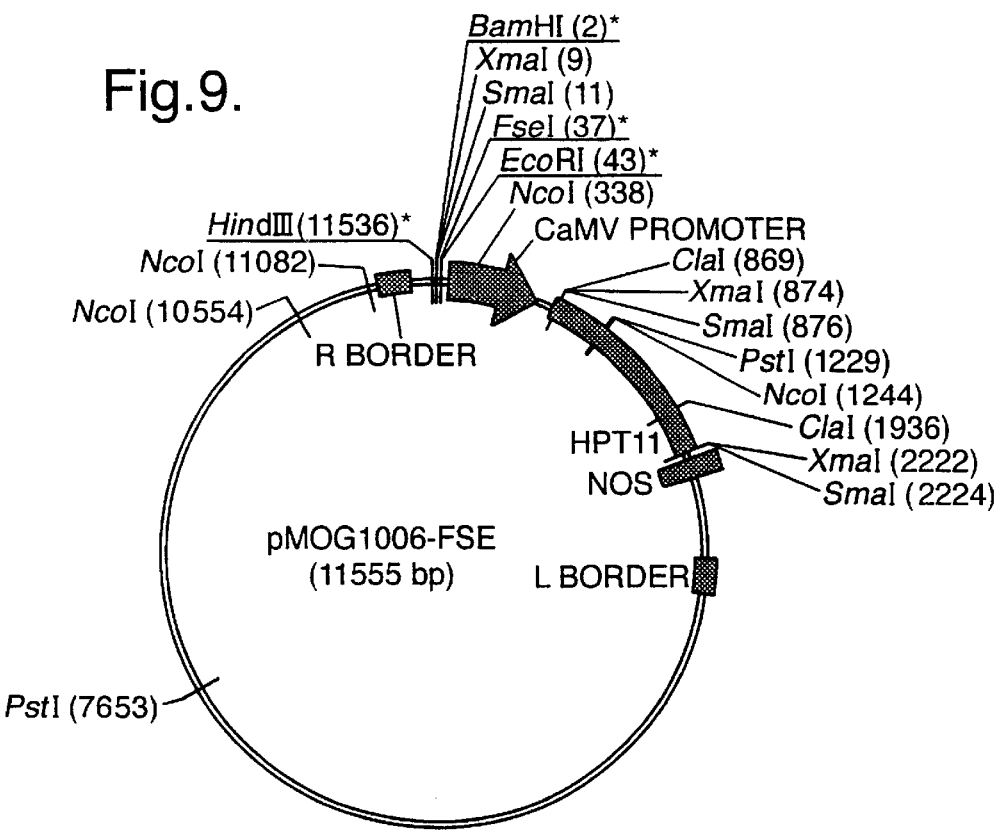
FIG. 9 shows the binary plant transformation vector pMOG1006-FSE.

Link1B AAT TCT AGG GCC GGC CGA TC which introduces a unique FseI site. Clones containing the correct oligonucleotide sequence were selected by hybridisation with link1A oligonucleotide labelled with $\gamma^{32}P$ and clones containing the sequence in the desired orientation selected after characterisation by sequencing (FIG. 9).

pVB6 pVB[6] is analogous to the binary vector described above in that it contains a unique Fse1 site but carries the npt11 selectable marker and is used in Agrobacterium mediated tobacco transformation.

Figure 10:
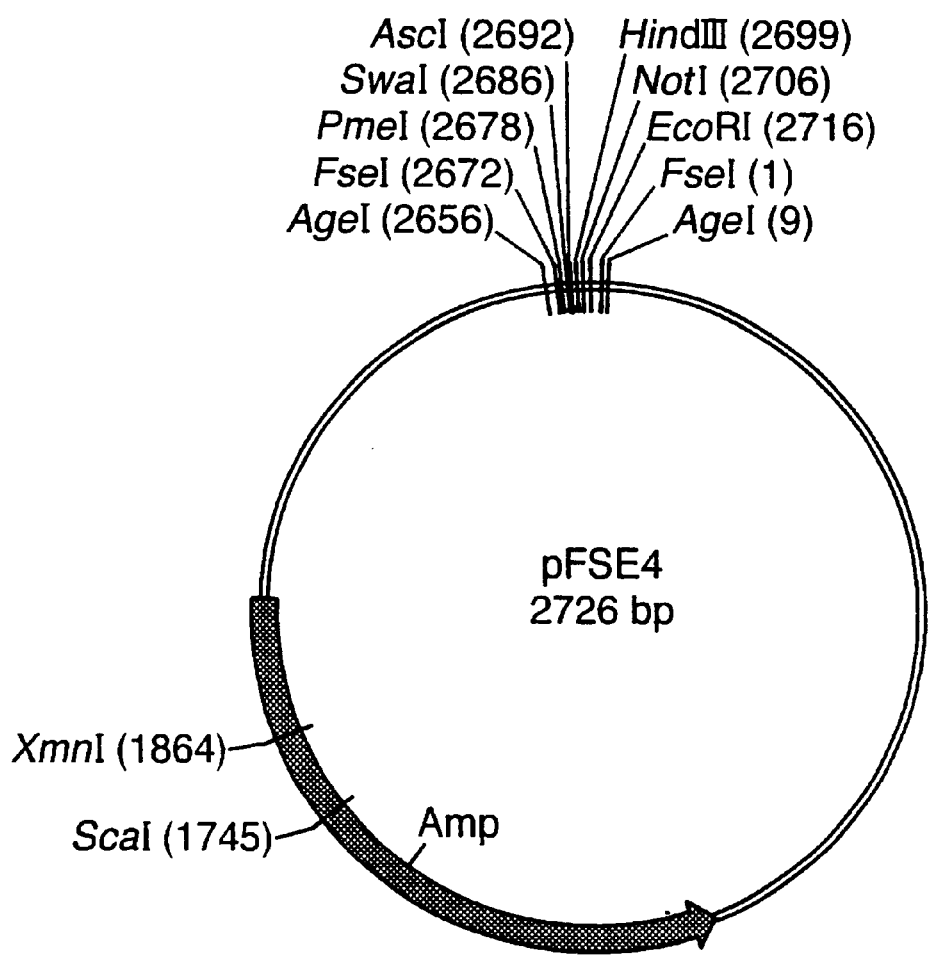
FIG. 10 shows the cloning vector pFSE4.

Preparation of DFse4 (FIG. 10)

This vector was constructed to allow the assembly of vectors containing a number of expression cassettes. This was achieved by using rare 8-base recognition restriction enzyme sites in the multiple cloning site region. The pFSE (FIG. 32) DNA was digested with FseI and the existing multiple cloning region removed. Complementary oligonucleotide having the sequences (SEQ ID NOS: 3–4):

DAA-1A:

5' CCGTTTAAACATTTAAATGGCGCGCCAA GCTTGCGGCCGCCGGGAATTCGGCCGG-3'

DAA-1S: 5' CCGAATTCCCGGCGGCCGCAAGCT-TGG CGCGCCATTTAAATGTTTAAACGGCCGG-3' were inserted. This sequence introduces a unique EcoRI, NotI, HindIII, AscI, SwaI and a PmeI site flanked by FseI sites. Expression cassettes were assembled in pSK+ and linkers inserted to flank each cassette with unique sites as described below. Whole cassettes were then inserted pFSE4 as required. Multiple cassettes could then be removed as an FseI fragment to the pMOG1006-FseI and VB6 vectors described above. were inserted. This sequence introduces a unique EcoRI, NotI, HindIII, AscI, SwaI and a PmeI site flanked by FseI sites. Expression cassettes were assembled in pSK+ and linkers inserted to flank each cassette with unique sites as described below. Whole cassettes were then inserted into pFSE4 as required.

Multiple cassettes could then be removed as an FseI fragment to the pMOG1006-Fse1 and VB6 vectors described above.

EXAMPLE 5

PCR CLONING OF THE STIGI PROMOTER FROM TOBACCO

A 1.6 kb fragment was PCR-amplified from 10 ng tobacco genomic DNA using Stratagene's PfuTurbo DNA polymerase and oligonucleotides (SEQ ID NOS: 5–6) ST1-L2 (5'-ATTCGACCTCGCCCCCGAGCTGTATATG-3') and ST1-R2 (5'-GATGAGAATGAGAAGGTTGATA AAAGCC-3'). Thermocycling conditions were as follows: 95° C. for 3 minutes, followed by 35 cycles of 95° C. for 1 minute, 50° C. for 1 minute, 72° C. for 4 minutes, followed by a final incubation at 72° C. for 5 minutes. A 1.6 kb amplification product was gel-purified using QIAGEN's QIAquick Gel Extraction Kit and ligated into Invitrogen's pCR-ZERO Blunt vector. The DNA sequence of the insert was determined, and exhibited 100% identity with the published STIG1 sequence (Goldman et al 1994). The insert was then transferred, on a SacI-NotI fragment, into pBluescript SK+ for further manipulation (pSK-STIG1).

EXAMPLE 6

PREPARATION OF PLANT TRANSFORMATION VECTORS TO TEST EXPRESSION FROM CHEMICALLY INDUCIBLE PROMOTERS

GST-GUS

Figure 12:
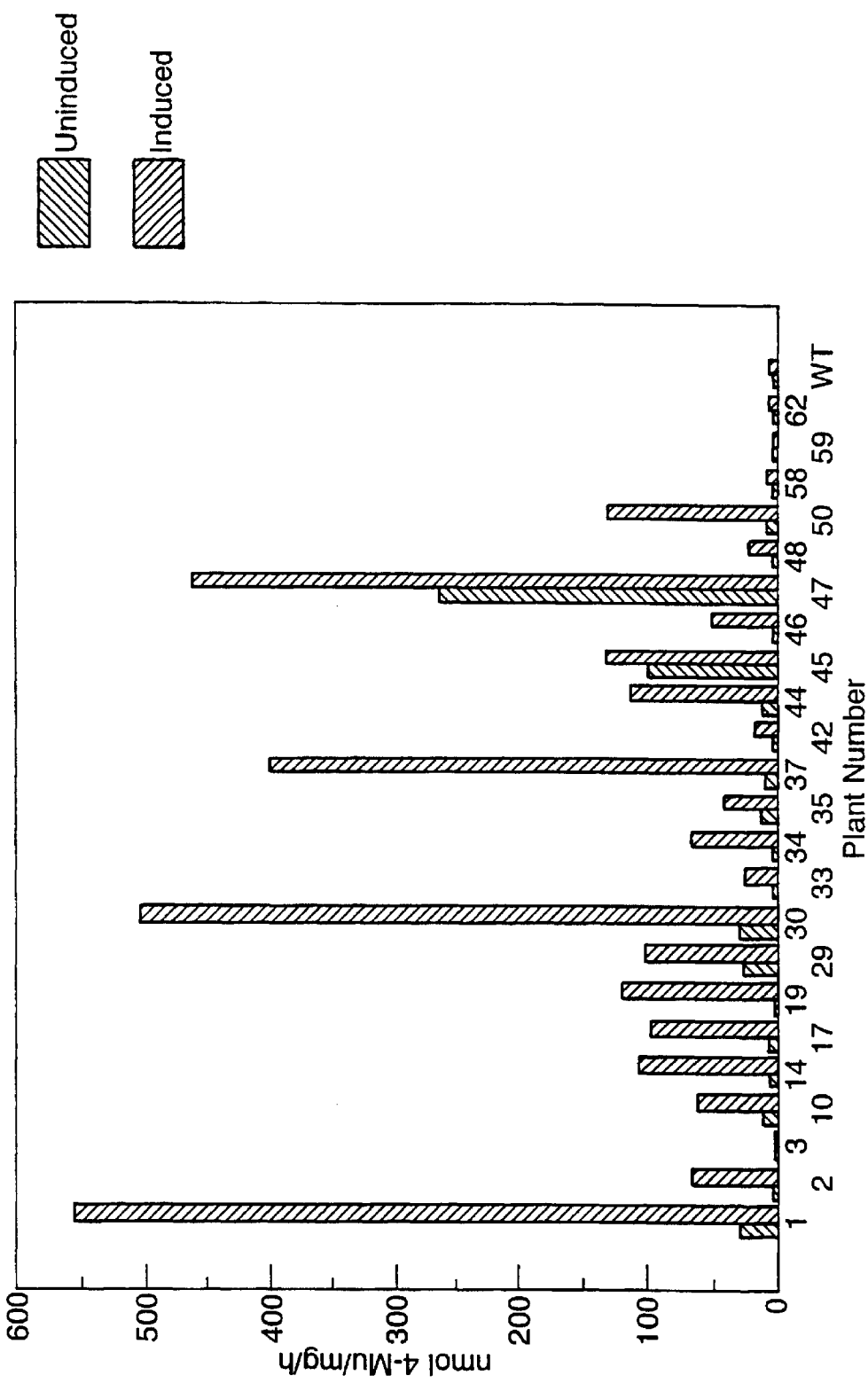
FIG. 12 shows inducible expression of the GUS reporter gene in tobacco leaf by the GST promoter.
Figure 13:
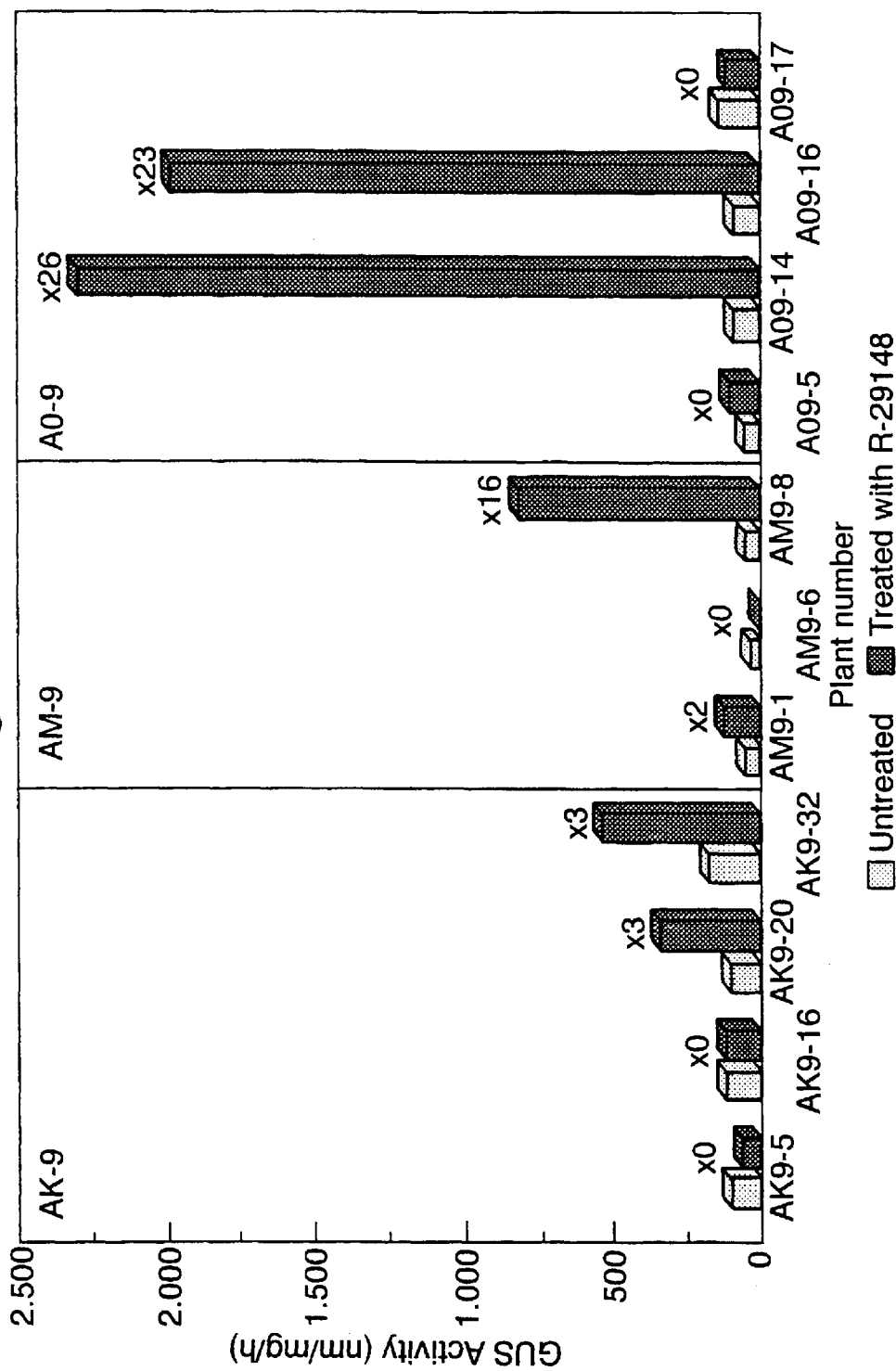
FIG. 13 shows inducible expression of the GUS reporter gene in corn leaf by the GST promoter.
Figure 14:
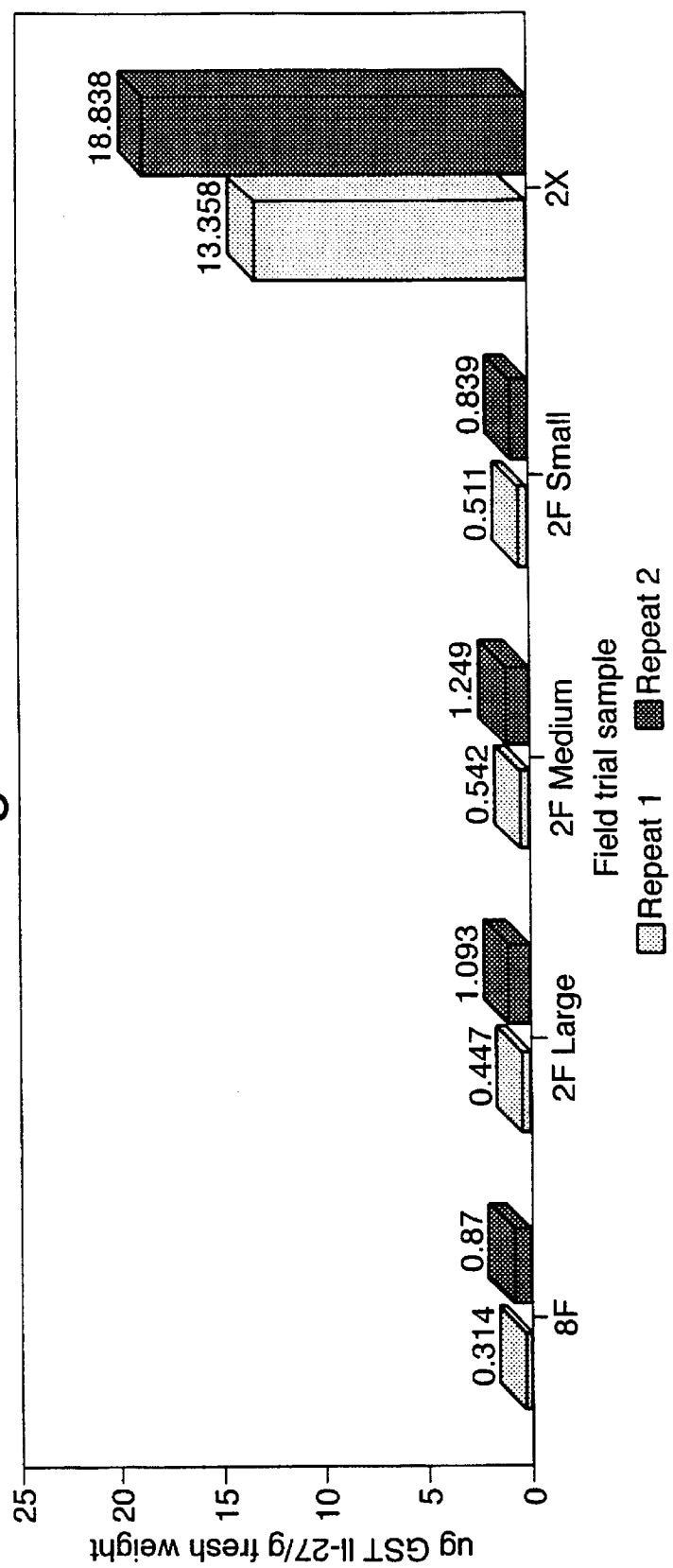
FIG. 14 shows inducible expression of the GUS reporter gene in corn tassels by the GST promoter.
Figure 15:
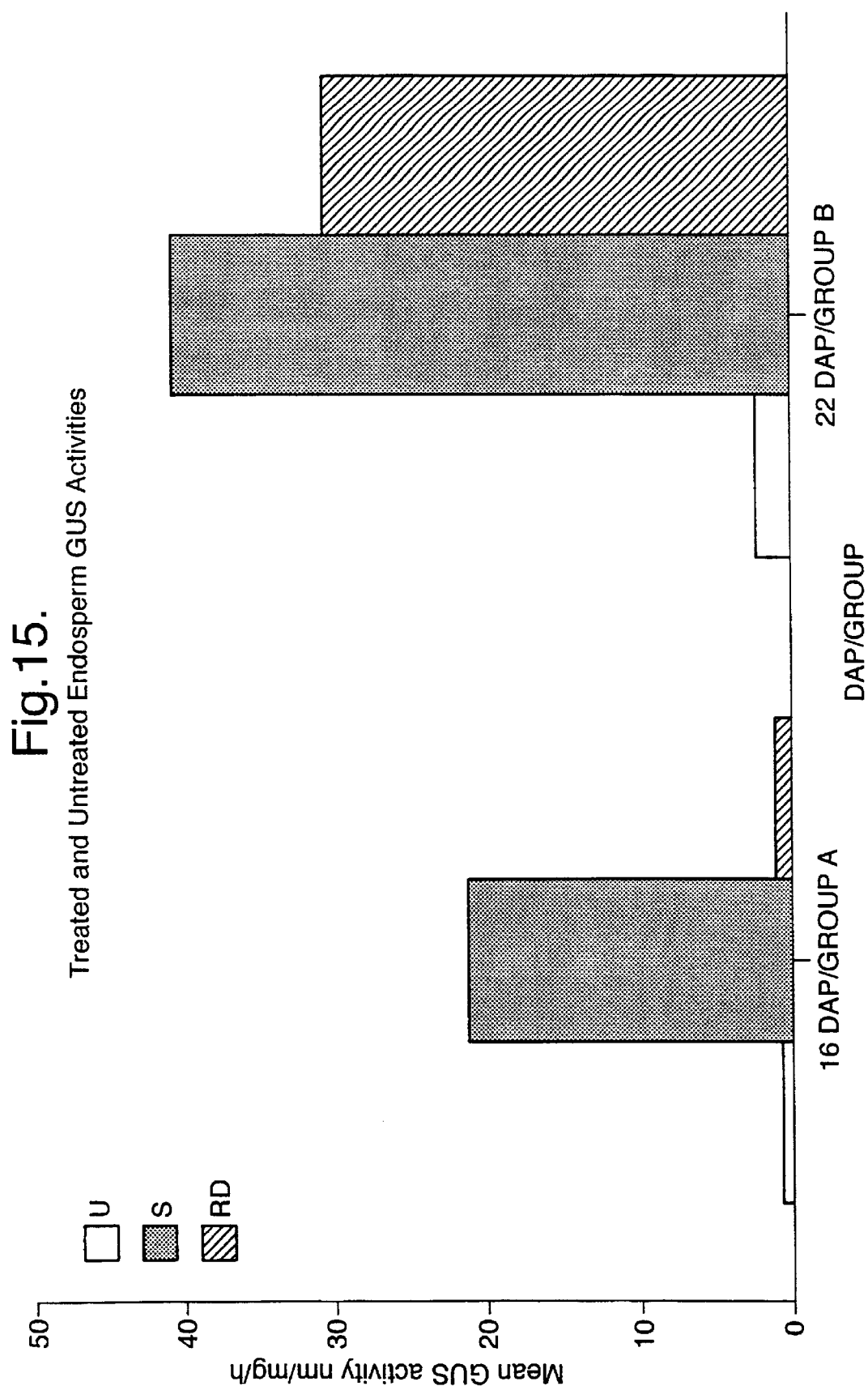
FIG. 15 shows inducible expression of the GUS reporter gene in corn endosperm.
Figure 16:
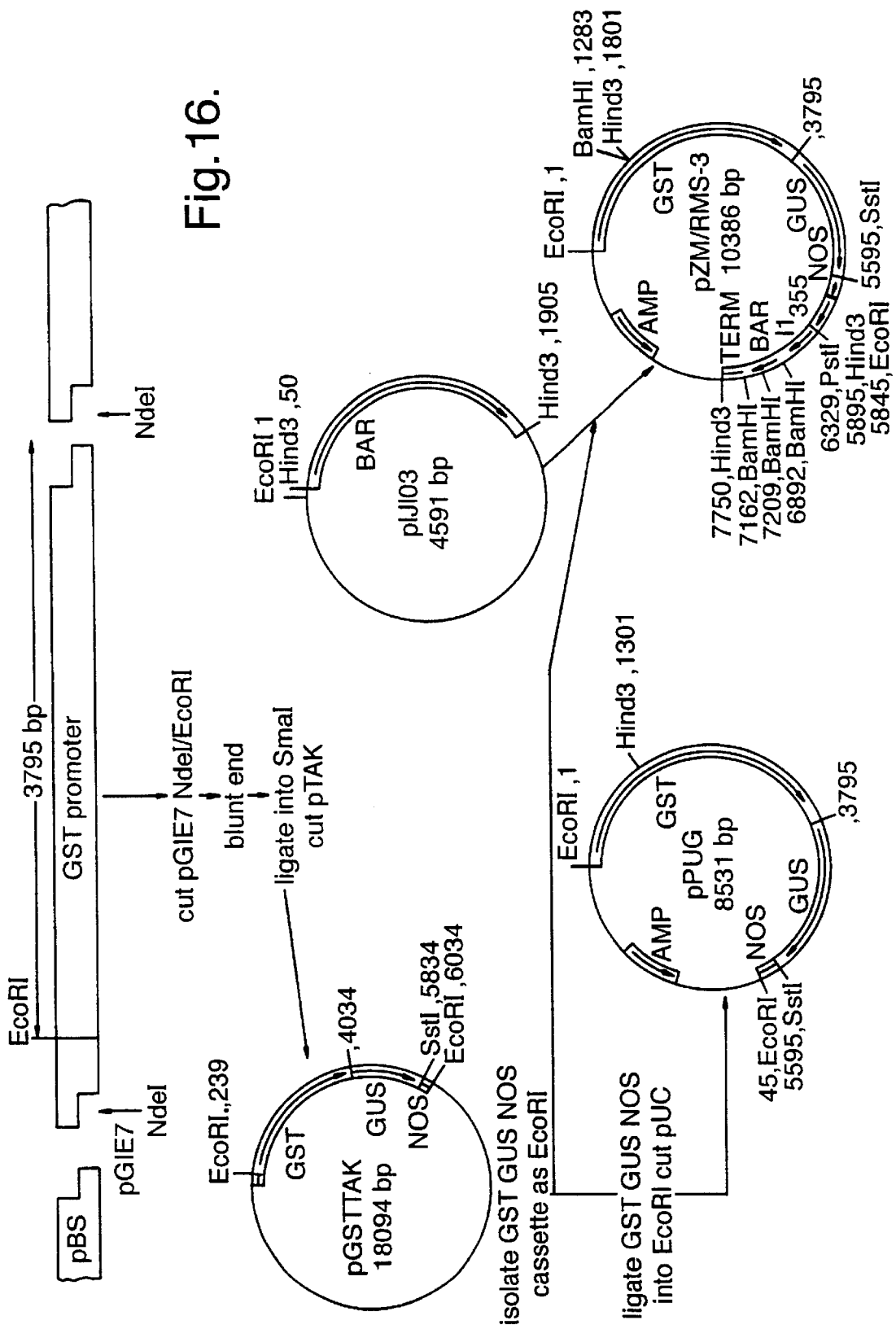
FIG. 16 shows the pPUG and RMS-3 cloning strategies.
Figure 17:
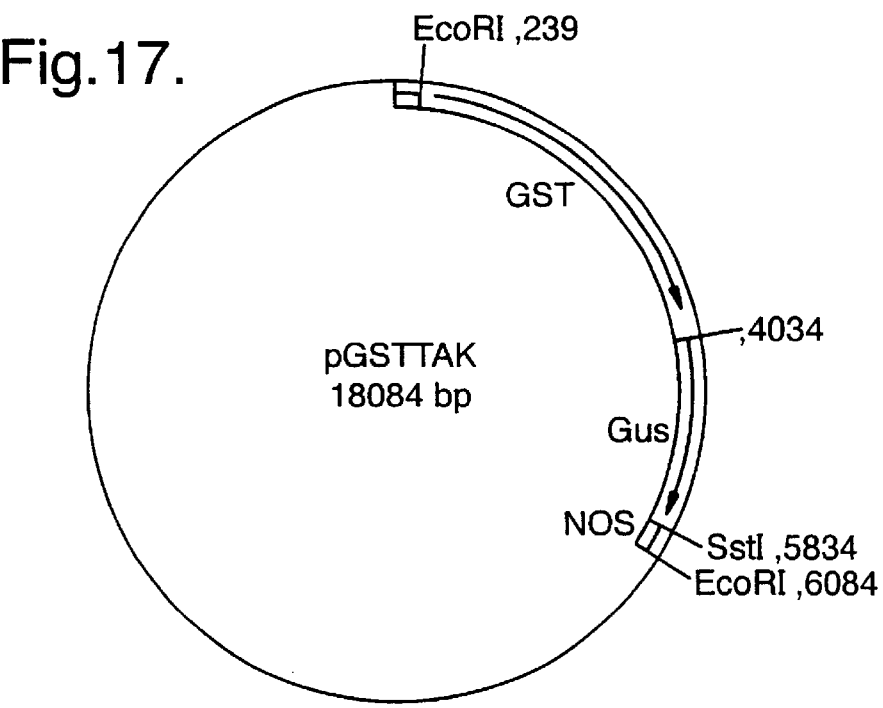
FIG. 17 shows the pGSTTAK vector.
Figure 18:
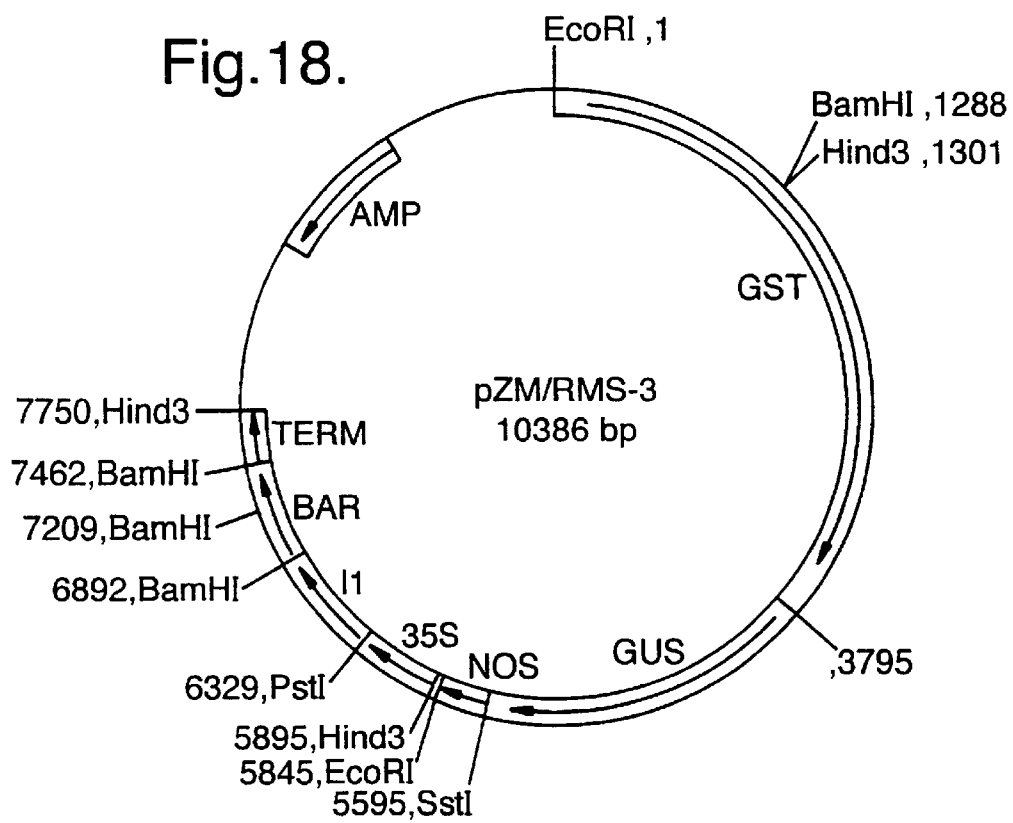
FIG. 18 shows RMS-3 vector.

The characterisation of the maize GST27 cDNA has been previously reported and experiments have shown that GST 27 is not constitutively expressed in silks, leaf, embryo or endosperm. After safener application, expression was detected in all of these tissues (see FIGS. 11 to 15). Plant transformation constructs utilising the GST 27 promoter to drive the expression of GUS may be made as described in U.S. Pat. No. 5,589,614 (FIG. 16). These are pGSTTAK (FIG. 17) for tobacco transformation and RMS-3 (FIG. 18) for corn transformation. These vectors could be used to generate stable tobacco and maize transforrnants. Formulated safener may be applied as either a leaf paint (tobacco) or as a root drench (corn) as described in the aforementioned patent and expression of GUS observed. The results for induction of GUS expression in tobacco leaves are shown in FIG. 12; clear induction of expression has occurred up to 100×. Similarly, for corn there has been an induction of GUS expression in leaf after safener treatment. Induction of expression was also observed in tassels and endosperm tissue and embryo.

RMS-3 was also used to transform wheat, and the induction of GUS expression was studied. Modified vectors using hygromycin as a selectable marker could be introduced into rice.

GST-Barstar

The corn transformation vector Zm/RMS14 (described above) carries a barstar gene fused to the safener induced GST-27 promoter. WU25 was shown by PCR to contain this gene fusion. Reversal of sterility was demonstrated by application by root drench of safener R-29148 to glass house grown plants. Treated plants showed increased tassel size relative to untreated plants. There was no effect of the safener on the size or fertility of tassels on non-transgenic fertile plants. Correlated with increase in tassel size, microspore development was observed in anther samples taken from root drenched samples in the glass house. A similar effect was seen after a foliar application to field grown plants, but not in untreated plants in any experiment. The resumption of microspore development appears to be linked to the barstar inhibition of barnase thus overcoming the ablation of tapetal cells. On plants exposed to extended treatment with safener, microsporogenesis had proceeded resulting in anthers filled with immature post-mitotic pollen. In contrast, the anthers from sterile plants were collapsed.

pSRNAGS

Figure 19:
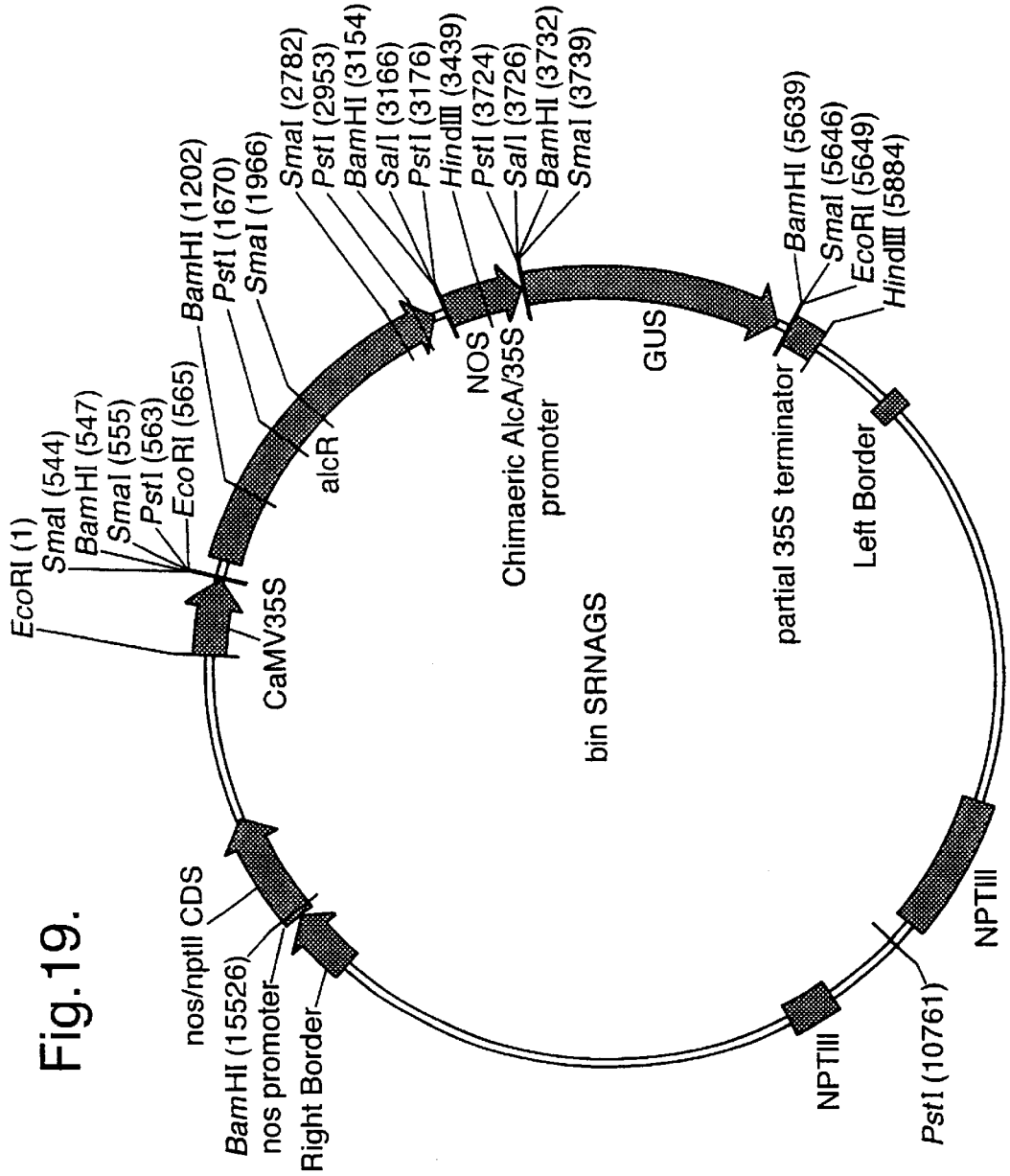
FIG. 19 shows the map of pSRN.AGS, an inducible GUS expression vector for use in dicot species.
Figure 20:
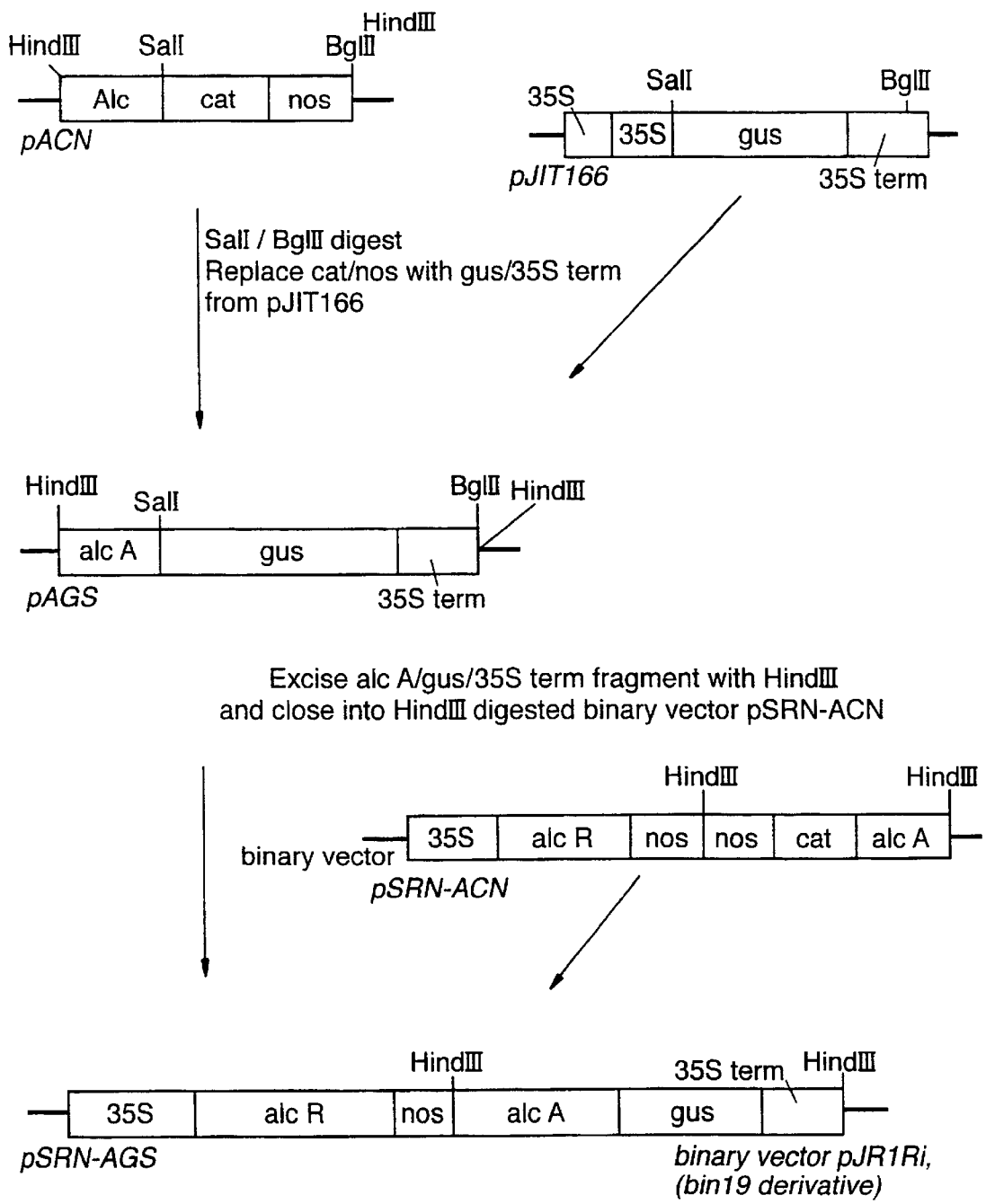
FIG. 20 shows the cloning strategy for pSRN.AGS, an inducible GUS expression vector for use in dicot species.

A binary plant transformation vector, pSRNAGS (FIG. 19) was constructed according to the strategy described in FIG. 20. This vector comprises the chimeric 35S-AlcA promoter driving the expression of GUS and the 35S CaMV promoter driving the expression of the AlcR gene.

pUIRN.AGS

Figure 21:
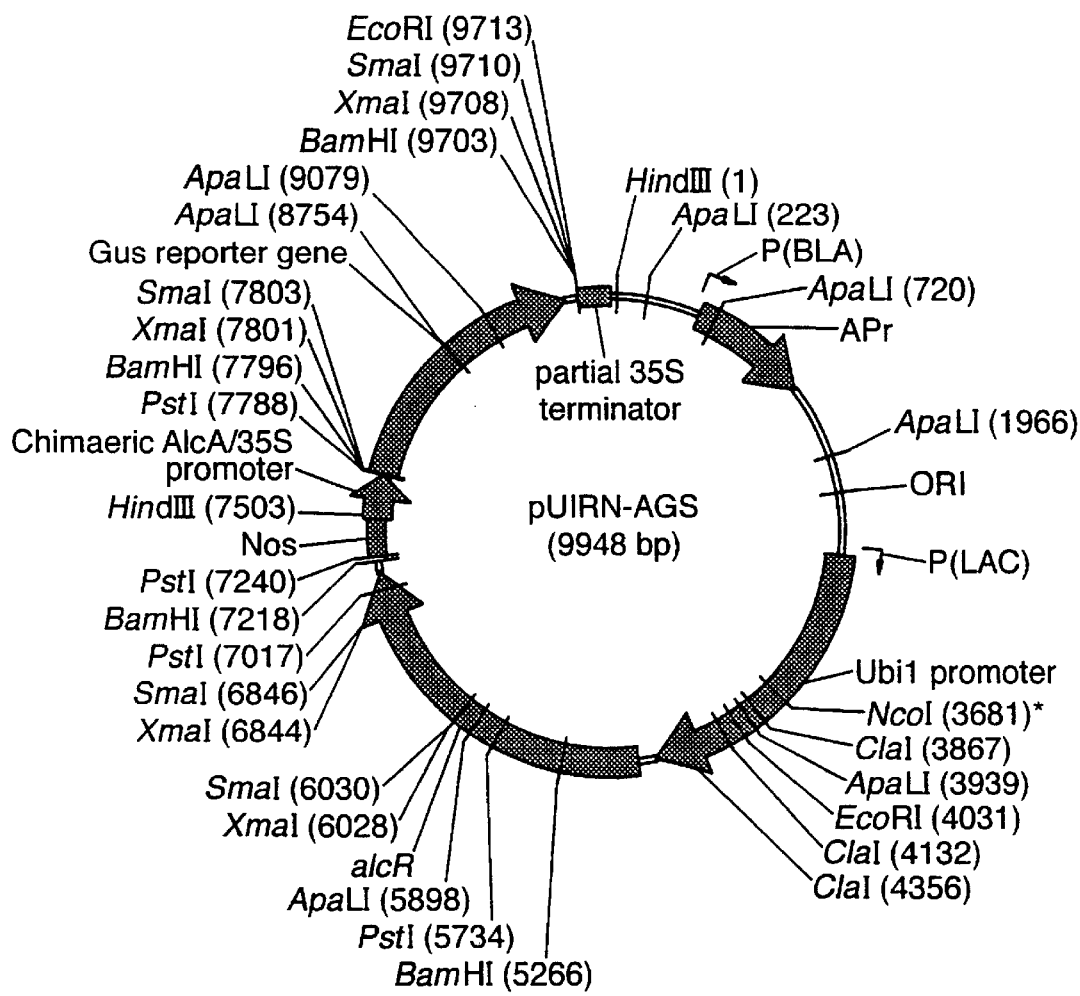
FIG. 21 shows the map of pUIRN.AGS, an inducible GUS expression vector for use in monocot species.
Figure 22:
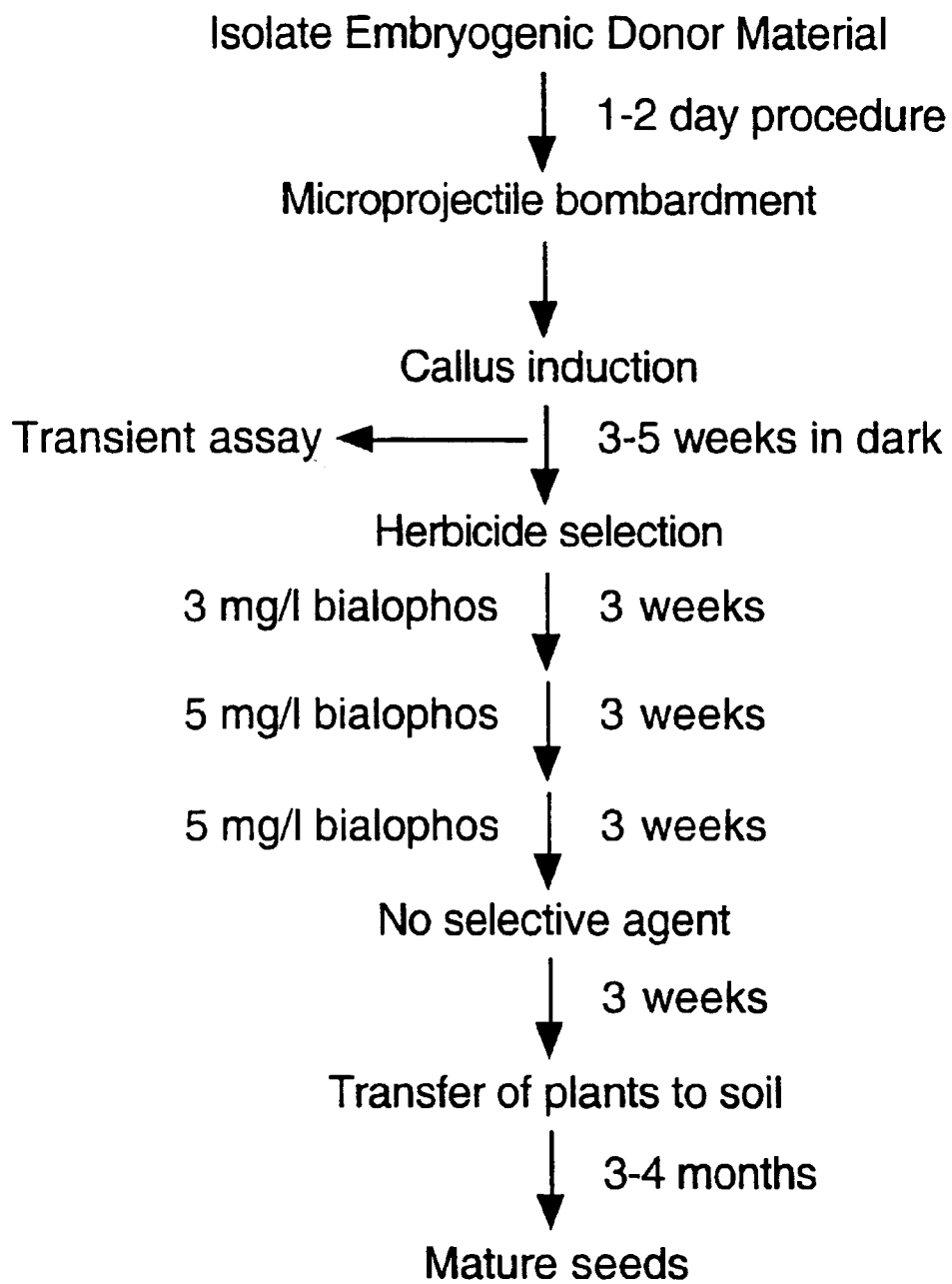
FIG. 22 shows timelines for wheat transformation by bombardment.

A pUC based vector for use in transforming corn and wheat was prepared in which the ubiquitin promoter linked to the ubiquitin intron was used to drive expression of the AlcR gene (FIG. 21). The time lines for obtaining transgenic wheat are shown in FIG. 22.

pMOG1006-SRNAGS (Rice)

Figure 23:
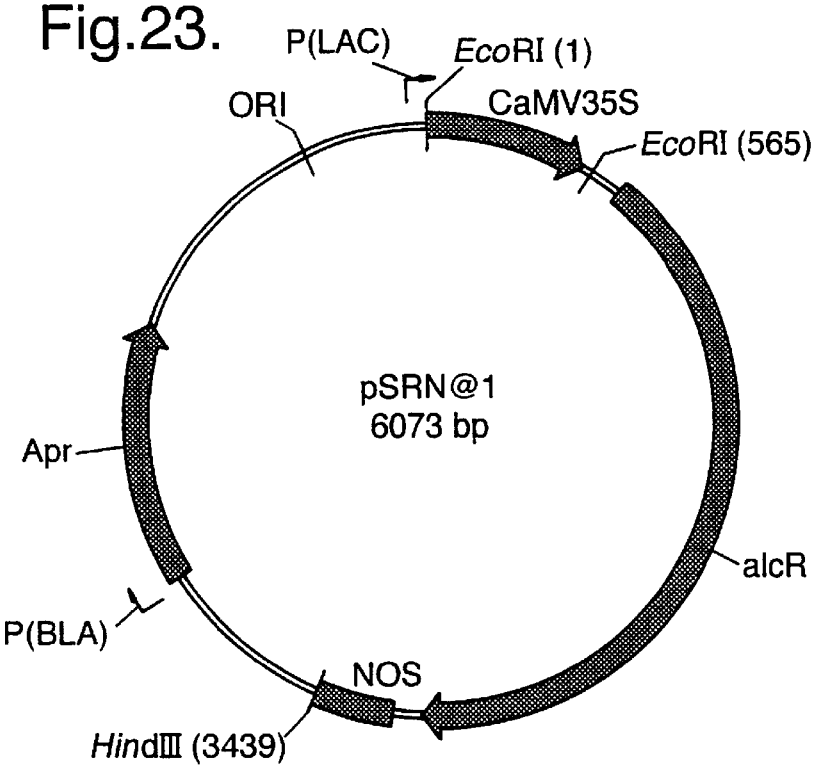
FIG. 23 shows map of pSRN.
Figure 24:
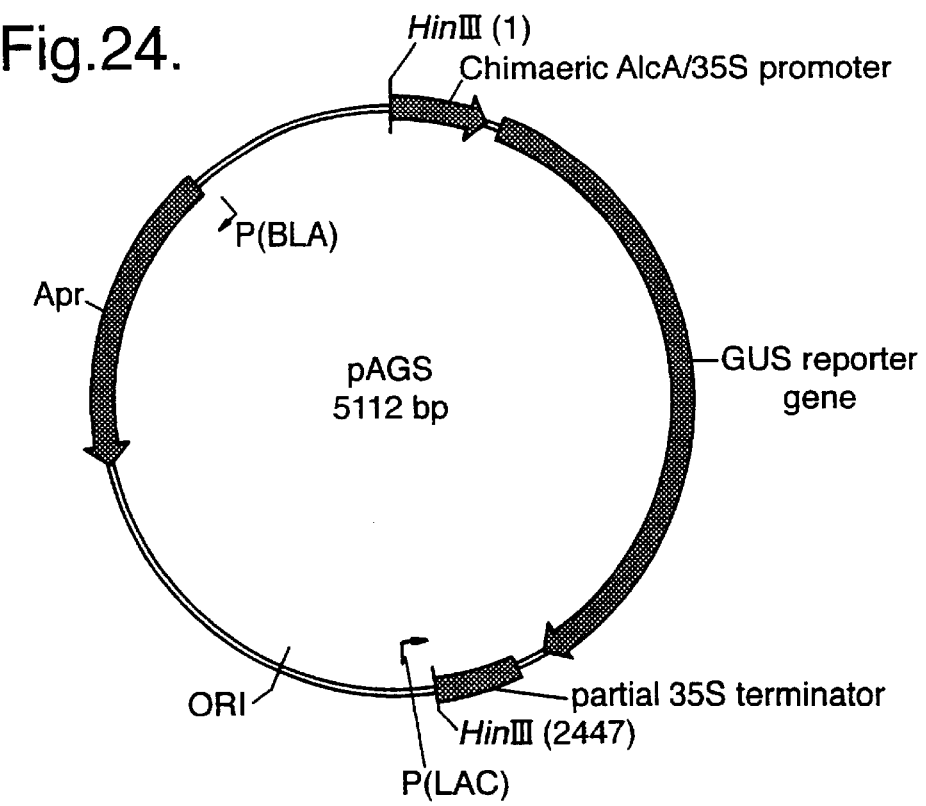
FIG. 24 shows map of pAGS.
Figure 25:
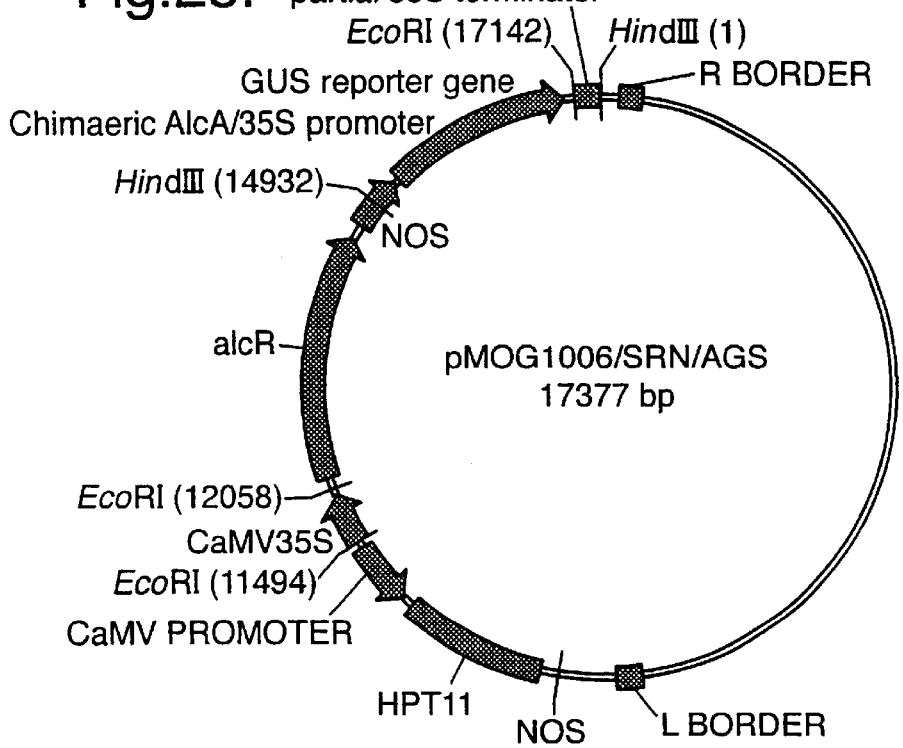
FIG. 25 shows map of pMOG1006-SRN.AGS, a rice transformation vector.

The plasmid pSRN (FIG. 23) was digested with EcoRI and HindIII to release a 2.6 kb fragment (AlcR-nos) which was cloned as an EcoRI-HindI fragment into pMOG1006. The 560 bp CaMV 35S promoter fragment was then cloned into the EcoRI site to produce 35S-AlcR-nos, clones in the desired orientation were selected by sequence analysis (pSRN). The plasmid pAGS (FIG. 24) was digested with HindIII and a 2.5 kb fragment (AlcA-GUS-nos) was cloned into the HindIII site of pMOG 1006-SRN to produce the final construct called pMOG1006-SRN-AGS (FIG. 25). The orientation of the HindIII fragment was determined by restriction and sequence analysis.

In order to optimise levels of expression of AlcR in the tapetum, pistil, pollen and other reproductive tissues the following vectors were prepared using tissue specific promoters to drive AlcR expression.

AlcA-Glu11-GUSint-nos

Figure 26:
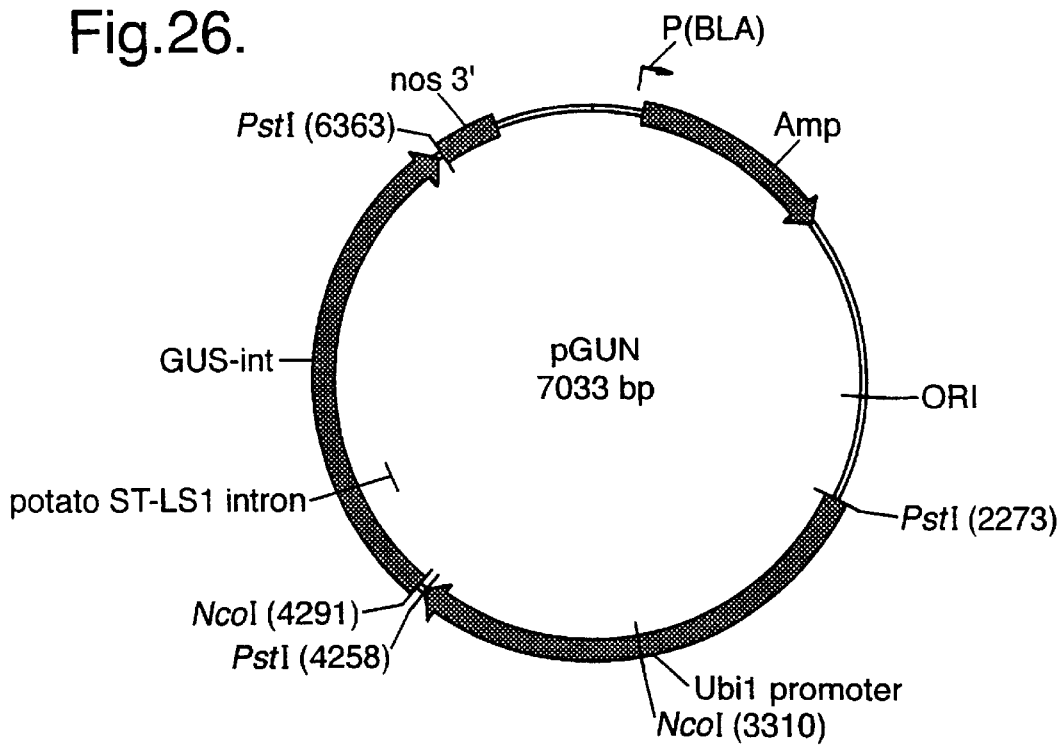
FIG. 26 shows map of pGUN.

A SacI site at the end of the GUS gene in pGUN (FIG. 26) was changed to a PstI site using the QUIckChange Icit as usual and a subsequent NcoI-SacI digest containing the GUS gene (+intron) was used to replace the barstar gene in cassette D (see later) to produce a vector containing AlcA promoter-glucanase enhancer-GUS-nos. This was excised as a PmeI fragment and cloned into pFSE4.

Tap1-AlcR-nos-AlcA-Glu11-GUSint-nos

The AlcA-Glu11-GUSint-nos (Glu11 is glucanase 5' untranslated region) was cloned as a PmeI fragment into PmeI cut pFSE4.

Figure 27:
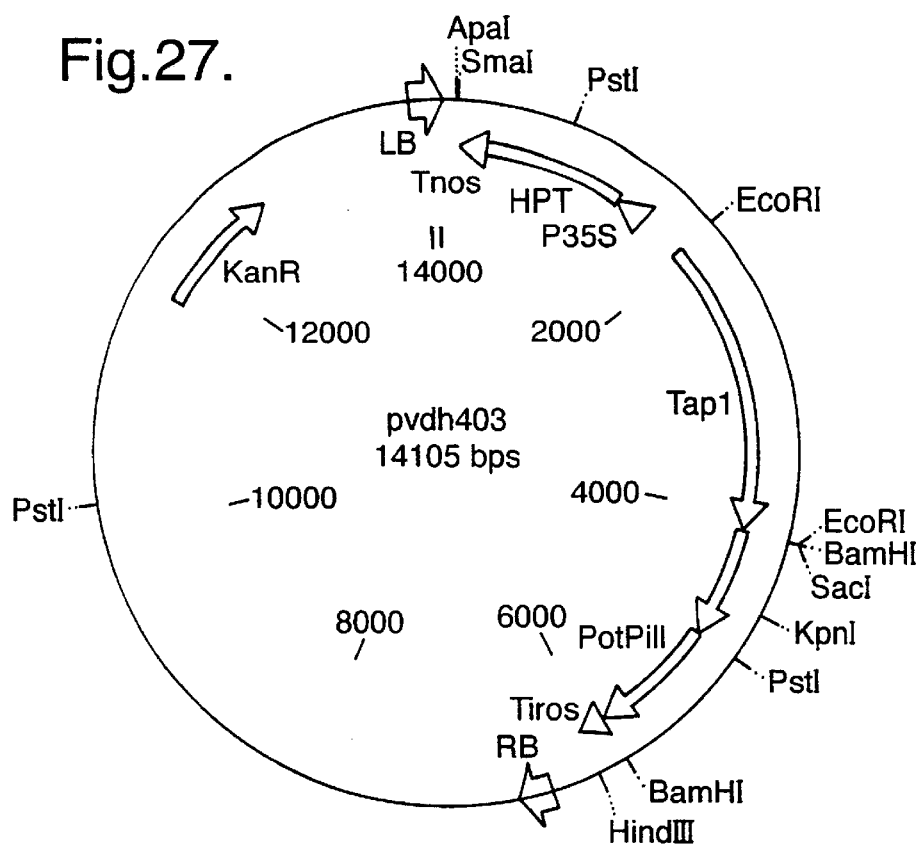
FIG. 27 shows map of pdvh405.
Figure 28:
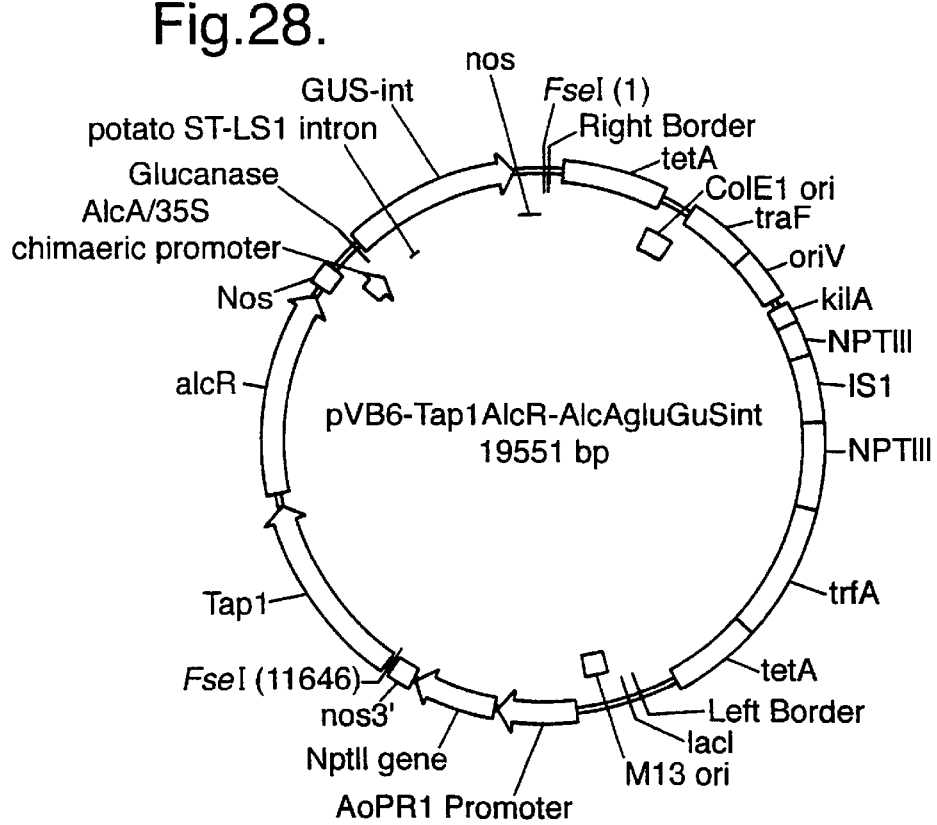
FIG. 28 shows Tap1AlcR-AlcAGluGUSIntnos.

The tapetum specific Tap I promoter originally isolated from Antirrhinum and now cloned from pvdh405 (FIG. 27) was cloned as an EcoRI fragment into pSK-AlcR-nos (generated by cloning the EcoRI-HindIII fragment from pSRN into pSK+) and the resultant Tap1-AlcR-nos was cloned as a NotI fragment into pFSE4-AlcA-Glu11-GUSint-nos. The resultant FseI insert was inserted into pVB6 to generate the final tobacco transformation vector (FIG. 28).

Stig1-AlcR-nos-AlcA-Glu11-GUSint-nos

This construct was made as above except that the pistil transmitting tract specific Stig1 promoter cloned from tobacco (see below) was cloned as an EcoRI-NcoI fragment into pSK-AlcR-nos, and further manipulations performed as above. (FIG. 29).

EXAMPLE 7

CONSTRUCTION OF VECTORS TO ASSESS TISSUE SPECIFICITY OF MALE PROMOTERS pMS14-GUS

The 5.8 Kb promoter fragment from MFS14 (Wright et al. 1993) was fused to the GUS reporter gene. Expression of GUS was detected only in anthers in the early stages of flower bud development but not in leaves.

pMS14-Barnase

Figure 30:
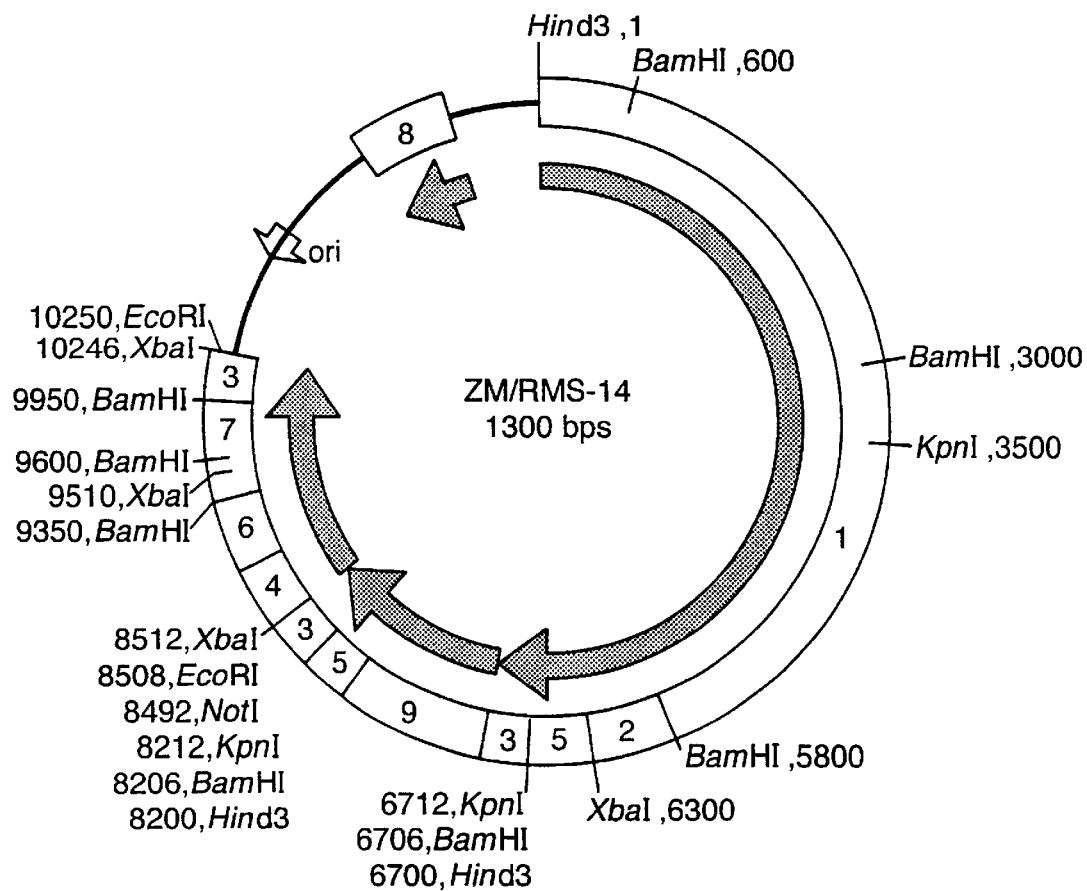
FIG. 30 shows corn transformation vector Zm/RMS14.

The same promoter fragment was fused to barnase to generate the corn transformation vector ZM/RMS14 (FIG. 30). This fusion also contained an out of frame barstar gene with a functional bacterial promoter to provide protection against barnase during the cloning steps. Transgenic maize plants were obtained and several progressed for further analysis. One plant WU25 in particular was studied in some detail by analysing progeny derived from crosses with pollen from a fully fertile plant. All progeny inheriting the transgene as assessed by PCR and leaf paint to detect the pat gene were completely sterile, whereas progeny lacking the transgene were fully fertile. Sterile tassels were generally smaller than those on fertile siblings and carried anthers that lacked pollen and did not excert from the tassel. In all other respects sterile plants were indistinguishable from their fertile non-transgenic siblings.

pC5-GUS

A genomic clone of pectin methyl esterase from maize (named C5 as shown in FIG. 61) has been isolated and the promoter used in transcriptional fusions with GUS to allow study of tissue specificity. The vector was introduced into tobacco by Agrobacterium transformation and transformants selected on kanamycin. Pollen grains from dehisced anthers were harvested and stained for GUS activity. Two plants showed approximately 50% blue staining pollen. No staining was seen in non-transgenic controls. Extracts were made from a range of tissues including stages of developing anthers and analysed fluorometrically for GUS expression. Only very low levels of expression were seen in tissues other than developing and dehisced anthers. Microspore staining indicates that the timing of expression agrees well with Northern data which shows that both in transgenic tobacco and in maize, its native environment the ZmC5 promoter functions late in pollen development.

pMOG1006-C5-GUS (Rice)

C5-GUS(bin) was cut with EcoRI and BamHL to produce a 2.1 kb BamHI-EcoRI fragment (GUS-nos) which was cloned into EcoRI-BamHI cut pMOG1006 and a 1.9 kb BamHI fragment (C5 promoter) which was subsequently cloned into this pMOG1006-Gus-nos to produce the final vector, pMOG1006-C5-GUS, orientation of the promoter was confirmed by sequencing (FIG. 31).

pMOG1006-MFS14-GUS (Rice)

Figure 32:
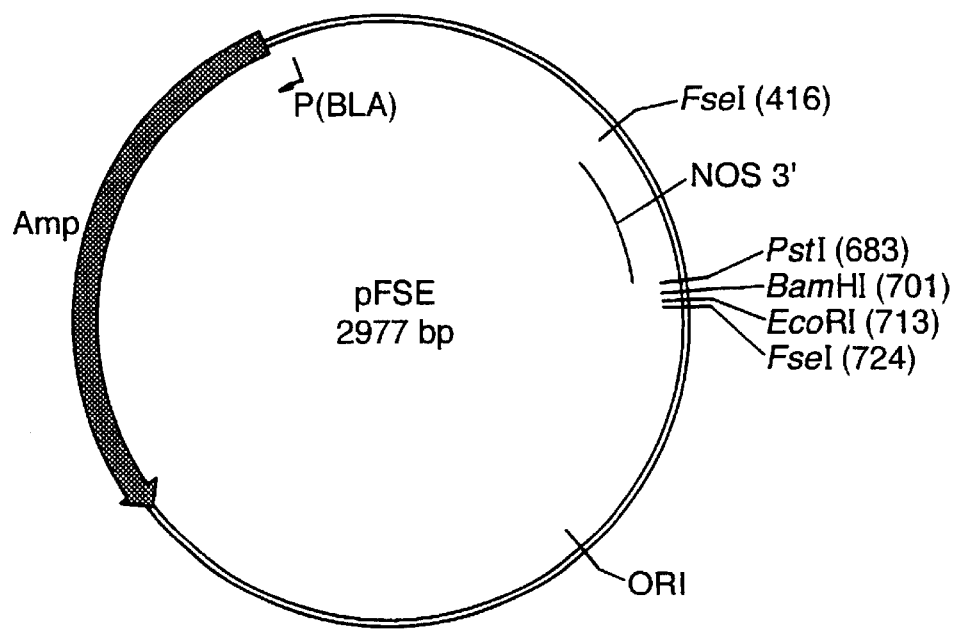
FIG. 32 shows cloning vector pFSE.
Figure 33:
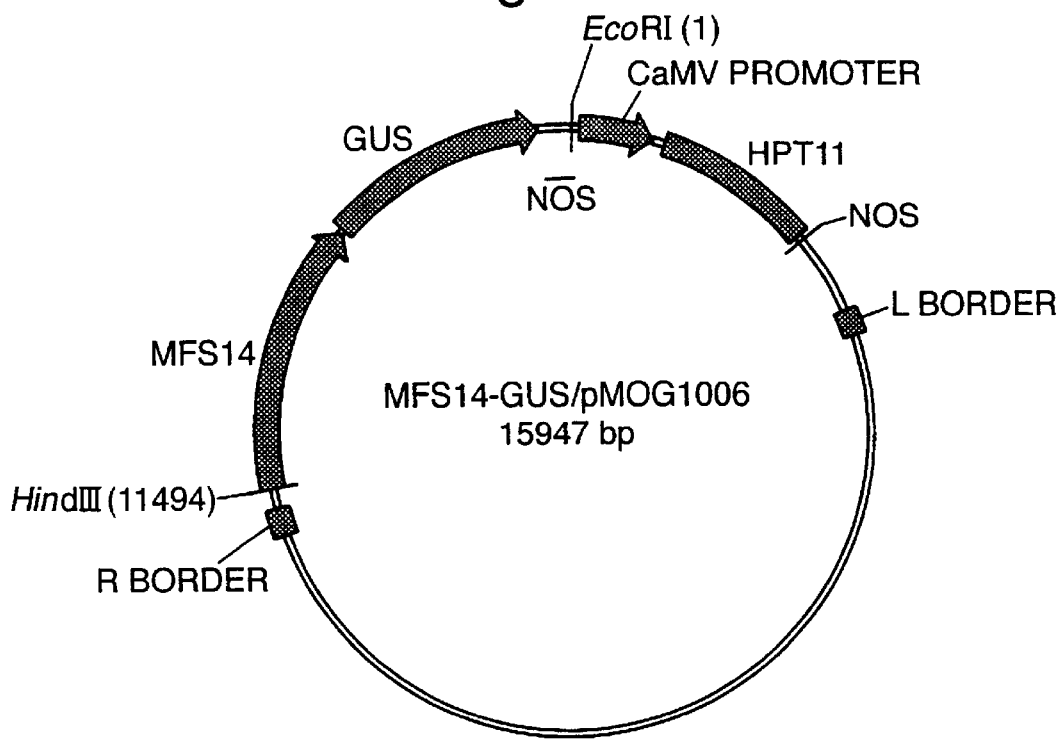
FIG. 33 shows pMOG1006-MFS14-GUS, a rice transformation vector.

The 2.3 Kb MFS14 promoter was isolated from the RMS30 (FIG. 41) vector using BamHI and cloned into pFSE (FIG. 32). The GUS intron cassette was then cloned from pGUN as a PstI fragment into the pFSE-MFS14 vector. The whole MFS14-GUSint-nos fragment was then cloned as an FseI fragment into pMOG1006-Fse (FIG. 33).

EXAMPLE 8

PREPARATION OF VECTORS TO GENERATE STERILITY AND RESTORE FERTILITY

Preparation of Cassette A—MFS14-barnase-nos—a Dominant Sporothytic Male Sterility Cassette The nos terminator from RMS14 was isolated as an EcoRI-HindIII fragment and cloned into pSK+ cut with the same two enzymes. The resulting plasmid was digested with HindIII and an annealed pair of complementary oligonucleotide having the sequences (SEQ ID NOS: 7–8):

Link2A AGC TTC TGG AAT TCG TCT

Figure 34:
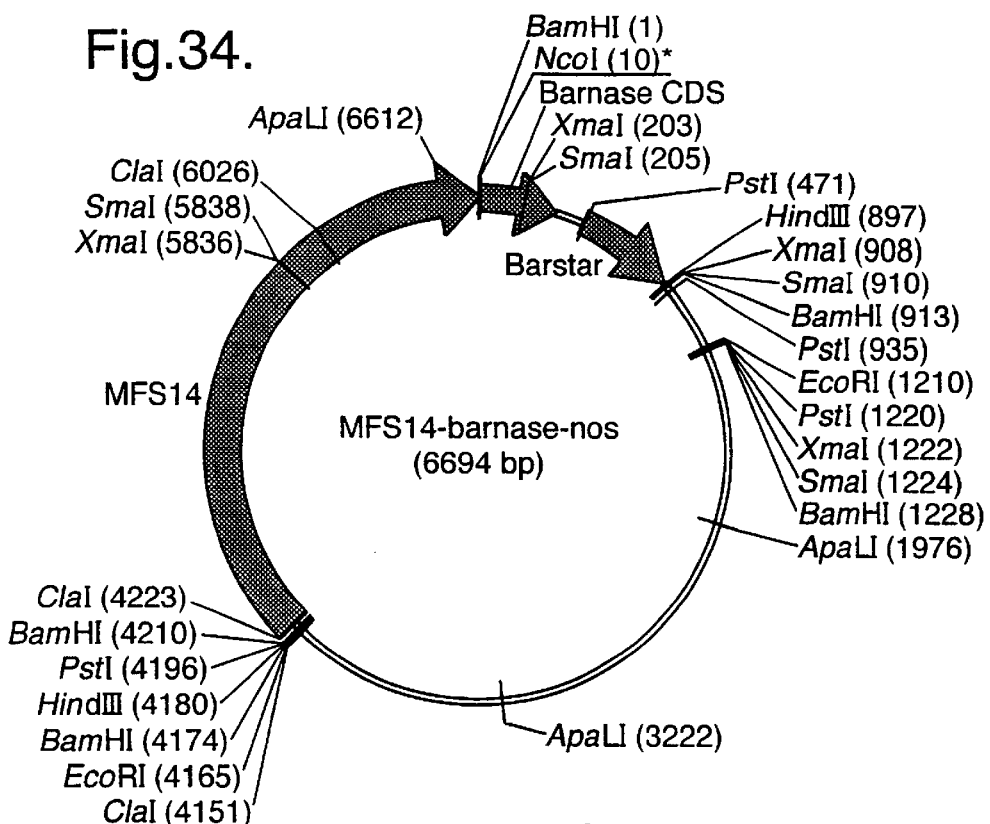
FIG. 34 shows Cassette A, MFS14-barase/barstar-nos.

Link 2B AGC TAG ACG AAT TCC AGA i.e. coding for dHindIII-EcoRI-HindIII ligated with the cut vector. Putative transformed colonies were streaked into nylon membranes and probed in the usual way with the Link2A oligonucleotide labelled with $\gamma^{32}P$. A number of positive colonies were analysed by sequencing and one clone having the orientation in which the HindIII site was internal relative to the two EcoRI sites selected for further manipulation. Into this vector, cut with HindIII and treated with shrimp alkaline phosphatase to prevent religation of the vector was ligated a HindIII fragment isolated from RMS14 carrying the MFS14 promoter and the barnase and barstar coding sequences. Tranformants containing the HindIII fragment in the desired orientation were identified by sequence analysis (FIG. 34). The entire fragment carrying MFS14-barnase/barstar-nos was excised on an EcoRI fragment and inserted into pVB6 and pMOG1006-Fse via pFse4 for introduction into rice and tobacco.

Figure 35:
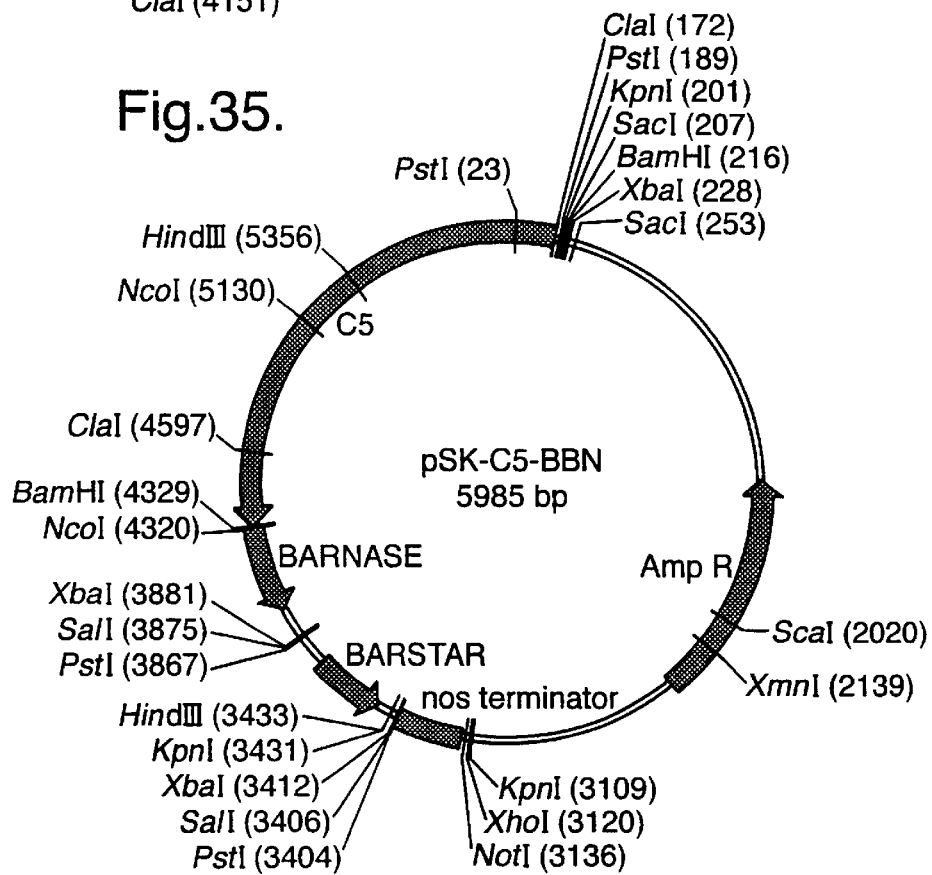
FIG. 35 shows Cassette B, C5-barnase/barstar-nos.

Preparation of Cassette B—C5-barnase—a Dominant Gametophytic Male Sterility Cassette The unique SalI site of pBluescript SK+ (Stratagene) was replaced with a NotI recognition site by insertion of the an oligonucleotide (SEQ ID NO: 9) linker MKLINK4 (5'-TCGATTCG GCGGCCGCCGAA-3') into the digested SalI site. A 0.9 kb, BamHI-HindIII fragment carrying the coding region of barnase followed by a bacterial-promoter-driven barstar coding region, was inserted into the corresponding fragment of the modified pBluescript. The nos terminator on a HindIII-NotI fragment was inserted into the corresponding fragment of the resulting vector. An unwanted BamHI site was then removed using Stratagene's QuickChange system, following the manufacturer's instructions and using oligonucleotides (SEQ ID NOS: 10–11) DAM-3A (5'GGTCGACTCTAGAGGAAC CCCGGGTACCAAGC-3') and DAM-3S (5'-GCTTGGTACCCGGGGTTCCTCTA GAGTCGACC-3'). The resulting plasmid (named pSK-BBN) was digested to completion with BamHI, dephosphorylated with shrimp alkaline phophatase (37° C., 1 hour). A 1.9 kb BamHI fragment of the C55' flanking region was ligated into this, followed by digestion with BamHI and PstI to check for presence and orientation of the insert, respectively. The resulting plasmid was named pSK-C5-BBN (FIG. 35). The entire cassette was then removed as an EcoRI-NotI fragment to a binary plant transformation vector pVB6. The construct was then introduced into *Agrobacterium Tumefaciens* by the freeze-thaw method. Standard techniques were used to introduce the DNA into tobacco.

Prerparation of Cassette C—35S-AlcR-nos

An EcoRI-HindIII fragment was isolated from the vector known as pUC3, this fragment contains the AlcR coding sequence and nos terminator. This fragment was cloned into EcoRI-HindIII cut pSK+. An annealed pair of complementary oligonucleotides having the sequences (SEQ ID NOS: 12–13):

Link5A AGC TAT TAG CGG CCG CTA TGT TTA AAC GCG T

Figure 36:
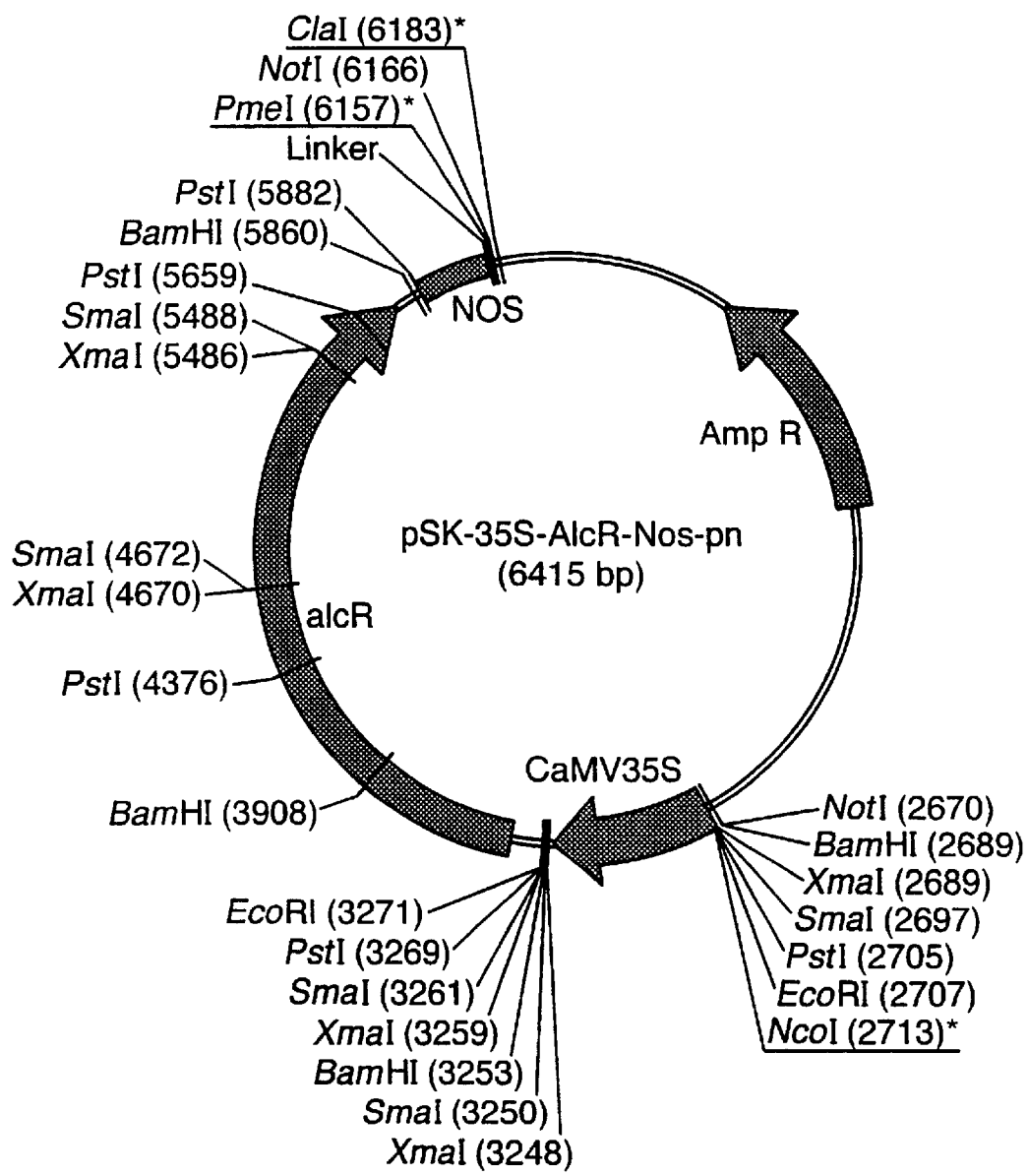
FIG. 36 shows Cassette C, CaMV 35S-AlcR-nos.

Link5B AGC TAC GCG TTT AAA CAT AGC GGC CGC TAA T carrying restriction sites for ΔHindIII-NotI-PmeI-ΔHindIII was inserted into the HindIII site, thus adding a Pme1 and Not1 site and deleting the HindIII site at the 3' end of the cassette. The EcoRI fragment from pUC3 carrying the 35S CaMV promoter was cloned into the EcoRI site and oriented by restriction and sequence analysis (FIG. 36). The entire cassette can be excised as a NotI fragment for further manipulation, and contains the PmeI site into which the AlcA-Glu11-barstar-nos cassette can be inserted.

Preparation of Cassette D AlcA-Glu11-barstar-nos

The vector pMJB1 was digested with XhoI and NcoI to remove the TMV omega enhancer. Two oligonucleotides encoding the glucanase 11 5'UTR and flanked by XhoI and NcoI sites, having the sequences (SEQ ID NOS: 14–15):

Glu1 TCG AGA CAA TTT CAG CTC AAG TGT TTC TTA CTC TCT CAT TTC CAT TTT AGC

Figure 37:
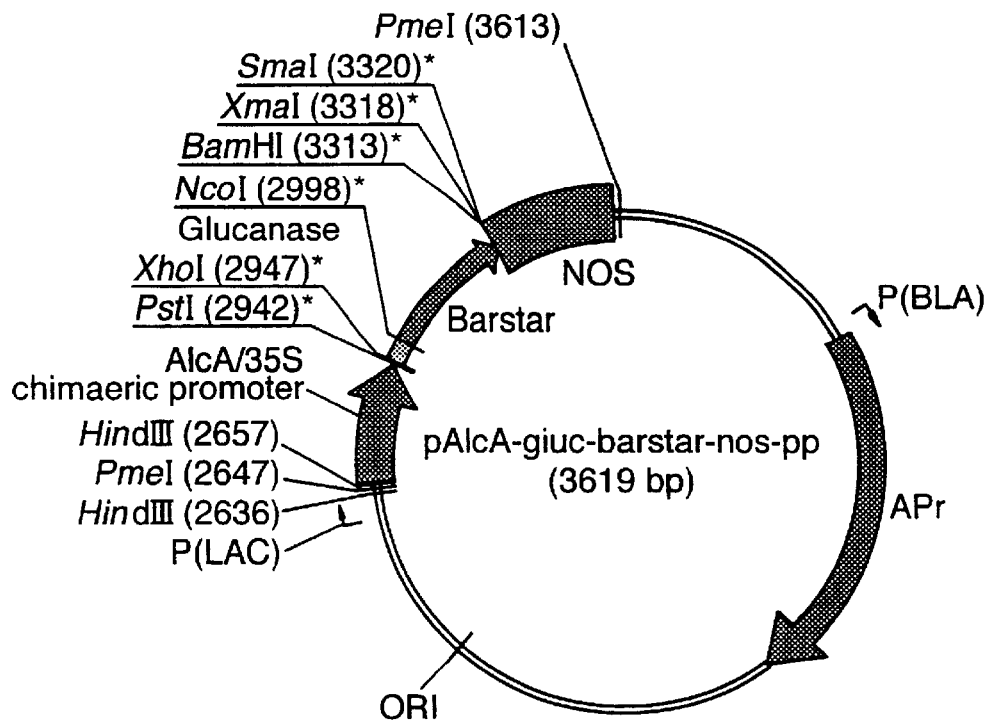
FIG. 37 shows Cassette D, AlcA.Glu1 1-barstar-nos.

Glu11 CAT GGC TAA AAT GGT TTT GAG AGA GTA AGA AAC ACT TGA GCT GAA ATT GTC were annealed as usual and ligated into the cut vector. The sequenced vector was digested with HindIII and XhoI to remove the 35S CaMV promoter and the AlcA promoter ligated in on a HindIII-XhoI fragment. A fragment encoding barstar having NcoI and BamHI ends was obtained by PCR from RMS9. This was then inserted into the above vector cut with NcoI-BamHI to give a complete cassette carrying AlcA-Glu11-barstar-nos. In order to facilitate manipulation of the cassette a PmeI site was added at each end by the use of oligonucleotides encoding ΔHindIII-PmeI-HindIII and ΔEcoRI-PmeI-ΔEcoRI (FIG. 37). This allows the insertion of this cassette into the 35S-AlcR-nos cassette described above enabling both components of the AlcA/R switch to be moved into pFSE4 as a NotI fragment.

Preparation of Cassette E MFS14-Glu11-barstar-nos—a Male Fertility Restorer Cassette A 320 bp BamHI-SacI fragment carrying the 3' end of the MFS14 promoter was cloned into BamHI-SacI cut pSK+. The HindIII site was removed using the QuickChange kit from Qiagen following standard procedures. The oligonucleotides used to remove the site had the sequences (SEQ ID NOS: 16–17):

MKM1A CGG TAT CGA TAA GCT AGA TAT CGA ATT CCT G

MKM1S CAG GAA TTC GAT ATC TAG CTT ATC GAT ACC G

The deletion of the site was confirmed by restriction analysis and by sequencing. A new HindIII site was then introduced near the SacI site by insertion of annealed oligonucleotides (SEQ ID NOS: 18–19) encoding ΔSacI-HindIII-SacI sites.

SHSLINK1 CAT AAA GCT TAT ACA GCT

SHSLINK2 GTA TAA GCT TTA TGA GCT

The presence of the new site was confirmed by restriction analysis and the correct orientation of the linker defined by sequencing. The desired orientation gave a HindIII site to the outside of the SacI site relative to the BamHI site. The BamHI site was then removed and a new XhoI site introduced in the same way using an oligonucleotide encoding dBamHI-XhoI-ΔBamHI. This had the sequence (SEQ ID NO: 20):

Link6 GAT CGT ATC TCG AGA TAC

The absence of the BamHI site and the introduction of the XhoI site was confirmed in the usual way.

Figure 38:
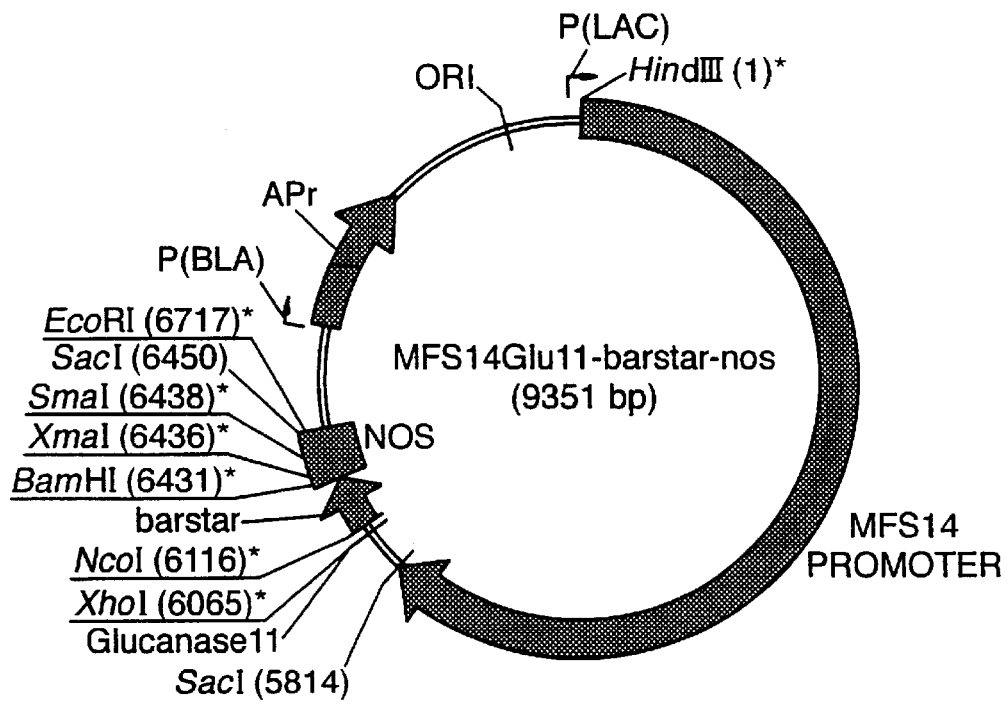
FIG. 38 shows Cassette E, MFS14.Glu1 1-barstar-nos.

RMS14 was digested with HindIII and SacI and the 5.5 Kb fragment encoding the remainder of the MFS14 promoter was isolated. This fragment was then inserted into HindIII-SacI cut vector above and the integrity of the promoter confirmed by sequencing. The whole of the MFS14 promoter was then excised as a HindIII-XhoI cassette and inserted in Cassette D replacing the AlcA promoter at the stage before addition of linkers to the ends. For this cassette linkers introducing Swa1 sites at each end were used (FIG. 38).

Preparation of Cassette F Stig1-barnase-nos—a Female Sporophytic Sterility Cassette A BamHI site was introduced close to the translation start site of the STIG1 promoter in the vector pSK-STIG1. This was achieved using the Stratagene QuickChange Kit with oligonucleotides (SEQ ID NOS: 21–22):

ST1-BA (5'-GATAAAAGCCATAATTGGATCCTGGTGGTTTCTGC-3') and

ST1-BS (5'-GCAGAAACCACCAGGATCCAATTATGGCTTTTATC-3').

Figure 39:
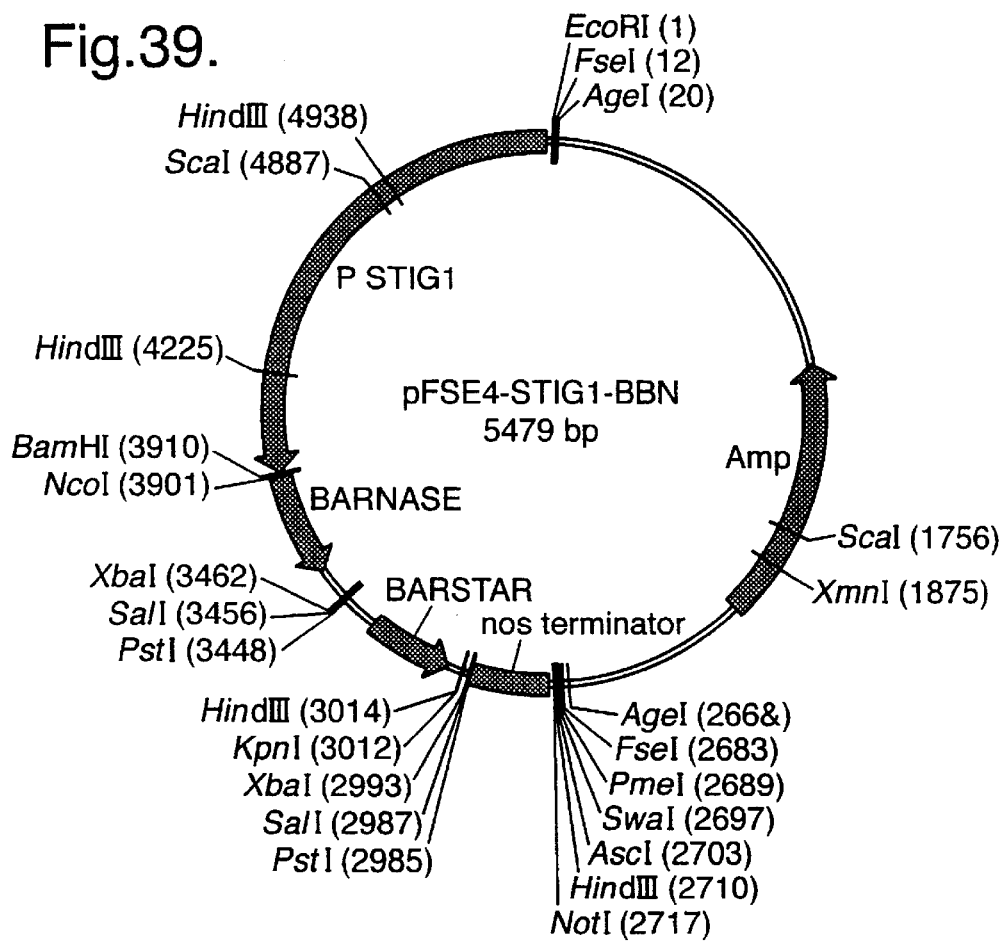
FIG. 39 shows Cassette F, Stigl-barnase/barstar-nos.

The 1.6 kb SUG1 promoter was then released on a BamHI fragment and cloned into BamHI-digested pSK-BBN. Presence and correct orientation of the promoter were determined by PCR amplification between vector and promoter sequences. The STIG1-BBN cassette was transferred, on a NotI-EcoRI fragment to the vector pFSE4, the resulting plasmid being named pFSE4-STIG1-BBN (FIG. 39). The entire cassette was then transferred as an FseI fragment to VB6.

Preparation of Cassette G Stig1-Glu11-barstar-nos—a Female Fertility Restorer Cassette The construct pAlcA-GluII-barstar-nos-pp was modified to replace a HindIII restriction site with an EcoRI site. This was achieved using the Stratagene QuickChange Kit and oligonucleotides (SEQ ID NOS: 23–24):

DAM-6A (5'-CGGAACTATCCCGAATTCTGCACCGTTTAAACGC-3') and

DAM-6S (5'-GCGTTTAAACGGTGCAGAATTCGGGATAGTTCCG-3').

A XhoI site was introduced close to the translation start site of the STIG1 promoter in the vector pSK-STIG1. This was achieved using Stratagene's QuickChange Kit with the oligonucleotides (SEQ ID NOS: 25–26):

ST1-XA (5'-GATAAAAGCCATAATTGGCTCGAGGTGGTTTCTGCTGAG-3')

ST1-XS (5'-CTCAGCAGAAACCACCTCGAGCCAATTATGGCTTTTATC-3

Figure 40:
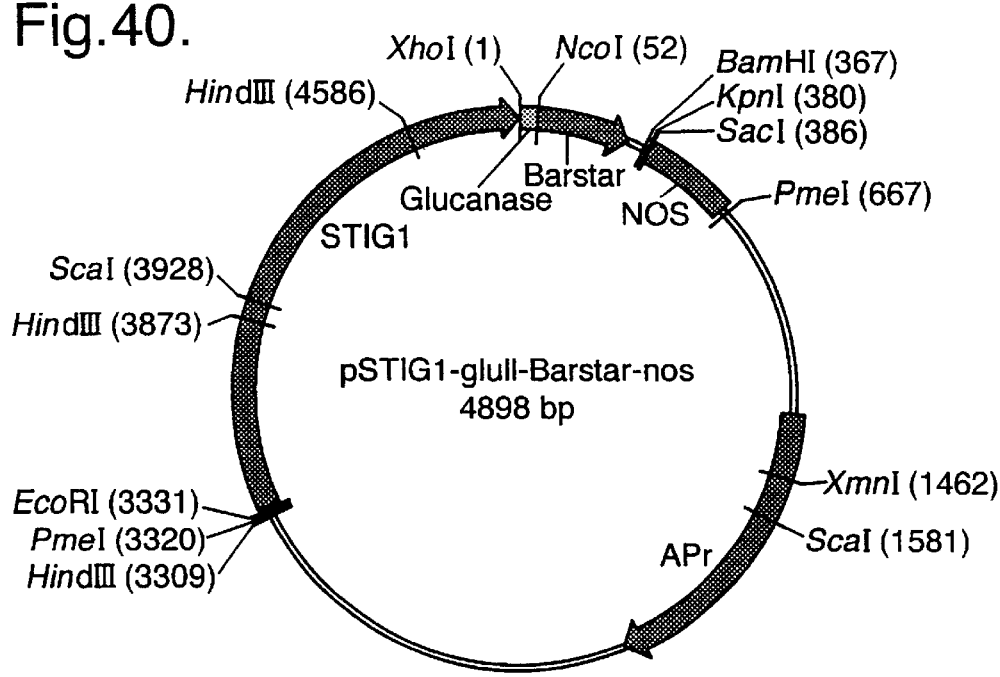
FIG. 40 shows Cassette G, Stigl.Glu1 1-barstar-nos.

The 1.6kb STIG 1 promoter was then released on a XhoI-EcoRI fragment and cloned into the larger fragment produced by digestion pAlcA-gluII-barstar-nos-pp with XhoI and EcoRI, replacing the AlcA promoter with the STIGI promoter (FIG. 40). The whole cassette was excised on a PmeI fragment and cloned into pVB6 and pMOG1006-Fse.

Preparation of a Switchable TPS Vector—AlcA-TPS-nos Tap1-AlcR-nos

The Tap1-AlcR-nos cassette has been described. The GUS gene in pAGS was replaced with TPS and the new cassette was cloned as a HindIII cassette into pFSE4. The Tap1-AlcR-nos described earlier was as a NotI fragment into this pFSE4-AlcA-TPS-nos vector. The whole FseI fragment was excised and cloned into a pVB6. This vector can now be used to retransform tobacco made sterile by transformation with a construct carrying a Tap1-TPP-nos expression cassette.

EXAMPLE 9

PREPARATION OF PLANT TRANSFORMATION VECTORS

Any combination of the above cassettes may be made in pFSE4 and subsequent transfer of the resulting FseI fragment into either pMOG1006-Fse or pVB6 allows transformation into tobacco or rice.

The following combinations of cassettes have been made as plant transformation vectors, A+C+D=sporophytic male sterile plant whose fertility is restorable by chemical induction of the restorer gene E=sporophytic male fertility restorer plant, which when cross pollinated onto the above plant restores fertility in the progeny F+C+D=sporophytic female sterile plant whose fertility is restorable by chemical induction of the restorer gene G=sporophytic female fertility restorer plant which when cross pollinated by the above plant produces female fertile progeny.

B+D=gametophytic male sterile plant whose fertility can be restored by chemical induction of the restorer gene The generation of the parents of F1 hybrid plants as described herein is achieved in the following way:

| Male Parent i.e. female sterile | | |
|---|---|---|
| Cassette F | Stig1-barnase | female sterility |
| Cassette E | MFS14-Glu11-barstar | male restorer |
| Cassette C | 35S-AlcR-nos | switch component |
| Cassette D | AlcA-Glu11-Barstar | " " |
| Female parent i.e. male sterile | | |
| Cassette A | MFS14-barnase | male sterility |
| Cassette G | Stig1-Glu11-barstar | female restorer |
| Cassette C | 35S-AlcR-nos | switch component |
| Cassette D | AlcA-Glu11-barstar | " " |

EXAMPLE 10

CONSTRUCTION OF VECTORS TO TEST NEW PIG GENE

RMS30 and RMS32 (Tobacco)

The tubulin gene was cloned as a Hinf1 fragment from ptubulin and cloned into pFSE-MFS14 generated above.

Figure 41:
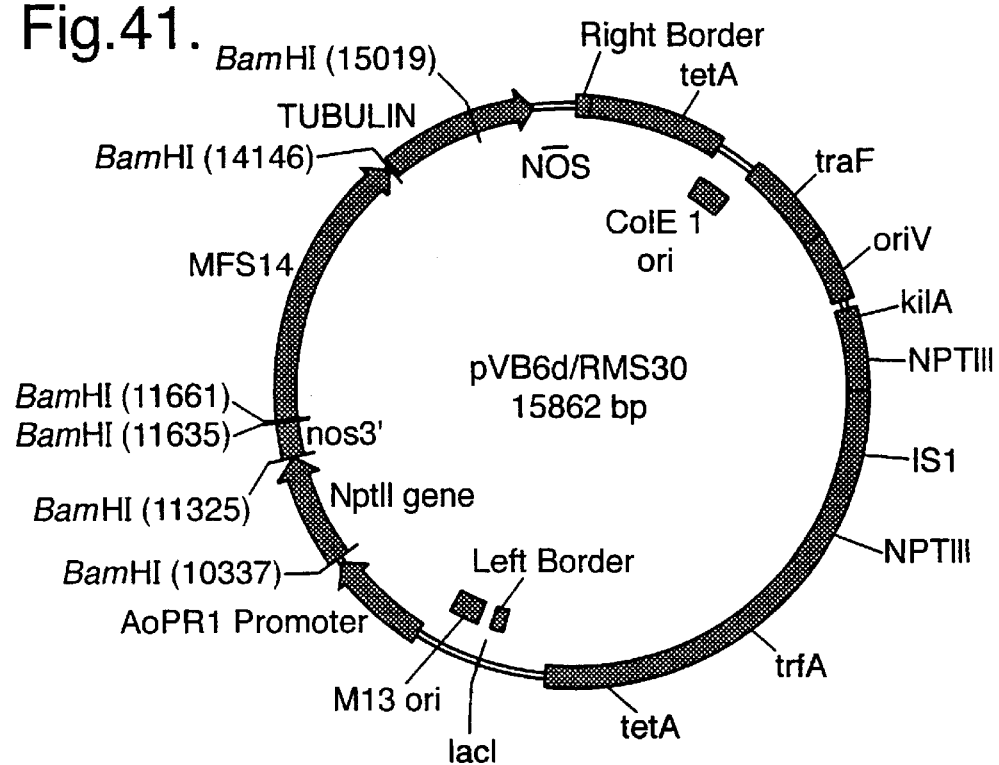
FIG. 41 shows RMS30.

The resultant MFS14-tubulin nos was cloned into pVB6 as an FSE fragment to produce RMS30 (FIG. 41).

Figure 42:
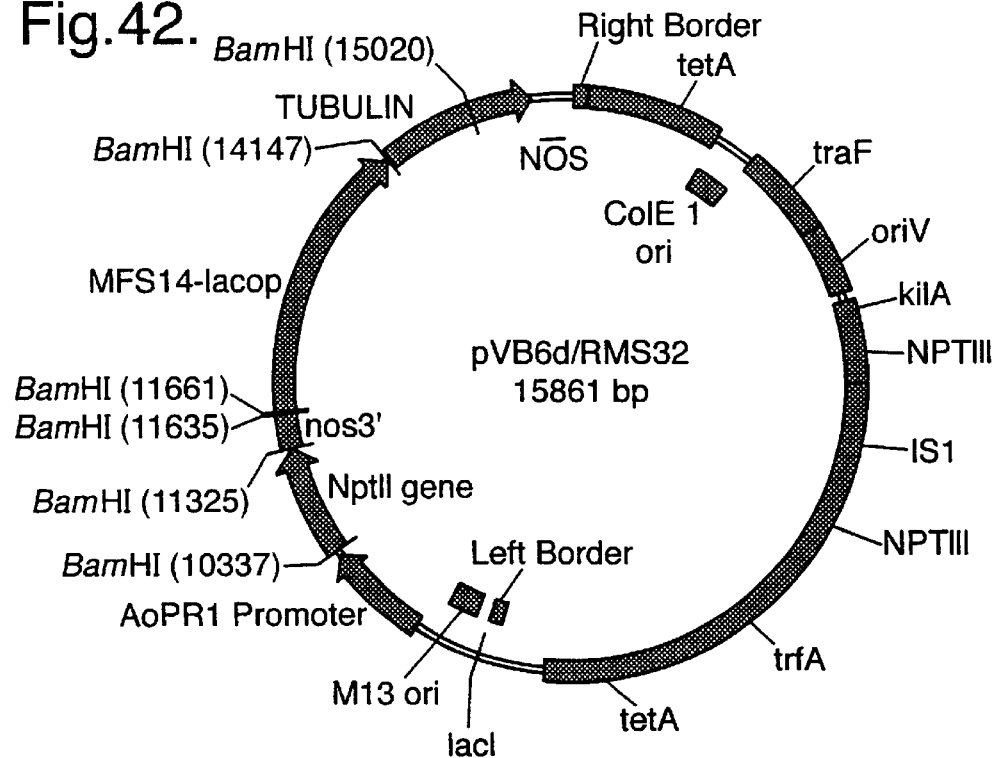
FIG. 42 shows RMS32.

The MFS14+lac operator promoter was excised from RMS32 as a BamHII fragment and cloned into pFSE. Following insertion of the tubulin gene, the MFS14-lac-op-tubulin-nos FseI fragment was cloned into pVB6 to produce RMS32 (FIG. 42).

RMS30 and RMS32 (Rice)

The FseI fragments containing MFS14 promoter (+/− lac op)-tubulin-nos were cloned into pMOG1006-Fse to generate the plant transformation vectors.

Optimisation of Trehalose-phosphate Phosphatase (TPP) and Trehalose-6-phosphate Hydrolase (TreC) for use in Generating Sterility in *Zea Mays*

Versions of TPP and TreC coding regions optimised for expression in *Zea mays* (which has a preference for G or C in redundant positions of each codon) are synthesised by Operon Technologies Inc. Nucleotide sequences are derived from their amino acid sequences using codons present in vivo above 1.0% and at frequencies representative of the naturally occurring ratios (according to the Genbank Codon Usage Database, Release 108). Also included are useful restriction enzyme sites close to the translation start sites including BamHI and NcoI and, and a PstI site at the 3' ends to facilitate cloning.

Constructs to Test the use of Codon Optimised TPP and TreC *Zea Mays*

The BamHI site at the 5' end of the MFS14 promoter in the vector pFSE-MFS14 is removed using Stratagene's QuickChange system with the oligonucleotides (SEQ ID NOS: 27–28):

DAM-7A
5'-CGATGCTTTCGGAACCGGTACCGAATTCG-3'
DAM-7S:
5'-CGAATTCGGTACCGGTTCCGAAAGCATCG-3'

The synthetic TPP and TreC genes are then excised on BamHI—PstI fragments and cloned between the MFS14 promoter and nos terminator in the modified pFSE-MFS14 vector. The adh1 intron is inserted between the promoter and coding sequences to boost expression levels. The complete cassette is then transferred to a pUC based cloning vector containing IGPD bacterial selection marker and a herbicide resistance gene cassette for selection of transgenic plants.

EXAMPLE 11

PRODUCTION OF TRANSGENIC PLANTS pSRN.AGS has been introduced into tobacco, oilseed rape and tomato (these plants are referred to as Alc-GUS plants) pMOG1006-Fse-SRNAGS and pMOG1006-C5-GUS have been introduced into rice via Agrobacterium mediated transformation.

Plant transformation vectors containing each of the cassette combinations given above have been introduced into tobacco and/or rice by Agrobacterium mediated transformation. Explants were analysed by PCR and those containing intact inserts were clonally propagated and transferred to the glass house and grown to flowering. RMS30 and 32 have also been introduced into tobacco.

pUIRN.AGS has been introduced into wheat and corn via projectile bombardment methods, and transgenic plants recovered, by means of co-bombardment with a plasmid carrying a selectable marker. Other vectors to test various components are transformed into corn by microprojectile bombardment.

EXAMPLE 12

ANALYSIS OF TRANSGENIC PLANTS

Studies on GUS Expression From the AlcA Promoter

In Tissue Culture

In order to assess whether plants, following transformation with a construct containing a promoter attached to a cytotoxic gene, such as barnase, would be recoverable, particularly if the promoter has some expression in the callus phase of the transformation process, expression in tobacco callus was studied to determine whether or not expression was constitutive as in the case of the GST27 promoter, or whether it could be induced by application of ethanol.

Figure 43:
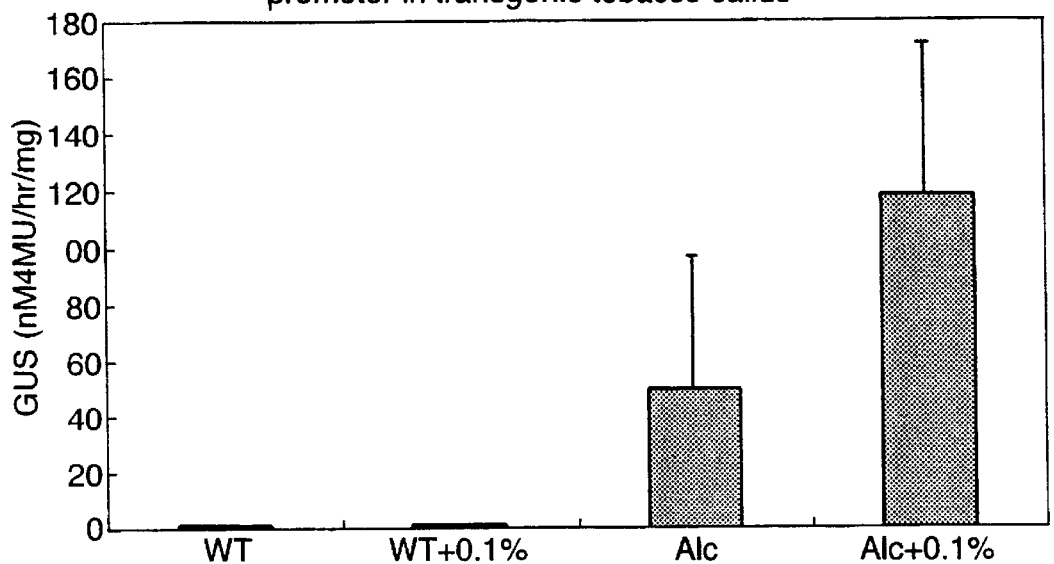
FIG. 43 shows GUS expression in uninduced and ethanol induced wild type and transgenic Alc-GUS tobacco callus.

Four-week old Alc-GUS (35S-AlcR-nos/AlcA-GUS-nos) tobacco plants grown under standard tissue culture conditions were used to test the expression of the AlcA promoter in callus both with and without ethanol. Leaf discs were produced and placed onto MS medium supplemented with 3% (w/v) sucrose and 0.8% (w/v) Bacto-agar, 1 μg/ml 6-BAP and 100 ng/ml NAA hormones. Some of the discs were placed onto this medium containing 0.1% (v/v) ethanol. After 3 weeks when callus production had progressed, samples of callus were used for fluorometric GUS assays, the result of which is shown in FIG. 43.

The GUS levels show that the AlcA promoter is leaky in callus and levels can be increased with the addition of ethanol to the plant tissue culture medium. Therefore, transgenics may be recovered using the AlcA promoter driving a restorer gene in the same construct as a promoter driving a cytotoxic gene.

In the Glasshouse

The AlcA/R gene switch has been demonstrated to give good levels of reporter or trait gene induction in the leaves of tobacco upon addition of the chemical inducer ethanol, either by application as spray, vapour or root drench. (Caddick et al., Salter et al.) Transgenic AlcA-GUS tobacco, oilseed rape and tomato plants were used to examine gene induction in floral tissues.

Tobacco

Figure 44:
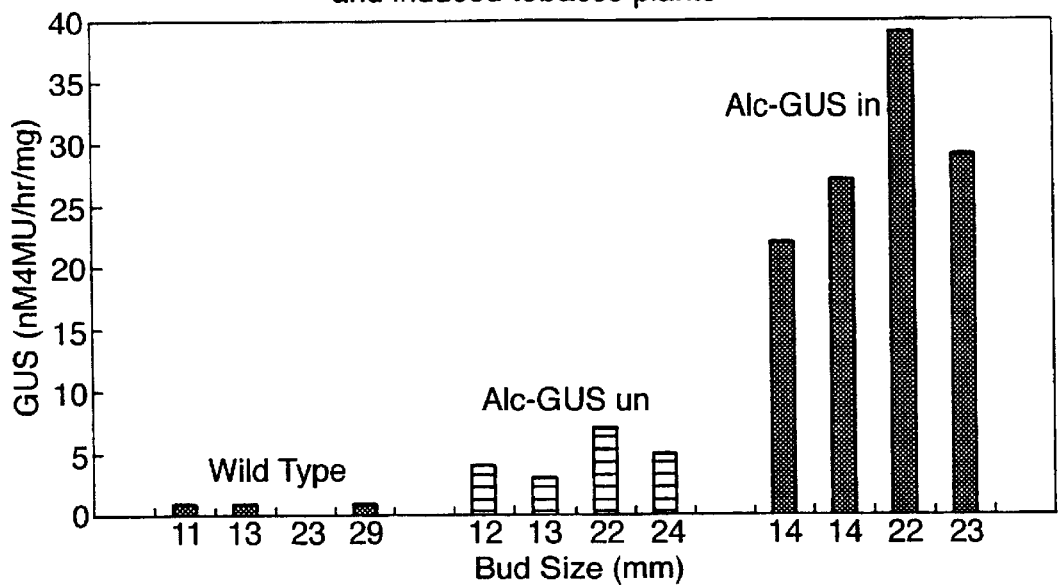
FIG. 44 shows GUS expression in uninduced and ethanol vapour induced wild type and transgenic Alc-GUS tobacco anthers.

1) A plastic bag was sealed around a tobacco AlcA-GUS tobacco flower stem and a small pot containing 50 ml of 5% ethanol was placed inside the bag. After 3 days anthers from different flower bud stages were harvested and assayed for GUS expression. Results are shown in FIG. 44. This shows the GUS values from four independent flower buds from wild type, uninduced AlcA-GUS and induced AlcA-GUS plants. Flower buds were measured in mm and each bar represents five anthers. The graph shows that compared to AlcA-GUS plants which did not receive the ethanol vapour treatment, anthers from the induced plant contained higher levels of GUS in them.

Figure 45:
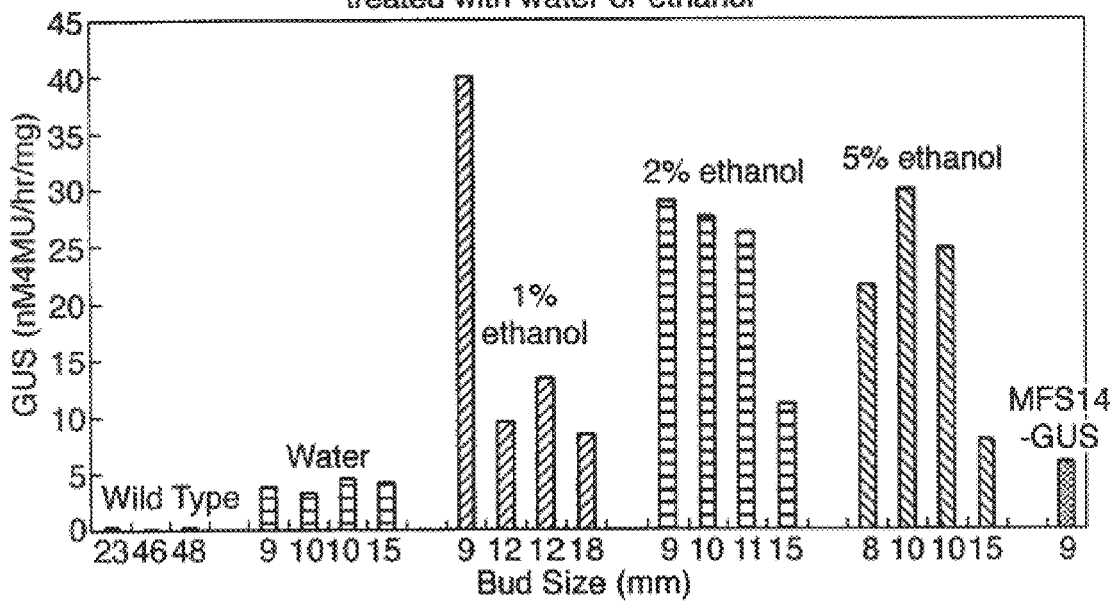
FIG. 45 as above but induction by root drench with water and ethanol.

2) Flower stems from wild type and Alc-GUS tobacco plants were cut and placed into beakers containing 300 ml of either water, 1%, 2% or 5% ethanol and left in the glasshouse for two days before harvesting anthers from the flower buds for fluorometric GUS assays. FIG. 45 is a bar graph representing the GUS data from this experiment showing anthers from wild type, water treated Alc-GUS flower stem and 1%, 2% or 5% ethanol treated Alc-GUS flower stems. This experiment also demonstrates that expression of the reporter gene has been induced by ethanol in the anthers at levels above those seen in the water treated flowers. Levels of GUS expression from the induced AlcA-GUS anthers were above those from a MFS14-GUS plant.

Figure 46:
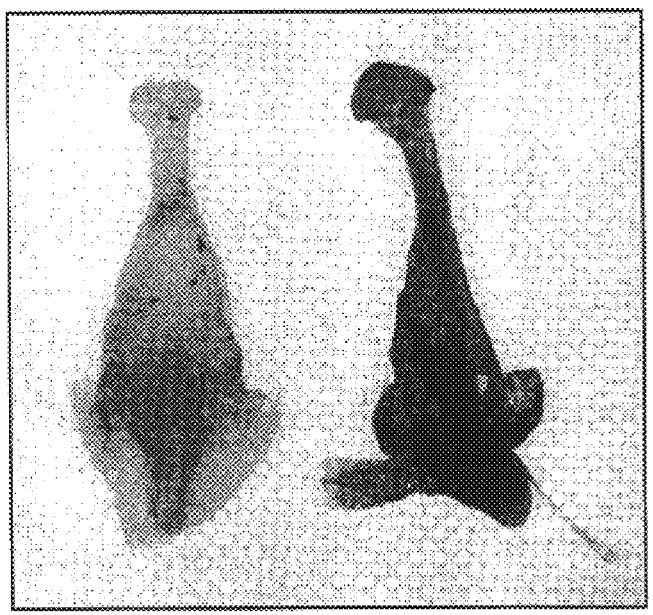
FIG. 46 shows GUS expression in uninduced and induced pistils from 9–10 mm tobacco flower buds.
Figure 47:
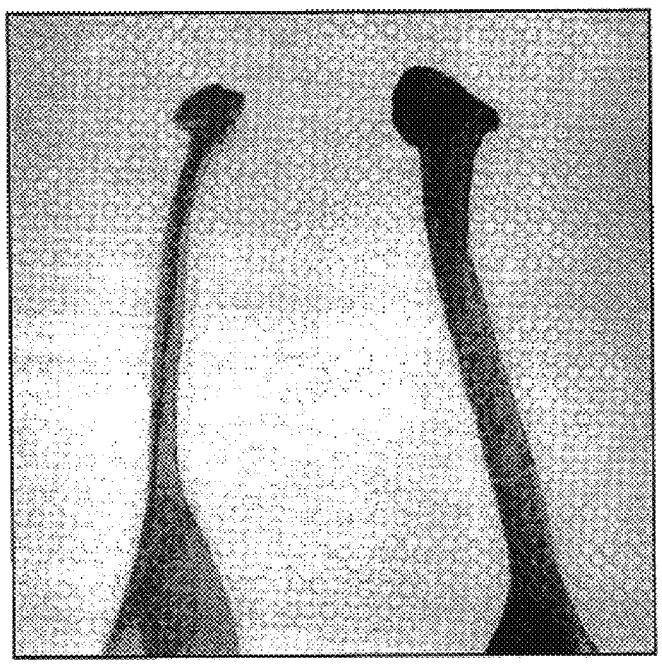
FIG. 47 shows GUS expression in uninduced and induced pistils from 1 7–22 mm tobacco flower buds.
Figure 48:
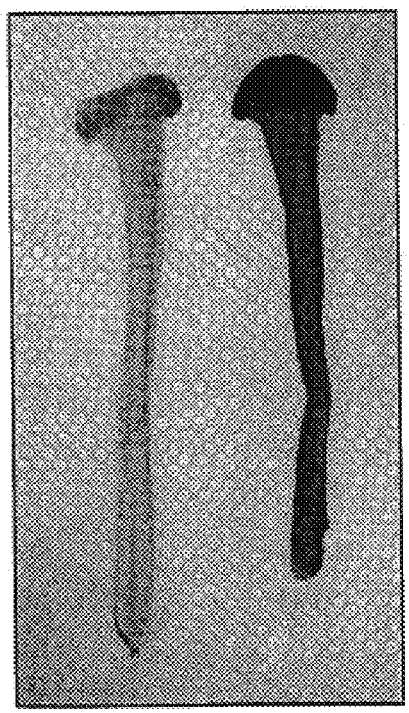
FIG. 48 shows GUS expression in uninduced and induced pistils from 33–35 mm tobacco flower buds.

3) Mature AlcA-GUS tobacco plants were root drenched in the glasshouse with 250 ml of either water, or 5% ethanol. A wild type and a 35S-GUS plant were also treated with ethanol. Two days later pistils from various size flower buds were dissected and stained for GUS activity. FIG. 46 shows pistils from 9–10 mm buds from the water and the 5% ethanol treated Alc-GUS plants. The photograph clearly demonstrates that the ethanol treatment has lead to induction of GUS in the pistils. FIGS. 47 and 48 show the stigma/style region of pistils from 17–22 mm and 33–35 mm buds respectively, again from water treated and ethanol treated Alc-GUS plants. GUS staining is present throughout this area compared to the water treated plant which was similar to wild type.

4) Alc-CAT plants (35S-AlcR-nos/AlcA-CAT-nos) were also tested and showed an increase in reporter gene levels in floral tissues after induction with ethanol.

Oilseed Rape

1) Oilseed rape (OSR) AlcA-GUS plants were root drenched with 250m1 of either water, 1% or 2% ethanol both on day 0 and day 1. Flower samples from these plants were then taken two days after the first induction. The samples taken for fluorometric GUS analysis were anthers from mature flowers (mature indicating that they were fully opened), stigma/styles from mature flowers, anthers from immature flowers (flower buds with the petals unopened), stigma/styles from immature flowers and finally the rest of the flower pistils which includes the ovaries.

Figure 49:
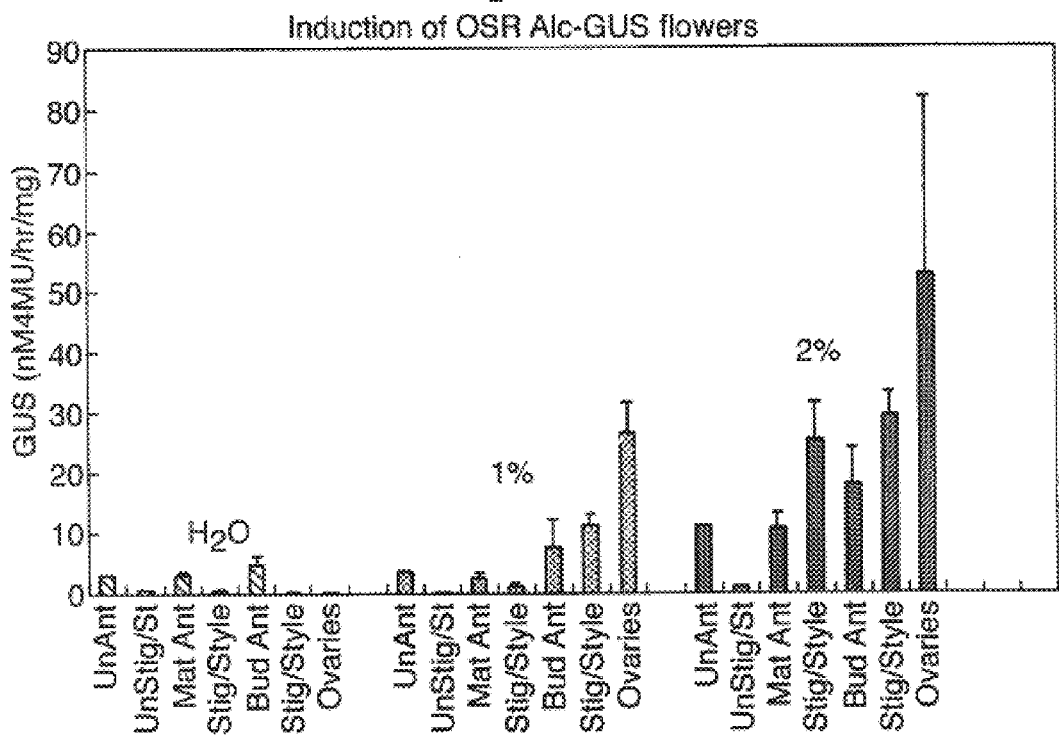
FIG. 49 shows GUS expression in uninduced and induced oil seed rape flowers.

FIG. 49 shows the GUS data graphically and from left to right shows the results from water induced Alc-GUS, 1% ethanol induced Alc-GUS and 2% ethanol induced Alc-GUS oilseed rape plants. The first two bars in each section represent uninduced anther and uninduced stigma/style GUS levels respectively. Each bar represents three replicates with each replicate containing anthers from three different flowers or stigma/styles from eight different flowers or ovaries from six different flowers.

The data clearly shows an increase in GUS levels in floral tissues when comparing the water treated oilseed rape to the ethanol-induced plants. All tissues examined in the 2% ethanol-treated plants show an increase in GUS from both uninduced levels and from the water-treated control plant.

Figure 50:
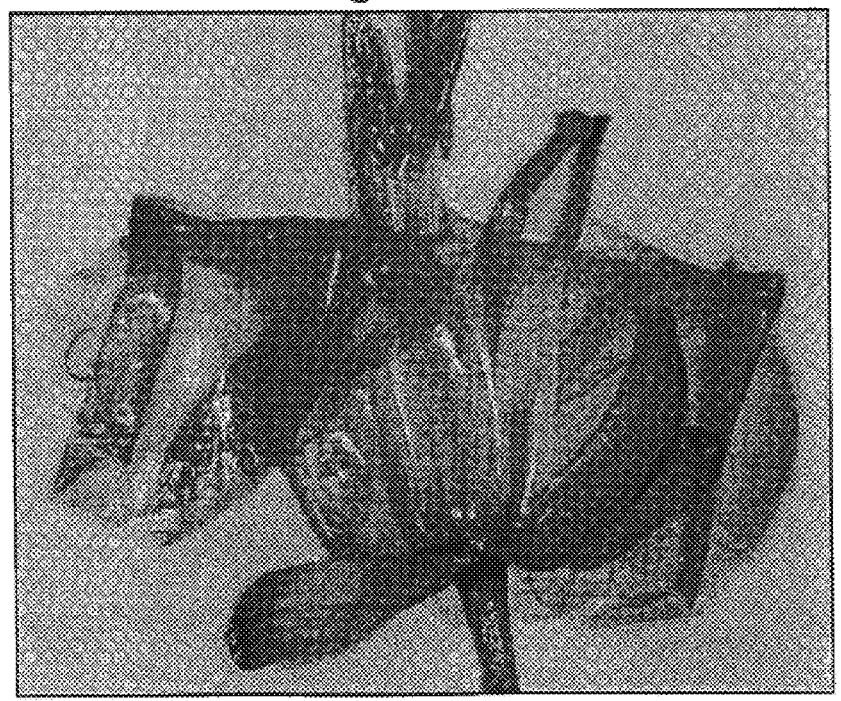
FIG. 50 shows uninduced oilseed rape flower.
Figure 51:
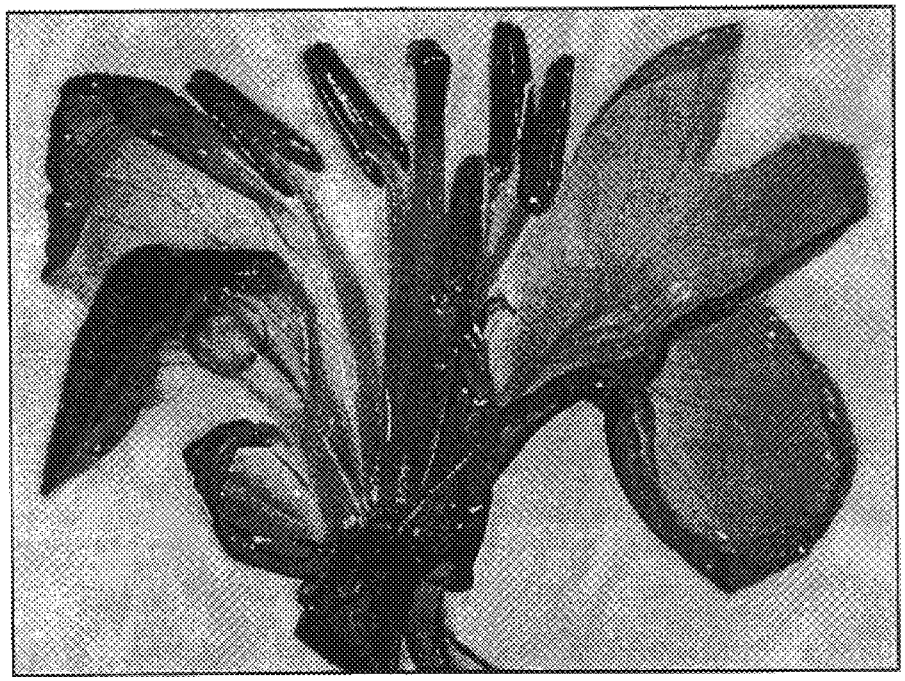
FIG. 51 shows GUS expression in oil seed rape pistils two days after root drench induction.

2) Oilseed rape Aic-GUS flowers were subjected to GUS staining following induction with ethanol. FIG. 50 is a photograph of an Alc-GUS flower before induction and FIG. 51 is a photograph of a flower from the same plant, two days after root drenching with 250 ml of 5% ethanol. This shows that the treatment has lead to reporter gene induction in the stigma/style region as well as the filaments.

Figure 52:
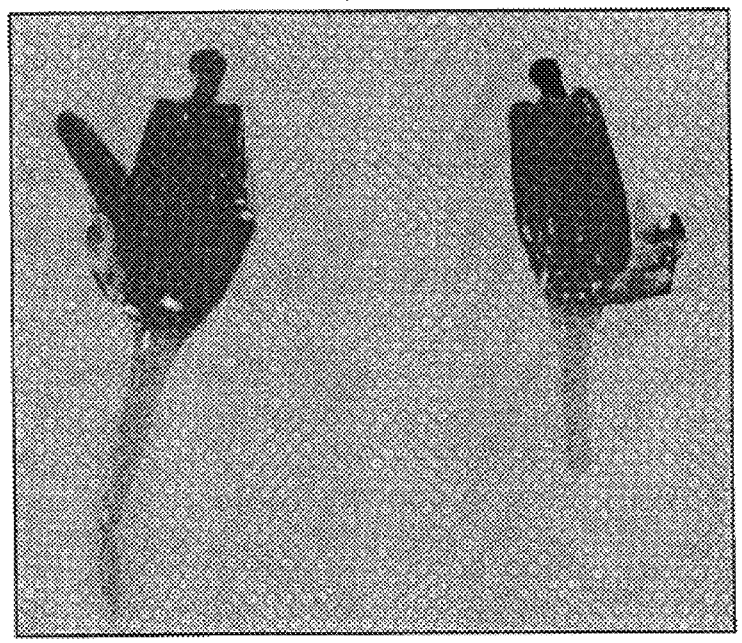
FIGS. 52 to 55 show GUS expression in stigma and style of ethanol induced oil seed rape flowers.
Figure 53:
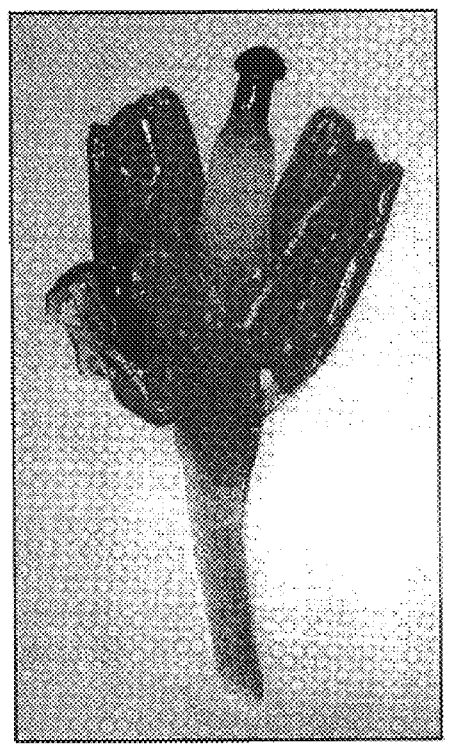
Figure 54:
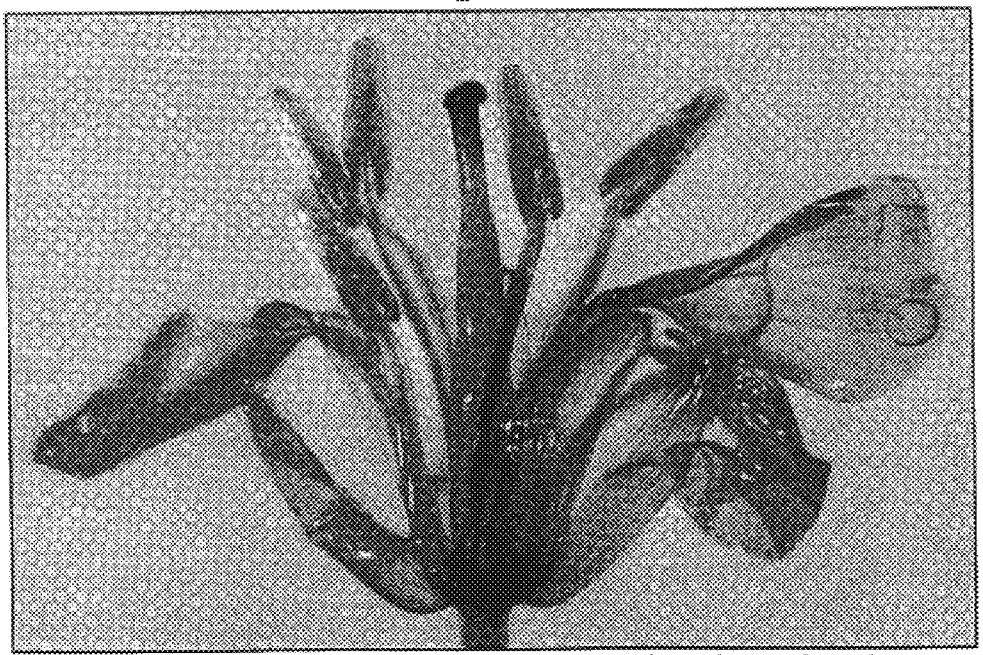
Figure 55:
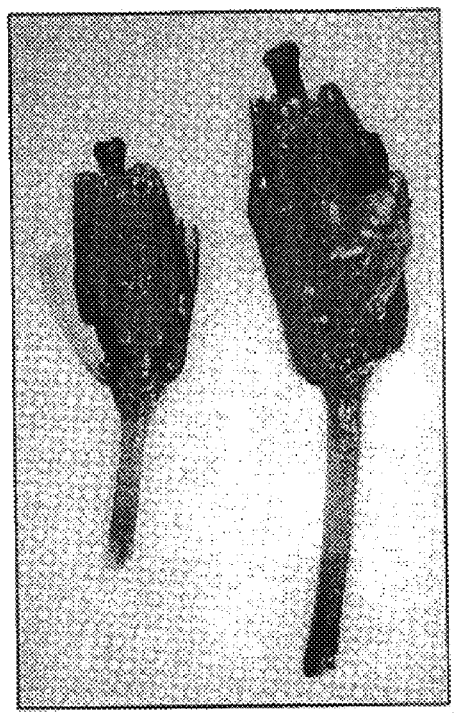
Figure 56:
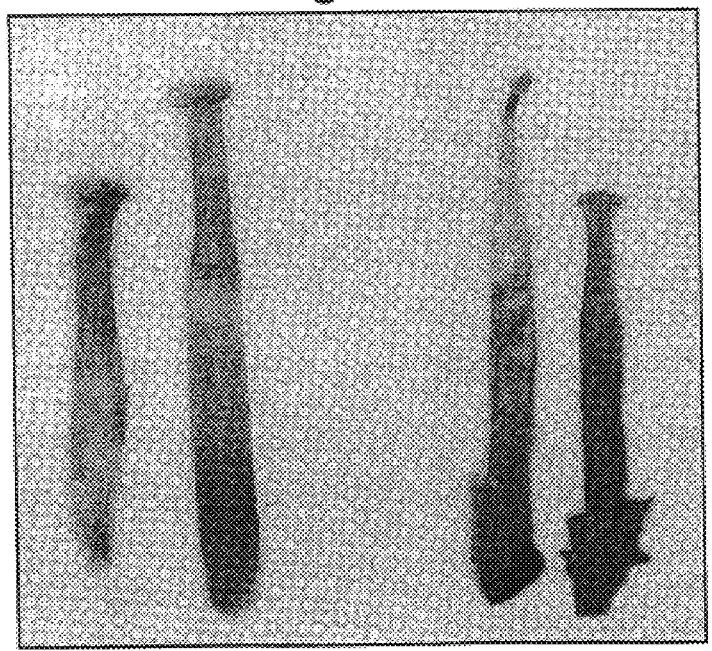
FIG. 56 shows wild type and water induced Alc-GUS oil seed rape pistils.
Figure 57:
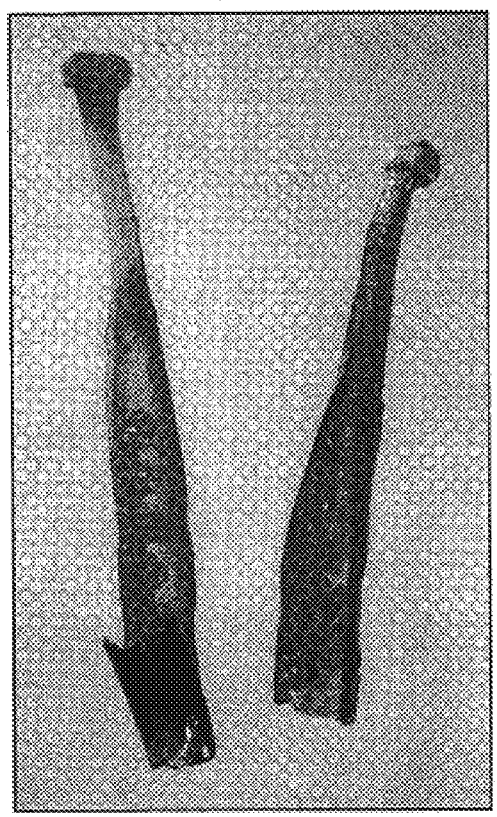
FIG. 57 shows Alc-GUS oil seed rape pistils two days after 2% ethanol root drench.
Figure 58:
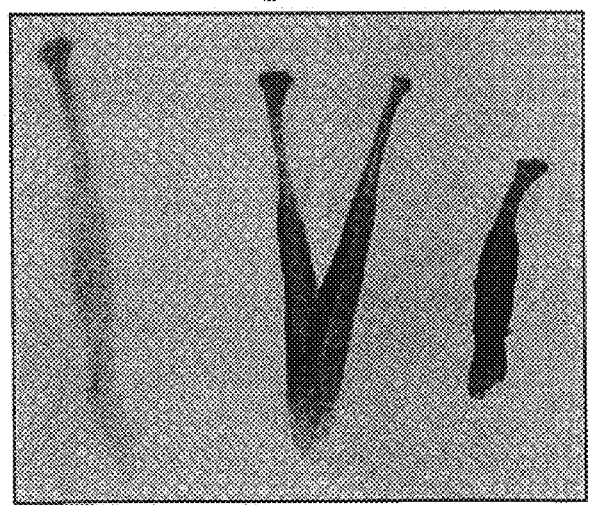
FIG. 58 shows water treated and 5% ethanol treated Alc-GUS pistils.

FIG. 52 shows immature flower buds with the sepals and flowers removed. The ethanol treated plant on the right shows GUS expression in the stigma/style region compared to the water treated control on the left. FIGS. 53–55 are further examples of this. FIG. 56 shows pistil sections from wild type and water induced oilseed rape Alc-GUS plants. FIG. 57 shows pistil sections from a plant root drenched with 2% ethanol two days before the flower samples were taken. This shows induction of GUS throughout the pistil region. FIG. 58 shows pistils from a water-treated plant and a 5% ethanol treated plant. Again it is shown that the application of the chemical ethanol has led to the induction of GUS in the female tissues.

Figure 59:
FIG. 59 shows oil seed rape flower after induction.

FIG. 59 shows a flower from an experiment where a flower stem was cut and placed into a beaker of 5% ethanol and left for two days before staining the whole inflorescence for GUS activity. Blue staining is apparent in the filaments, sepals, petals and the stigma/style regions of the flower.

Tomato

Figure 60A:
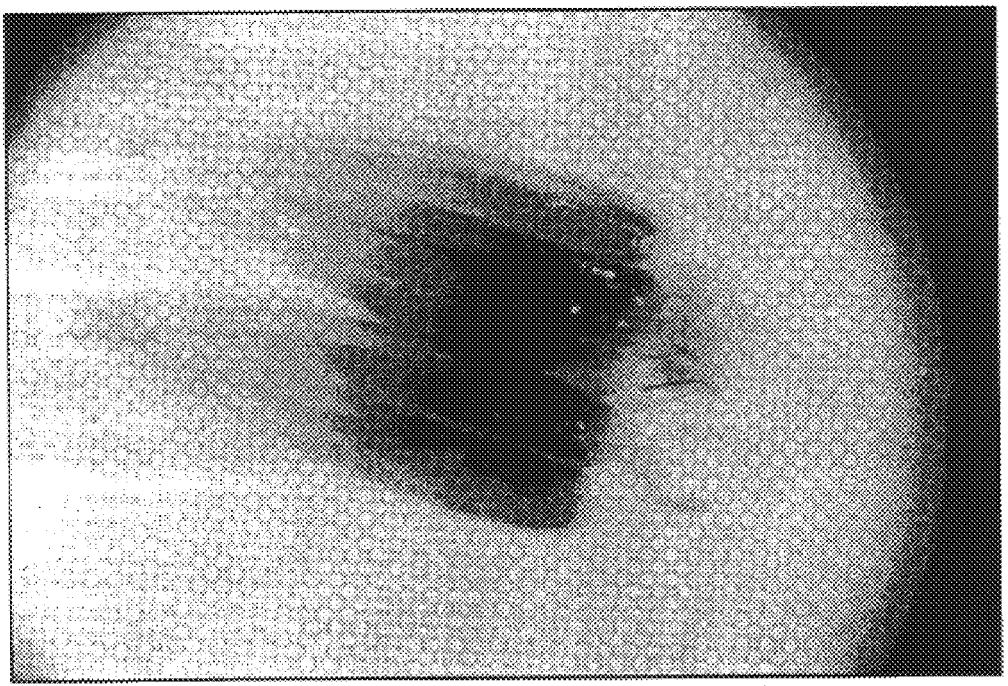
FIG. 60a shows GUS expression in tomato anthers, driven by the AlcA promoter and 60b shows GUS expression in tomato pollen, driven by the AlcA promoter.
Figure 60B:
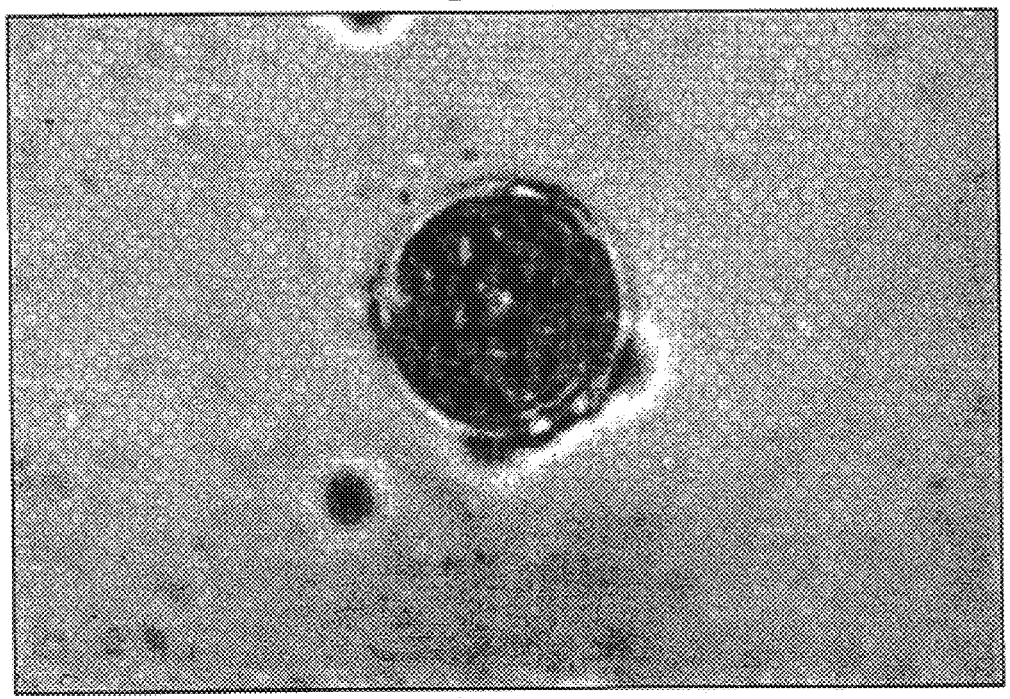

Alc-GUS tomoato flowers were induced using ethanol vapour as described above for tobacco flowers. Two days after induction, anthers and pollen were stained to detect GUS expression. As can be seen in FIGS. 60a and 60b, blue staining was observed in both tissues.

Rice

Early experiments to test the inducibility of the Alc switch in rice include a hydroponics test involving leaf discs exposed to ethanol vapour for two days before assaying for GUS activity. Once in the glasshouse, whole plants are root-drenched with 1–5% ethanol before and during pannicle formation/flowering phase to investigate induction of GUS expression in the flower tissues.

GUS Assays

Flower material was ground in 2–300 µl of extraction buffer (100 mM sodium phosphate buffer pH 7, 10 mM EDTA, 0.1% Triton X-100, 1% Sarcosyl, 10 mM b-mercaptoethanol). Samples were spun in a microcentrifuge for 15 min and 5 µl of the supernatant was used for Bradford protein assays with BSA as standard. 20 µl was diluted 1 in 5 with extraction buffer and 400 µl of assay buffer (same for extraction buffer except contains 1 mM 4-MUG and 20% methanol). 100 µl was taken ($T_0$ sample) and added to 900 µl of stop buffer (0.2M sodium carbonate) and the rest was incubated at 37° C. for two hours before taking a further 100 µl ($T_2$ samples) to be added to 900 µl stop buffer.

Florescence of samples was measured in a spectrophotometer and GUS was represented as nM 4M U per mg protein per hour.

Wheat

Scutellum tissue is bombarded with pUIRN.AGS and the tissue exposed to ethanol vapour. Staining for GUS expression is performed after 2–3 days, when numerous blue spots are seen indicating that the AlcA promoter is induced leading to GUS expression. Transgenic Alc-GUS plants obtained are grown to maturity and seed harvested, inducible GUS expression is determined on the progeny plants in the same way as described above for rice.

GUS Histochemistry

For the GUS staining, the protocol of Blume and Grierson (1997) was used.

Investigation of Sterility

1)Male Sterile Plants
  a) Sporophytic male sterile plants generated by transformation with cassette A are identified by the lack of pollen or by the presence of dead pollen. Seed is produced by back crossing with wild type tobacco as pollen donor.
  b) Gametophytic sterile plants generated by transformation with cassette B are identified using vital stain on the pollen, 50% of the pollen is sterile, 50% fertile.

2) Female Sterile Plants

Sporophytic female sterile plants generated by transformation with cassette F are identified by their inability to be cross pollinated with wild type pollen. Restorer plants in both cases generated by transformation with cassettes E and G are self pollinated, progeny grown and homozygous lines selected in the usual way by selection on kanamycin of T2 seed.

Inducible Restoration of Fertility

The progeny of the cross between sporophytically sterile plants and wild type plants are expected to segregate 1:1 for sterility with the presence of the transgene and are selected at an early growth stage by PCR analysis. Induction experiments are performed to investigate restoration of fertility, as these sterile plants can be treated with ethanol via a root drench or spray or vapour application to induce expression of barstar in the relevant tissues. It is expected that induction at the appropriate time allows self pollination to occur and seed production follows which can be easily scored. Homozygous plants are selected from the resultant progeny by the usual means and used to test the constitutive restoration by crossing with homozygous restorer plants.

Back crossing the C5-barnase.AlcA-barstar plants with wild type plants or allowing self pollination to proceed, however, results in the recovery of a population, 50% of which are fully fertile and 50% producing pollen of which only 50% is fertile. These plants can however be induced with an ethanol spray, root drench or vapour treatment to express barstar in the developing pollen to allow self pollination. The homozygous plants in this case are 100% sterile, whereas the hemizygous plants are 50% sterile. The differences in results obtained by staining allows conclusions to be drawn about the efficiency of induction and self pollination.

Constitutive Restoration of Fertility by Cross Pollination

The crossing of the male sterile plants with the male restorer plant is achieved by transferring pollen from the restorer plant to the pistil of the male sterile plant (after removal of any anthers that are present even though these will contain only dead pollen.) The pollinated pistil is then bagged to prevent contamination by wild type or other pollen in the environment. Seed produced is harvested. Progeny are grown and the production of pollen is observed and measured. Restoration of fertility in this way leads to normal pollen production.

The crossing of the female sterile plants is achieved by transferring pollen from these plants to the pistils of the female fertility restorer plants, again after removal of the anthers from these plants. The flower is bagged as above. Seed produced is harvested. The progeny are grown and the flowers bagged. The ability of these plants to self pollinate is observed. Restoration of fertility in this way allows self pollination to occur. In the same way the plants generated by transformation with cassettes E and F ie female sterile and carrying the male restorer gene and cassettes A and G ie male sterile and carrying the female restorer gene are analysed.

Other modifications to the present invention will be apparent to those skilled in the art without departing from the scope of the invention.

REFERENCES

Aarts et al., Transposon Tagging of a Male Sterility Gene in Arabidopsis. Nature, 363:715–717

Ahn, S, Tanksley, S. D, (1 993). Comparative linkage maps of the rice and maize genomes. Proc Nat Acad Sci 90: 7980–7984.

Albani D., Robert L. S., Donaldson P. A., Altosaar I., Amison P. G., Fabijanski S. F. (1990) Characterization of a pollen-specific gene family from Brassica napus which is activated during early microspore development. Plant Mol. Biol. 15:605–622 Aoyama et al. (1995) Plant Cell 7, 1773

Atkinson, A. H., Heath, R. L., Simpson, R. J., Clarke, A. E., and Anderson, M. A. (1993). Proteinase inhibitors in Nicotiana alata stigmas are derived from a precursor protein which is processed into five homologous inhibitors. Plant Cell 5, 203–213.

Becker D et al. Fertile transgenic wheat from microprojectile bombardment of scutellar tissue. Plant Journal 5: 299–307 (1994)

Budelier K. A., Smith, A. G., and Gasser, C. S. (1990). Regulation of a stylar transmitting tissue-specific gene in wild type and transgenic tomato and tobacco. Mol. Gen. Genet 224, 183–192.

Mark X. Caddick, Andrew J. Greenland, Ian Jepson, Klaus-Peter Krause, Nan Qu, Kay V. Riddell, Michael G. Salter, Wolfgang Schuch, Uwe Sonnewald and A. Brian Tomsett (1998) An ethanol inducible gene switch for plants used to manipulate carbon metabolism. Nature Biotechnology Vol16, 177–180.

Paul Christou in Plant Mol Biol 35: 197–203 (1997)

De Block, M., Debrouwer, T., Moens, T. (1997). The development of a nuclear male sterility system in wheat. Expression of the barnase gene under the control of tapetum specific promoters. Theor Appl Genet. 95, 125–131.

H. P Doring (1989). Tagging genes with Maize Transposable elements. An Overview. Maydica 34 (1989) 73–88.

Elliot, R. C., Betzner, A. S., Huttner E., Oakes, M. P., Tucker, W. Q. J., Gerentes, D., Perez, P., and Smyth, D. R. (1996) AINTEGUMENTA, an APELATA2-like gene of Arabidopsis with pleiotrophic roles in ovule development and floral organ growth. Plant Cell 8, 155–168

Ficker, M., Wemmer, T., and Thompson, R. D (1997). A promoter directing high level expression in pistils of transgenic plants. Plant Mol Biol 35, 425–431

Gallie, D. R, Sleat, D. E, Watts, J. W, Tumer, P. C, Wilson, T. M. A, (1987) A comparison of eukaryotic viral 5' leader sequences as enhancers of MnRNA expression in vivo. Nucleic Acids Research 15: 8693–8710.

Gatz C et al. (1991) Mol Gen Genet 227, 229–237

Gatz C et al. (1992) Plant J 2, 397–404

Goldman, M. H., Goldberg, R. B., Mariane, C. (1994). Female sterile tobacco plants are produced by stigma specific cell ablation. EMBO J 13: 2976–2984.

Hamilton, D. A., Bashe, D. M., Stinson, J. R., Mascarenhas, J. P. (1989). Characterisation of a pollen specific genomic clone from maize. Sex Plant Reprod 2, 208–212.

Hanson, D. H., Hamilton, D. A., Travis, J. L., Bashe, D. M., Mascarenhas, J. P. (12989). Characterisation of a pollen specific cDNA clone from Zea Mays and its expression. The Plant Cell 1, 173–179

Hasselhof. J and Gerlach W. L, 1988) Nature Vol 334: 585–591.

Hiei Y et al. Efficient transformation of rice mediated by Agrobacterium. Plant Journal 6: 271–282 (1994)

Hiei Y et al Rice transformation mediated by Agrobacterium tumefaciens. Plant Mol Boil 35: 205–218 (1997)

Hird, D. L., Worrall, D., Hodge, R., Smartt, S., Paul, W and Scott, R (1993). The anther-specific protein encoded by the *Brassica napus* and *Arabidopsis thaliana* A6 gene displays similarity to β-1,30glucanases. *The Plant Journal* 4(6), 1023–1033. Izawa T, Ohnishi T, Toshitsugu N, Ishida N, Hiroyuki E, Hashimoto H, Itoh K, Terada R, Wu C, Miyazaki C, Endo T, Iida S and Shimaamoto K (1997). Transposon tagging in rice. Plant Mol Biol 35: 219–229

Jepson, I, Lay, V., Holt, D. C., Bright, W. J., and Greenland, A. J., (1994). Cloning and characterisation of maize herbicide safener-induced cDNAs encoding subunits of glutathione S-transferase isoforms I, II and IV. Plant Molecular Biology 26: 1855–1866.

Kamalay, J. C., and Goldberg, R. B. (1980). Regulation of structural gene expression in tobacco. *Cell* 19, 935–946

Kang H. G., Noh Y. S., Chung Y. Y., Costa M. A., An K., An G. (1995). Phenotypic alterations of petal and sepal by ectopic expression of a rice MADS box gene in tobacco. *Plant Mol. Biol.* 29:1–10

De Block, M., Debrouwer, T., Moens, T. (1997). The development of a nuclear male sterility system in wheat. Expression of the bamase gene under the control of tapetum specific promoters. *Theor Appl Genet.* 95, 125–131.

Kempin, S. A., Liljigren, S. J., Block, L. M., Rounsley, S. D., and Yanofsky, M.F. (1997). Targeted disruption in Arabidopsis. *Nature* Vol 389

Kilian A, Chen J, Han F, Steffenson B and Kleinhofs A (1997). Towards map based cloning of the barley stem rust resistance genesRpg1 and rpg4 using rice as an intergenomic cloning vehicle. Plant Mol Biol 35: 187–195.

Koes R. E., Spelt C. E., van Den Elzen P. J. M., Mol J. N. M. (1989). Cloning and molecular characterization of the chalcone synthase multigene family of Petunia hybrida. *Gene* 81:245–257

Kozak, M (1989), J. Cell. Biol 108: 229–241

Kurata, N, Moore G, Nagamura Y, Foote T, Yano M, Minobe Y, Gale M. (1994) Conservation of genome structure between rice and wheat. Bio/Technology 12:276–278

Lloyd et al. (1994) *Science* 266, 436–439

Lotan, T., Ori, N., and Fluhr, R. (1989). Pathogenesis-related proteins are developmentally regulated in tobacco flowers. *Plant Cell* 1, 881–887

Mascarenhas D, Mettler I. J, Pierce D. A, Lowe, H. W (1990) Intron mediated enhancement of heterologous gene expression in maize. Plant Mol Biol 15: 913–920.

Mariani, C., De Beuckeleer, Marc., Truettner, J., Leemans, J., and Goldberg, R. B (1990). Induction of male sterility in plants by a chimaeric ribonuclease gene. *Nature* Vol 347, 737–741

Celestina Mariani., Veronique Gossele., Marc De Beuckeleer., Marc De Block., Robert B. Goldberg., Willy De Greef and Jan Leemans (1992). A chimaeric ribonuclease-inhibitor gene restores fertility to male sterile plants. *Nature* Vol 357, 384–387.

Merlo, Donald J.; Folkerts, Otto. (Dowelanco, USA). PCT Int. Appl., 117 pp. CODEN: PIXXD2. WO 9713402 A1 970417. Synthetic genes for d-endotoxins optimized for expression in plants and their in generation of lepidopteran-resistant plants.

Mitchell and Tijan (1989) Science 245, 371–378.

Moore G, Devos K. M, Wang Z, Gale M. D. (1995). Cereal genome evolution. Current Biol 5: 737–739

Nadeau, J. A., Zhang, X. S., Li, J and O'Neill, S. D. (1996). Ovule development: Identification of stage and tissue specific cDNAs. The *Plant Cell* 8, 213–239

Nacken et al: Mol and Gen Genet. 229, 129–136, (1991)

Nasrallah, J. B., and Nasrallah, M. E. (1993). Pollen-stigma signalling in the sporophytic self-incompatibility response. *Plant Cell* 5., 1325–1335.

Nelson, O. E., and Clary, G. B. (1952) J Hered. 43, 205–210

Ori, N., Sessa, G., Lotan, T., Himunelhoch, S., and Fluhr, R. (1990). A major stylar matrix polypeptide (sp41) is a member of the pathogenesis-realated proteins superclass. *EMBO J* 9, 3429–3436

Picard et al. (1993) *TICB* 3, 278–280

Ptashne (1988) *Nature* 355, 683–689

Ptashne and Gann (1990) *Nature* 346, 329–331

Robinson-Beers, K K., Pruitt, R. E., and Gasser, C. S. (1992). Ovule development in wild type Arabidopsis and two female sterile mutants. *Plant Cell* 4, 1237–1249

M. G. Salter, J. A. Paine, K. V. Riddell, I. Jepson, A. J. Greenland, M. X. Caddick and A. B. Tomsett (1998). Characterisation of the ethanol-inducible alc gene expression system for transgenic plants. *Plant Journal* 16 (1) 127–132

Seed, Brian; Haas, Jurgen. (The General Hospital Corp., USA). U.S., 36 pp. Cont.-in-part of U.S. Ser. No. 324,243. CODEN: USXXAM. U.S. Pat. No. 5,795,737 A 980818. Patent written in English. Application: U.S. patent application Ser. No. 95-532390 950922. Priority: U.S. patent application Ser. No. 94-324243 940919 CAN 129:171505. Modulating efficiency of expression of foreign genes in host cells by manipulation of codon usage.

Seurinck J., Truettner J., Goldberg R. B. (1990). Nucleotide sequence of an anther-specific gene. *Nucleic Acids Res*. 18:3403–3403

Simon et al. (I1996) *Nature* 384, 59–62

Spena, A., Estruch, J. J., Prensen, E., Nacken, W., Van Onckelen, H., Sommner, H. (1992). Anther-specific expression of the rolB gene of Agrobacteriun rhizogenes increases IAA content in anthers and alters anther development in whole flower growth. *Theor Appl Genet* 84, 520–527

Theissen G., Strater T., Fischer A., Saedler H. (1995). Structural characterization, chromosomal localization and phylogenetic evaluation of two pairs of AGAMOUS-like MAS-box genes from maize. *Gene* 156:155–166

Tsuchiya T., Toriyama K., Ejiri S., Hinata K. (1994). Molecular characterization of rice genes specifically expressed in the anther tapetum. *Plant Mol. Biol.* 26:1737–1746

Tsuchiya, T., Toriyama, K., Yoshikawa, M., Ejiri, S., Hinata, K., (1995). Tapetum specific expression of the gene for aan endo-β-1,3-glucanase causes male sterility in transgenic tobacco. *Plant Cell Phys.* 36, 487–494.

Twell, D., Wing, R. A., Yamaguchi, J., McCormick, S. (1989). Isolation and expression of an anther-specific gene from tomato. Mol Gen Genet 217, 240–245.

Twell, D., Yamaguchi, J., McCormick, S. (1990). Pollen specific gene expression in transgenic plants: Coordinate regulation of two different tomato gene promoters during microsporogenesis. *Development* 109, 705–713.

Vasil. V, Clancy. M, Ferl, R. J, Vasil. I. K, Hannah. L. C, (1989) Increased Gene Expression by the First I ntron of Maize Shrunken-1 locus IN Grass Species. Plant Phys 91: 1575–1579.

Vasil V et al. Rapid production of transgenic wheat plants by direct bombardment of cultured immature embryos. Biotechnology 11:1553–1558 (1993).

Weeks J T et al. Rapid production of multiple independant lines of fertile transgenic wheat. Plant Phys 102:1077–1084 (1993)

D, Steinecke P, Herget T, Petereit I, Philipp C, Schreier P. H, (1994) Expression of a reporter gene is reduced by a ribozyme in transgenic plants. Mol Gen Genet 245: (465–470)

Wright, S. Y., Suner, M-M., Bell, P. J., Vaudin, M., and Greenland, A. J (1993) Isolation and characterisation of male flower cDNA'S from maize. The Plant Journal 3, 41–49.

Xu, H., Davis, S. P., Kwan, B. Y. H., O'Bries, A. P., Singh, M., Knox, R. P. (1993) Haploid and diploid expression of a *Brassica Campestris* anther specific gene promoter in Arabidopsis and tobacco. *Mol Gen Genet* 239, 58–65.

Yokoi, S., Tsuchiya, T., Toriyama, K., Hinata, K (1997). Tapetum specific expression of the Osg6B promoter-β-glucuronidase gene in transgenic rice. Plant Cell Reports 16, 363–367.

Zou, J. T., Zhan, X. Y., WU, H. M., Wang, H., Cheung, A. Y. (1994). Characterisation of a rice pollen-specific gene and its expression. *Am J Bot* 81, 552–561.

WO94/13822 Methods for stable transformation of wheat, Ciba Geigy.

What is claimed is:

1. A method of producing hybrid seed comprising incorporating a first expression cassette into a first plant to generate a hemizygous female parent plant, said first expression cassette comprising:
    (a) a first gene promoter sequence which is a male flower specific promoter;
    (b) a disrupter gene encoding a protein capable of disrupting male fertility operably linked to the first gene promoter sequence;
    (c) a second gene promoter sequence which is a female tissue specific promoter sequence optionally operably linked to one or more translational enhancer or intron sequences;
    (d) a restorer gene encoding a protein capable of restoring female fertility operably linked to the second gene promoter sequence;
    (e) a third gene promoter sequence responsive to the presence or absence of an exogenous chemical inducer said third gene promoter sequence optionally operably linked to one or more translational enhancer or intron sequences; and
    (f) a restorer gene encoding a protein capable of restoring male fertility operably linked to the third gene promoter sequence;
whereby the presence of the exogenous chemical inducer controls male fertility; and incorporating a second expression cassette into a second plant to generate a hemizygous male parent plant, said second expression cassette comprising:
    (g) a first gene promoter sequence which is a female flower specific promoter sequence;
    (h) a disrupter gene encoding a protein capable of disrupting female fertility;
    (i) a second gene promoter sequence which is a male tissue specific promoter sequence optionally operably linked to one or more enhancer or intron sequences;
    (j) a restorer gene encoding a protein capable of restoring male fertility operably linked to the second gene promoter sequence;
    (k) a third gene promoter sequence responsive to the presence or absence of an exogenous chemical inducer, said third gene promoter sequence optionally operably linked to one or more enhancer or intron sequences; and
    (l) a restorer gene encoding a protein capable of restoring female fertility operably linked to the third gene promoter sequence;
        whereby the presence of the exogenous chemical inducer controls female fertility;
        applying an exogenous chemical inducer to the transformants thereby allowing the plants to self-pollinate;
        growing up plants from the resulting seed;
        selecting for male and female homozygous plants;
        crossing the selected male and female plants; and
        obtaining the resulting hybrid seed.

2. A method according to claim 1 wherein the male flower specific promoter sequence is a gametophytic promoter sequence.

3. A method according to claim 1 wherein the male flower specific promoter sequence is a sporophytic promoter sequence.

4. A method according to claim 1 wherein the plants are selected from the group consisting of wheat, rice, maize, tomato, sunflower, sugarbeet, canola, cotton, soybean and other vegetables.

5. A method according to claim 1 wherein the disrupter gene encoding a product capable of disrupting male fertility encodes a product which is capable of disrupting pollen production.

6. A method according to claim 1 wherein the third gene promoter sequece is the AlcA promoter sequence or the GST-27 promoter sequence.

7. A method according to claim 1 wherein the restorer gene encoding a product capable of restoring male fertility encodes a product which is capable of restoring pollen producting.

8. Hybrid seed resulting from the method of claim 1, which hybrid seed comprises the first and second expression cassettes according to claim 1.

* * * * *